(12) United States Patent
Braven et al.

(10) Patent No.: US 10,094,800 B2
(45) Date of Patent: *Oct. 9, 2018

(54) ASSAYS AND APPARATUS FOR DETECTING ELECTROCHEMICAL ACTIVE MARKERS IN AN ELECTRIC FIELD

(71) Applicant: Atlas Genetics Limited, Bristol (GB)

(72) Inventors: Helen Braven, Melksham (GB); Russell Keay, Melksham (GB)

(73) Assignee: Atlas Genetics Limited, Trowbridge, Wiltshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/603,555

(22) Filed: Jan. 23, 2015

(65) Prior Publication Data

US 2015/0159203 A1    Jun. 11, 2015

Related U.S. Application Data

(63) Continuation of application No. 10/506,958, filed as application No. PCT/GB03/00613 on Feb. 11, 2003, now Pat. No. 9,127,308.

(30) Foreign Application Priority Data

Mar. 7, 2002    (GB) .................................. 0205455.9

(51) Int. Cl.
| | |
|---|---|
| *G01N 27/327* | (2006.01) |
| *C12Q 1/6816* | (2018.01) |
| *C12Q 1/6823* | (2018.01) |
| *C12Q 1/686* | (2018.01) |
| *G01N 27/30* | (2006.01) |
| *G01N 27/416* | (2006.01) |
| *G01N 33/487* | (2006.01) |
| *B01L 7/00* | (2006.01) |

(52) U.S. Cl.
CPC ............ *G01N 27/3277* (2013.01); *B01L 7/52* (2013.01); *C12Q 1/686* (2013.01); *C12Q 1/6816* (2013.01); *C12Q 1/6823* (2013.01); *G01N 27/308* (2013.01); *G01N 27/416* (2013.01); *G01N 33/48721* (2013.01); *B01L 2300/0645* (2013.01); *B01L 2300/18* (2013.01); *G01N 2458/30* (2013.01)

(58) Field of Classification Search
CPC ............ G01N 2458/30; G01N 27/308; G01N 27/416; G01N 33/48721; B01L 7/52; B01L 2300/0645; B01L 2300/18; C12Q 1/6816; C12Q 1/6823; C12Q 1/686
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,840,893 A | 6/1989 | Hill et al. |
| 4,889,818 A | 12/1989 | Gelfand et al. |
| 5,038,852 A | 8/1991 | Johnson et al. |
| 5,079,352 A | 1/1992 | Gelfand et al. |
| 5,234,809 A | 8/1993 | Boom et al. |
| 5,310,652 A | 5/1994 | Gelfand et al. |
| 5,312,527 A | 5/1994 | Mikkelsen et al. |
| 5,312,590 A | 5/1994 | Gunasingham |
| 5,322,770 A | 6/1994 | Gelfand |
| 5,333,675 A | 8/1994 | Mullis et al. |
| 5,407,800 A | 4/1995 | Gelfand et al. |
| 5,476,774 A | 12/1995 | Wang et al. |
| 5,487,972 A | 1/1996 | Gelfand et al. |
| 5,518,900 A | 5/1996 | Nikiforov et al. |
| 5,538,848 A | 7/1996 | Livak et al. |
| 5,556,751 A | 9/1996 | Stefano |
| 5,591,578 A | 1/1997 | Meade et al. |
| 5,593,867 A | 1/1997 | Walker et al. |
| 5,605,622 A | 2/1997 | Ferraro |
| 5,605,662 A | 2/1997 | Heller et al. |
| 5,614,402 A | 3/1997 | Dahlberg et al. |
| 5,656,493 A | 8/1997 | Mullis et al. |
| 5,660,988 A | 8/1997 | Duck et al. |
| 5,691,142 A | 11/1997 | Dahlberg et al. |
| 5,705,348 A | 1/1998 | Meade et al. |
| 5,705,365 A | 1/1998 | Ryder et al. |
| 5,719,028 A | 2/1998 | Dahlberg et al. |
| 5,763,181 A | 6/1998 | Han et al. |
| 5,770,369 A | 6/1998 | Meade et al. |
| 5,770,370 A | 6/1998 | Kumar |
| 5,776,672 A | 7/1998 | Hashimoto et al. |
| 5,780,234 A | 7/1998 | Meade et al. |
| 5,795,763 A | 8/1998 | Dahlberg et al. |

(Continued)

FOREIGN PATENT DOCUMENTS

| | | |
|---|---|---|
| DE | 19633206 A1 | 2/1998 |
| EP | 0 125 137 A2 | 11/1984 |

(Continued)

OTHER PUBLICATIONS

Yu et al ( J. Am Chem Soc (2001) voume 123) 11155-1161).*

(Continued)

*Primary Examiner* — Steven Pohnert
(74) *Attorney, Agent, or Firm* — Mintz Levin Cohn Ferris Glovsky and Popeo, P.C.

(57) ABSTRACT

The invention provides a method of probing for a nucleic acid comprising: contacting a nucleic acid solution with an oligonucleotide probe labelled with an electrochemically active marker, providing conditions at which the probe is able to at least partially hybridize with any complementary target sequence which may be present in the nucleic acid solution, selectively degrading either hybridized, partially hybridized or unhybridized nucleic acid probe, and electrochemically determining information relating to the electrochemically active marker. The invention further provides novel molecules with use in methods of the invention.

20 Claims, 38 Drawing Sheets

Specification includes a Sequence Listing.

(56) References Cited

U.S. PATENT DOCUMENTS

| | | |
|---|---|---|
| 5,804,375 A | 9/1998 | Gelfand et al. |
| 5,824,473 A | 10/1998 | Meade et al. |
| 5,837,446 A | 11/1998 | Cozzette et al. |
| 5,837,450 A | 11/1998 | Dahlberg et al. |
| 5,837,469 A | 11/1998 | Harris |
| 5,843,654 A | 12/1998 | Heisler et al. |
| 5,846,717 A | 12/1998 | Brow et al. |
| 5,871,918 A | 2/1999 | Thorp et al. |
| 5,888,780 A | 3/1999 | Dahlberg et al. |
| 5,939,256 A | 8/1999 | Yamamoto et al. |
| 5,952,172 A | 9/1999 | Meade et al. |
| 5,985,557 A | 11/1999 | Prudent et al. |
| 5,994,069 A | 11/1999 | Hall et al. |
| 6,001,567 A | 12/1999 | Brow et al. |
| 6,013,459 A | 1/2000 | Meade |
| 6,027,890 A | 2/2000 | Ness et al. |
| 6,063,259 A | 5/2000 | Wang et al. |
| 6,063,573 A | 5/2000 | Kayyem |
| 6,071,699 A | 6/2000 | Meade et al. |
| 6,087,100 A | 7/2000 | Meade et al. |
| 6,090,543 A | 7/2000 | Prudent et al. |
| 6,096,273 A | 8/2000 | Kayyem et al. |
| 6,127,127 A | 10/2000 | Eckhardt et al. |
| 6,127,155 A | 10/2000 | Gelfand et al. |
| 6,127,543 A | 10/2000 | Brocard et al. |
| 6,150,106 A | 11/2000 | Martin et al. |
| 6,159,745 A | 12/2000 | Roberts et al. |
| 6,177,250 B1 | 1/2001 | Meade et al. |
| 6,180,350 B1 | 1/2001 | Netzel |
| 6,180,352 B1 | 1/2001 | Meade et al. |
| 6,194,149 B1 | 2/2001 | Neri et al. |
| 6,200,761 B1 | 3/2001 | Meade et al. |
| 6,214,979 B1 | 4/2001 | Gelfand et al. |
| 6,221,583 B1 | 4/2001 | Kayyem et al. |
| 6,221,586 B1 | 4/2001 | Barton et al. |
| 6,232,062 B1 | 5/2001 | Kayyem et al. |
| 6,238,870 B1 | 5/2001 | Meade et al. |
| 6,258,545 B1 | 7/2001 | Meade et al. |
| 6,264,825 B1 | 7/2001 | Blackburn et al. |
| 6,268,149 B1 | 7/2001 | Meade et al. |
| 6,268,150 B1 | 7/2001 | Meade et al. |
| 6,288,221 B1 | 9/2001 | Grinstaff et al. |
| 6,290,839 B1 | 9/2001 | Kayyem et al. |
| 6,291,188 B1 | 9/2001 | Meade et al. |
| 6,294,670 B1 | 9/2001 | Takenaka |
| 6,342,359 B1 | 1/2002 | Lee et al. |
| 6,348,314 B1 | 2/2002 | Prudent et al. |
| 6,355,436 B1 | 3/2002 | Martin et al. |
| 6,361,951 B1 | 3/2002 | Thorp et al. |
| 6,372,424 B1 | 4/2002 | Brow et al. |
| 6,432,723 B1 | 8/2002 | Plaxco et al. |
| 6,444,423 B1 | 9/2002 | Meade et al. |
| 6,445,486 B1 | 9/2002 | Lomprey et al. |
| 6,458,535 B1 | 10/2002 | Hall et al. |
| 6,496,294 B2 | 12/2002 | Lomprey et al. |
| 6,528,266 B2 | 3/2003 | Meade et al. |
| 6,531,283 B1 | 3/2003 | Kingsmore et al. |
| 6,562,577 B2 | 5/2003 | Martin et al. |
| 6,562,611 B1 | 5/2003 | Kaiser et al. |
| 6,576,475 B1 | 6/2003 | Schiffrin et al. |
| 6,613,508 B1 | 9/2003 | Ness et al. |
| 6,673,616 B1 | 1/2004 | Dahlberg et al. |
| 6,692,917 B2 | 2/2004 | Neri et al. |
| 6,706,471 B1 | 3/2004 | Brow et al. |
| 6,709,825 B2 | 3/2004 | Mirkin et al. |
| 6,759,226 B1 | 7/2004 | Ma et al. |
| 6,770,190 B1 | 8/2004 | Milanovski et al. |
| 6,824,669 B1 | 11/2004 | Li et al. |
| 6,864,055 B2 | 3/2005 | Makino et al. |
| 6,872,816 B1 | 3/2005 | Hall et al. |
| 6,875,572 B2 | 4/2005 | Prudent et al. |
| 6,913,881 B1 | 7/2005 | Aizenstein et al. |
| 6,951,936 B2 | 10/2005 | Takenaka |
| 6,974,703 B2 | 12/2005 | Mauze et al. |
| 6,977,151 B2 | 12/2005 | Kayyem et al. |
| 7,005,265 B1 | 2/2006 | Fan et al. |
| 7,011,944 B2 | 3/2006 | Prudent et al. |
| 7,019,146 B1 | 3/2006 | Ishigai et al. |
| 7,029,919 B2 | 4/2006 | Mauze et al. |
| 7,030,257 B2 | 4/2006 | Gao et al. |
| 7,045,289 B2 | 5/2006 | Allawi et al. |
| 7,049,129 B2 | 5/2006 | Mauze et al. |
| 7,052,591 B2 | 5/2006 | Gao et al. |
| 7,087,381 B2 | 8/2006 | Dahlberg et al. |
| 7,098,320 B1 | 8/2006 | Mirkin et al. |
| 7,101,672 B2 | 9/2006 | Dong et al. |
| 7,112,422 B2 | 9/2006 | Han et al. |
| 7,122,364 B1 | 10/2006 | Lyamichev et al. |
| 7,132,266 B2 | 11/2006 | Makino et al. |
| 7,150,982 B2 | 12/2006 | Allawi et al. |
| 7,195,871 B2 | 3/2007 | Lyamichev et al. |
| 7,202,037 B2 | 4/2007 | Barton et al. |
| 7,256,020 B2 | 8/2007 | Lyamichev et al. |
| 7,256,311 B2 | 8/2007 | Abdur-Rashid et al. |
| 7,267,939 B2 | 9/2007 | Meade |
| 7,279,536 B2 | 10/2007 | Brant et al. |
| 7,301,041 B2 | 11/2007 | Chaix-Bauvais et al. |
| 7,306,917 B2 | 12/2007 | Prudent et al. |
| 7,309,723 B2 | 12/2007 | Porter et al. |
| 7,354,708 B2 | 4/2008 | Hall et al. |
| 7,371,530 B2 | 5/2008 | Han et al. |
| 7,381,530 B2 | 6/2008 | Hall et al. |
| 7,393,644 B2 | 7/2008 | Lee et al. |
| 7,407,782 B2 | 8/2008 | Prudent et al. |
| 7,432,048 B2 | 10/2008 | Neri et al. |
| 7,482,118 B2 | 1/2009 | Allawi et al. |
| 7,482,127 B2 | 1/2009 | Agarwal et al. |
| 7,514,220 B2 | 4/2009 | Hall et al. |
| 7,514,228 B2 | 4/2009 | Meade |
| 7,527,928 B2 | 5/2009 | Neri et al. |
| 7,541,145 B2 | 6/2009 | Prudent et al. |
| 7,566,534 B2 | 7/2009 | Meade |
| 7,579,145 B2 | 8/2009 | Meade |
| 7,582,419 B2 | 9/2009 | Meade |
| 7,588,891 B2 | 9/2009 | Prudent et al. |
| 7,595,153 B2 | 9/2009 | Meade |
| 7,601,496 B2 | 10/2009 | Dahlberg et al. |
| 7,655,404 B2 | 2/2010 | Gao et al. |
| 7,691,573 B2 | 4/2010 | Dahlberg et al. |
| 7,759,062 B2 | 7/2010 | Allawi et al. |
| 7,803,542 B2 | 9/2010 | Xiao et al. |
| 7,820,387 B2 | 10/2010 | Neri et al. |
| 7,824,862 B2 | 11/2010 | Dong et al. |
| 7,829,314 B2 | 11/2010 | Prudent et al. |
| 7,851,146 B2 | 12/2010 | Meade et al. |
| 7,851,150 B2 | 12/2010 | Dahlberg et al. |
| 7,893,177 B1 | 2/2011 | Porter et al. |
| 2001/0049105 A1 | 12/2001 | Singh et al. |
| 2002/0051974 A1 | 5/2002 | Dodge et al. |
| 2003/0148335 A1 | 8/2003 | Shen et al. |
| 2003/0219801 A1 | 11/2003 | Lipshutz |
| 2004/0152097 A1 | 8/2004 | Takenaka |
| 2005/0037397 A1 | 2/2005 | Mirkin et al. |
| 2005/0214759 A1 | 9/2005 | Wlassof et al. |
| 2005/0214809 A1 | 9/2005 | Han |
| 2010/0184028 A1 | 7/2010 | Hsing et al. |

FOREIGN PATENT DOCUMENTS

| | | |
|---|---|---|
| EP | 0 125 139 A2 | 11/1984 |
| EP | 0 125 867 A2 | 11/1984 |
| EP | 0 127 958 A2 | 12/1984 |
| EP | 0 142 301 A2 | 5/1985 |
| EP | 0 149 339 A2 | 7/1985 |
| EP | 0 150 999 A2 | 8/1985 |
| EP | 0 167 248 A2 | 1/1986 |
| EP | 0 351 892 A2 | 1/1990 |
| EP | 351891 A2 | 1/1990 |
| EP | 0 502 588 A2 | 9/1992 |
| EP | 0 502 589 A2 | 9/1992 |
| EP | 0 505 012 A2 | 9/1992 |
| EP | 0 509 612 A2 | 10/1992 |
| EP | 0 632 134 A2 | 1/1995 |
| EP | 0 776 967 A2 | 6/1997 |

(56) References Cited

FOREIGN PATENT DOCUMENTS

| | | |
|---|---|---|
| EP | 0 776 970 A1 | 6/1997 |
| EP | 0 819 696 A2 | 1/1998 |
| EP | 0 894 860 A1 | 2/1999 |
| EP | 1 067 134 A2 | 1/2001 |
| EP | 1 120 155 A2 | 8/2001 |
| EP | 1 120 156 A2 | 8/2001 |
| EP | 1 120 157 A2 | 8/2001 |
| EP | 1 120 469 A2 | 8/2001 |
| EP | 1 193 315 A1 | 4/2002 |
| EP | 1 302 549 A2 | 4/2003 |
| EP | 1 340 764 A2 | 9/2003 |
| EP | 1 352 973 A2 | 10/2003 |
| EP | 1 505 160 A2 | 2/2005 |
| EP | 1 524 695 A2 | 4/2005 |
| EP | 1 580 597 A2 | 9/2005 |
| EP | 1 591 533 A1 | 11/2005 |
| EP | 1 634 890 A1 | 3/2006 |
| EP | 1 877 415 A2 | 1/2008 |
| EP | 2 055 781 A2 | 5/2009 |
| EP | 2 058 407 A2 | 5/2009 |
| GB | 2154003 A | 8/1985 |
| GB | 2467148 A | 7/2010 |
| JP | 2007-168423 A | 7/2007 |
| JP | 2009-292955 A | 12/2009 |
| WO | WO-91/09944 A2 | 7/1991 |
| WO | WO-91/09950 A1 | 7/1991 |
| WO | WO-92/01814 A2 | 2/1992 |
| WO | WO-92/03556 A1 | 3/1992 |
| WO | WO-92/06200 A1 | 4/1992 |
| WO | WO-92/06202 A1 | 4/1992 |
| WO | WO-92/10589 A1 | 6/1992 |
| WO | WO-94/16090 A1 | 7/1994 |
| WO | WO-95/12607 A1 | 5/1995 |
| WO | WO-95/12808 A1 | 5/1995 |
| WO | WO-95/15970 A1 | 6/1995 |
| WO | WO-95/15971 A2 | 6/1995 |
| WO | WO-95/17524 A2 | 6/1995 |
| WO | WO-95/34890 A1 | 12/1995 |
| WO | WO-96/01836 A1 | 1/1996 |
| WO | WO-96/07917 A1 | 3/1996 |
| WO | WO-96/40712 A1 | 12/1996 |
| WO | WO-97/09337 A1 | 3/1997 |
| WO | WO-97/12030 A1 | 4/1997 |
| WO | WO-97/12995 A1 | 4/1997 |
| WO | WO-97/27325 A1 | 7/1997 |
| WO | WO-97/27327 A2 | 7/1997 |
| WO | WO-97/46568 A1 | 12/1997 |
| WO | WO-98/10273 A1 | 3/1998 |
| WO | WO-98/10277 A1 | 3/1998 |
| WO | WO-98/14542 A1 | 4/1998 |
| WO | WO-98/23774 A1 | 6/1998 |
| WO | WO-98/24544 A1 | 6/1998 |
| WO | WO-98/28320 A2 | 7/1998 |
| WO | WO-98/42873 A1 | 10/1998 |
| WO | WO-98/57159 A1 | 12/1998 |
| WO | WO-98/59066 A1 | 12/1998 |
| WO | WO-99/05319 A2 | 2/1999 |
| WO | WO-99/29711 A1 | 6/1999 |
| WO | WO-99/38612 A1 | 8/1999 |
| WO | WO-99/42558 A1 | 8/1999 |
| WO | WO-99/43853 A1 | 9/1999 |
| WO | WO-99/57317 A1 | 11/1999 |
| WO | WO-99/57319 A1 | 11/1999 |
| WO | WO-00/11473 A1 | 3/2000 |
| WO | WO-00/32813 A1 | 6/2000 |
| WO | WO-00/37163 A1 | 6/2000 |
| WO | WO-00/42217 A2 | 7/2000 |
| WO | WO-00/55366 A1 | 9/2000 |
| WO | WO-00/61805 A1 | 10/2000 |
| WO | WO-00/62931 A1 | 10/2000 |
| WO | WO-00/65099 A1 | 11/2000 |
| WO | WO-01/04131 A1 | 1/2001 |
| WO | WO-01/06016 A2 | 1/2001 |
| WO | WO-01/07665 A2 | 2/2001 |
| WO | WO-01/34765 A1 | 5/2001 |
| WO | WO-01/90337 A2 | 11/2001 |
| WO | WO-02/13880 A2 | 2/2002 |
| WO | WO-02/46363 A2 | 6/2002 |
| WO | WO-02/063030 A2 | 8/2002 |
| WO | WO-02/074984 A2 | 9/2002 |
| WO | WO-03/004160 A1 | 1/2003 |
| WO | WO-03/06878 A1 | 1/2003 |
| WO | WO-03003810 A2 | 1/2003 |
| WO | WO-03/023365 A2 | 3/2003 |
| WO | WO-03/068787 A1 | 8/2003 |
| WO | WO-03/073067 A2 | 9/2003 |
| WO | WO-2004/044549 A2 | 5/2004 |
| WO | WO-2004/111269 A1 | 12/2004 |
| WO | WO-2006/006196 A2 | 1/2006 |
| WO | WO-2008/113686 A2 | 9/2008 |
| WO | WO-2009/032901 A1 | 3/2009 |
| WO | WO-2010/004197 A2 | 1/2010 |

OTHER PUBLICATIONS

Subramanian et al (Nucleic Acid research (2003) vol. 31, pp. 1585-1596).*
DNase I (RNase-free) (New England Biolabs (https://www.neb.com/products/m0303-dnase-i-rnase-free, downloaded Mar. 24, 2015).*
Lowman et al (the Journal of Biological Chemistry (1986) vol. 261, pp. 5396-5403).*
Shagin et al ( Genome Reseach (2002) vol. 12, pp. 1935-1942).*
Promega (https://www.promega.com/resources/product-guides-and-selectors/restriction-enzyme-resource/restriction-enzyme-general-information/, downloaded Aug. 15, 2016).*
Evrogen (http://evrogen.com/products/DSN/DSN_Description.shtml, downloaded Aug. 15, 2016).*
Sigma Nucleases (http://www.sigmaaldrich.com/life-science/metabolomics/enzyme-explorer/learning-center/nucleases.html, downloaded Aug. 15, 2016).*
Chaudhry (Nucleic Acids Research (1995) vol. 23, pp. 3085-3809).*
Zhao ( Nucleic acids research (2007) vol. 36, e14, pp. 1-5).*
Holland (proceedings National Academy of Sciences (1991) vol. 88, pp. 7276-7280).*
Beilstein et al. "On-Column Derivitization of Oligodeoxynucleotides with Ferrocene." *Chem. Commun.* 6(2000):509-510.
Beilstein et al. "Synthesis and Characterization of Ferrocene-Labeled Oligodeoxynucleotides." *J. Organometallic Chem.* 637-639(2001):398-1406.
Berney et al. "A DNA Diagnostic Biosensor: Development, Characterisation and Performance." *Sensors and Actuator B*. 68(2000):100-108.
Boon et al. "Mutation Detection by Electrocatalysis at DNA-Modified Electrodes." *Nat. Biol.* 18(2000):1096-1100.
Calzone et al. "Mapping of Gene Transcripts by Nuclease Protection Assays and cDNA Primer Extension." *Meth Enzymol.* 152(1987):611-632.
Caruana et al. "Enzyme-Amplified Amperometric Detection of Hybridization and of a Single Base Pair Mutation in an 18-Base Oligonucleotide on a 7-urn-Diameter Microelectrode." *J Am. Chem. Soc.* 121.4(1999):769-774.
Griffiths et al. "Man-Made Enzymes—From Design to in vitro Compartmentalisation." *Biotechnol.* 11(2000):338-353.
Ihara et al. "Ferrocene-Oiigonucleotide Conjugates for Electrochemical Probing of DNA." *Nucleic Acids Res.* 24.21(1996):4273-4280.
Mikkelson. "Electrochemical Biosensors for DNA Sequence Detection." *Electroanalysis.* 8.1(1996):15-19.
Millan et al. "Sequence-Selective Biosensor for DNA Based on Electroactive Hybridization Indicators." *Anal. Chem.* 65.17(1993):317-2323.
Millan et al. "Voltammetric DNA Biosensor for Cystic Fibrosis Based on a Modified Carbon Paste Electrode." *Anal. Chem.* 66.18(1994):12943-2948.
Palecek et al. "Detecting DNA Hybridization and Damage." *Anal. Chem.*73.3(2001)74A-83A.

(56) References Cited

OTHER PUBLICATIONS

Patolsky et al. "Detection of Single-Base DNA Mutations by Enzyme-Amplified Electronic Transduction." *Nat. Biotechnol.* 19(2001):253-257.
Patolsky et al. "EleCtronic Trasduction of Polymerase or Reverse Transcriptase Induced Replication Processes on Surfaces: Highly Sensitive and Specific Detection of Viral Genomes." *Agnew. Chem. Int.* 40.12(2001):2261-2265.
Patolsky et al. "Enzyme-Linked Amplified Electrochemical Sensing of Oligonucleotide-DNA Interactions by Means of the Precipitation of an Insoluble Product and Using Imoedance Soectroscoov." *Lanamuir.* 15.11(1999):3703-3706.
Pividiori et al. "Electrochemical Genosensor Design: Immobilisation of Oligonucleotides onto Transducer Surfaces and Detection Methods." *Biosens. Bioelectron.* 15.5-6(2000):291-303.
Popovich. "Mediated Electrochemical Detection of Nucleic Acids for Drug Discovery and Clinical Diagnostics." *IVD Technol.* (2001):36-42.
Takenaka et al. "Electrochemically Active DNA Probes: Detection of Target DNA Sequences at Femtomole Level by High-Performance Liquid Chromatography with Electrochemical Detection." *Anal. Biochem.* 218(1994): 436-443.
Thorpe. "Cutting Out the Middleman: DNA Biosensors Based on Electrochemical Oxidation." *Tibtech.* 16(1998):117-121.
Tierney et al. "Synthesis and Characterization of Flourenone-, Anthraquinone-, and Phenothiazine-Labeled Oligodeoxynucleotides: 5'-Probes for DNA Redox Chemistry." *J. Org. Chem.* 65(2000):p. 5355-5359.
Umek et al. "Electronic Detection of Nucleic Acids: A Versatile Platform for Molecular Diagnostics." *J. Mol. Diagn.* 3.2(2001):74-84.
Uto et al. "Electrochemical Analysis of DNA Amplified by the Polymerase Chain Reaction with a Ferrocenylated Oligonucleotide." *Anal. Biochem.* 250(1997):122-124.
Wang et al. "DNA Electrochemical Biosensor for the Detection of Short DNA Sequences Related to the Human Immunodeficiency Virus." *Anal. Chem.* 68.15(1996):2629-2634.
Wang et al. "DNA Electrochemical Biosensors for Environmental Monitoring." *Anal. Chim. Acta.* 347(1997):1-8.
Wang et al. "Electrochemical Measurements of Oligonucleotides in the Presence of Chromosomal DNA Using Membrance-Covered Carbon Electrodes." *Anal. Chem.* 69.19.(1997):4056-4059.
Wang et al. "Peptide Nucleic Acid Probes for Sequence-Specific DNA Biosensors." *J. Am. Chem. Soc.* 118.33(1996):7667-7670.
Wang et al. "Screen-Printed Electrochemical Hybridization Biosensor for the Detection of DNA Sequences from the *Escheria coli* Pathogen." *Electroanal.* 9.5(1997):395-398.
Whittemore et al. "Synthesis and Electrochemistry of Anthraquinone-Oligodeoxynucleotide Conjugates." *Bioconjugate Chem.* 10.2(1999):261-270.
Yu et al. "Electronic Detection of Single-Base Mismatches in DNA with Ferrocene-Modified Probes." *J. Am. Chem. Soc.* 123. 45(2001):1155-11161.
DNase I (RNase-free) New England Biolabs, retrieved online at: http://www.neb.com/products/m0303-dnase-i-rnase-free, 2 pages, downloaded Mar. 24, 2015.
Jaschke, Andres et al., "In Vitro Selected Oligonucleotides as Tools in Organic Chemistry," Synlett, vol. 6:825-833 (1999).
Lin, Su-Fang et al., "Characterization of Epstein-Barr Virus DNase and Its Interaction with the Major DNA Binding Protein," Virology, vol. 208:712-722 (1995).
Subramanian, Krithika et al., "The enzymatic basis of processivity in lambda exonuclease," Nucleic Acids Research, 31(6):1585-1596 (2003).

\* cited by examiner

SEQUENCE LISTING

```
<160> NUMBER OF SEQ ID NOS: 21

<210> SEQ ID NO 1
<211> LENGTH: 26
<212> TYPE: DNA
<213> ORGANISM: Artificial
<220> FEATURE:
<223> OTHER INFORMATION: ACTB (beta actin) probe BAPR
```

<400> SEQUENCE: 1
atgccctccc ccatgccatc ctgcgt                                              26

<210> SEQ ID NO 2
<211> LENGTH: 25
<212> TYPE: DNA
<213> ORGANISM: Artificial
<220> FEATURE:
<223> OTHER INFORMATION: ACTB (beta actin) Probe C9-T1BAPR
<220> FEATURE:
<221> NAME/KEY: misc_feature
<222> LOCATION: (1)..(1)
<223> OTHER INFORMATION: amino modified thymine with C9 linker, Formula
      IV

<400> SEQUENCE: 2
tgccctcccc catgccatcc tgcgt                                               25

<210> SEQ ID NO 3
<211> LENGTH: 25
<212> TYPE: DNA
<213> ORGANISM: Artificial
<220> FEATURE:
<223> OTHER INFORMATION: ACTB (beta actin) primer BAF

<400> SEQUENCE: 3
cagcggaacc gctcattgcc aatgg                                               25

<210> SEQ ID NO 4
<211> LENGTH: 25
<212> TYPE: DNA
<213> ORGANISM: Artificial
<220> FEATURE:
<223> OTHER INFORMATION: ACTB (beta actin) primer BAR

<400> SEQUENCE: 4
tcacccacac tgtgcccatc tacga                                               25

<210> SEQ ID NO 5
<211> LENGTH: 18
<212> TYPE: DNA
<213> ORGANISM: Artificial
<220> FEATURE:
<223> OTHER INFORMATION: ACTB (beta actin) primer BAFR

<400> SEQUENCE: 5
caggtcccgg ccagccag                                                       18

<210> SEQ ID NO 6
<211> LENGTH: 18
<212> TYPE: DNA
<213> ORGANISM: Artificial
<220> FEATURE:
<223> OTHER INFORMATION: C282Y (HFE gene, C282Y mutation) Probe C282YP

<400> SEQUENCE: 6
atatacgtgc caggtgga                                                       18

<210> SEQ ID NO 7
<211> LENGTH: 19
<212> TYPE: DNA
<213> ORGANISM: Artificial
<220> FEATURE:
<223> OTHER INFORMATION: C282Y (HFE gene, C282Y mutation) Primer C282YF

<400> SEQUENCE: 7

```
ctggataact tggctgtac                                                   19
```

<210> SEQ ID NO 8
<211> LENGTH: 19
<212> TYPE: DNA
<213> ORGANISM: Artificial
<220> FEATURE:
<223> OTHER INFORMATION: C282Y (HFE gene, C282Y mutation) Primer C282YR

<400> SEQUENCE: 8

```
tcagtcacat accccagat                                                   19
```

<210> SEQ ID NO 9
<211> LENGTH: 18
<212> TYPE: DNA
<213> ORGANISM: Artificial
<220> FEATURE:
<223> OTHER INFORMATION: H63D (HFE gene, H63F mutation) Probe H63DP

<400> SEQUENCE: 9

```
atatacgtgc caggtgga                                                    18
```

<210> SEQ ID NO 10
<211> LENGTH: 22
<212> TYPE: DNA
<213> ORGANISM: Artificial
<220> FEATURE:
<223> OTHER INFORMATION: H63D (HFE gene, H63F mutation) Primer H63DF

<400> SEQUENCE: 10

```
cttggtctttt ccttgtttga ag                                              22
```

<210> SEQ ID NO 11
<211> LENGTH: 22
<212> TYPE: DNA
<213> ORGANISM: Artificial
<220> FEATURE:
<223> OTHER INFORMATION: H63D (HFE gene, H63F mutation) Probe H63DR

<400> SEQUENCE: 11

```
acatctggct tgaaattcta ct                                               22
```

<210> SEQ ID NO 12
<211> LENGTH: 23
<212> TYPE: DNA
<213> ORGANISM: Artificial
<220> FEATURE:
<223> OTHER INFORMATION: CFTR (cystic fibrosis transmembrane conductance
      regulator) Primer CFT01

<400> SEQUENCE: 12

```
aggcctagtt gtcttacagt cct                                              23
```

<210> SEQ ID NO 13
<211> LENGTH: 21
<212> TYPE: DNA
<213> ORGANISM: Artificial
<220> FEATURE:
<223> OTHER INFORMATION: CFTR (cystic fibrosis transmembrane conductance
      regulator) Primer CFT03

<400> SEQUENCE: 13

```
tgcccccctaa tttgttactt c                                               21
```

<210> SEQ ID NO 14

```
<211> LENGTH: 27
<212> TYPE: DNA
<213> ORGANISM: Artificial
<220> FEATURE:
<223> OTHER INFORMATION: G6PC (glucose-6-phosphatase) probe GSDPR

<400> SEQUENCE: 14
tgtggatgtg gctgaaagtt tctgaac                                          27

<210> SEQ ID NO 15
<211> LENGTH: 18
<212> TYPE: DNA
<213> ORGANISM: Artificial
<220> FEATURE:
<223> OTHER INFORMATION: G6PC (glucose-6-phosphatase) Primer GSDw

<400> SEQUENCE: 15
ccgatggcga agctgaac                                                    18

<210> SEQ ID NO 16
<211> LENGTH: 20
<212> TYPE: DNA
<213> ORGANISM: Artificial
<220> FEATURE:
<223> OTHER INFORMATION: G6PC (glucose-6-phosphatase) Primer GSDcom

<400> SEQUENCE: 16
tgctttcttc cactcaggca                                                  20

<210> SEQ ID NO 17
<211> LENGTH: 29
<212> TYPE: DNA
<213> ORGANISM: Artificial
<220> FEATURE:
<223> OTHER INFORMATION: ACADM (medium chain acyl-CoA dehydrogenase)
      Probe MC11PR

<400> SEQUENCE: 17
ctagaatgag ttaccagaga gcagcttgg                                        29

<210> SEQ ID NO 18
<211> LENGTH: 20
<212> TYPE: DNA
<213> ORGANISM: Artificial
<220> FEATURE:
<223> OTHER INFORMATION: ACADM (medium chain acyl-CoA dehydrogenase)
      Primer MC11w

<400> SEQUENCE: 18
gctggctgaa atggcaatga                                                  20

<210> SEQ ID NO 19
<211> LENGTH: 25
<212> TYPE: DNA
<213> ORGANISM: Artificial
<220> FEATURE:
<223> OTHER INFORMATION: ACADM (medium chain acyl-CoA dehydrogenase)
      Primer MC11com

<400> SEQUENCE: 19
ctgcacagca tcagtagcta actga                                            25

<210> SEQ ID NO 20
<211> LENGTH: 43
<212> TYPE: DNA
<213> ORGANISM: Artificial
<220> FEATURE:
```

```
<223> OTHER INFORMATION: Hairpin oligonucleotide reHP
<220> FEATURE:
<221> NAME/KEY: misc_feature
<222> LOCATION: (1)..(1)
<223> OTHER INFORMATION: C12 amino modified at the 5' end

<400> SEQUENCE: 20
cagaatacag caggtgctcg cccgggcgag cacctgtatt ctg                         43

<210> SEQ ID NO 21
<211> LENGTH: 40
<212> TYPE: DNA
<213> ORGANISM: Artificial
<220> FEATURE:
<223> OTHER INFORMATION: Single strand oligonucleotide reBAF
<220> FEATURE:
<221> NAME/KEY: misc_feature
<222> LOCATION: (1)..(1)
<223> OTHER INFORMATION: C12 amino modified at the 5' end

<400> SEQUENCE: 21
cagattacag caggttcacc cacactgtgc ccatctacga                             40
```

ASSAYS AND APPARATUS FOR DETECTING ELECTROCHEMICAL ACTIVE MARKERS IN AN ELECTRIC FIELD

RELATED APPLICATIONS

This application is a continuation of U.S. patent application Ser. No. 10/506,958 filed May 2, 2005, which is a national stage application filed under 35 U.S.C. § 371 of International Application No. PCT/GB2003/000613 filed Feb. 11, 2003, which claims priority to and the benefit of GB0205455.9 filed Mar. 7, 2002. The contents of each of these applications are incorporated herein by reference in their entireties.

JOINT RESEARCH AGREEMENT

The disclosures of this application for patent were made under a joint research agreement between inventors Helen Braven and Russell Keay and assignee Molecular Sensing PLC at the time the invention was made. The named inventors were under obligation to assign to Molecular Sensing PLC. Assignee Molecular Sensing PLC has assigned the property rights to Atlas Genetics Limited.

FIELD OF THE INVENTION

The invention relates to probes for the sequence-specific detection of nucleic acids and methods associated therewith. The invention also relates to probes for the detection of nucleic acid binding proteins by virtue of their preferential binding to nucleic acids containing recognition sequences and methods associated therewith. More particularly the invention relates to labelled oligonucleotides suitable for use in the detection of nucleic acid and/or protein and methods associated therewith.

BACKGROUND OF THE INVENTION

The detection of specific DNA or RNA sequences is important for a wide range of applications within food, environmental and clinical diagnostics industries, and in the genomic, academic, pharmaceutical and pharmacogenetic research sectors. Detection methodologies should ideally be sensitive, sequence-specific, relatively rapid, low cost, accurate and suitable for routine use and/or automation. Furthermore they should ideally be capable of being integrated with existing DNA amplification methodologies for example the polymerase chain reaction (PCR) and other nucleic amplification methodologies.

In addition to nucleic acid detection methods based on or integrated with amplification techniques such as PCR, there are also known techniques for sequence specific nucleic acid detection which are based on specific binding of a probe to a target which need not necessarily have been previously amplified. Southern and Northern blotting are known examples of such techniques. Techniques that do not include an amplification stage must usually be highly sensitive in order to detect a signal. Typically autoradiography or chemiluminescence based techniques are used to produce the required sensitivity.

Southern and Northern blotting require the binding of the target nucleic acid to a membrane substrate. This requirement is disadvantageous because it is time consuming and poorly suited to automation.

Amplification-based DNA detection methods normally utilize a range of fluorescence chemistries or radioactive labels. Frequently, target DNA to be analysed is amplified enzymically e.g. by PCR, and then visualized using a fluorescent DNA binding dye to stain DNA size-separated by gel electrophoresis. Alternative methods that do not require gel electrophoresis have been developed. These frequently allow real-time detection of DNA amplification with non-sequence-specific fluorescent dyes e.g. SYBR Green or ethidium bromide. Assays have also been developed that integrate DNA amplification by PCR with fluorescence-based detection using an expanding variety of fluorescently labelled oligonucleotide probes that hybridise to specific DNA sequences. A number of assays have been developed that utilize the nuclease activity of a DNA polymerase. Examples of commercially available nuclease assays include Invader (trade mark—Third Wave Technologies), Readit (trade mark—Promega) and TaqMan (trade mark—Applied Biosystems). In TaqMan assays described for example in patents U.S. Pat. No. 5,487,972, U.S. Pat. No. 5,538,848 and U.S. Pat. No. 5,804,375 a hybridisation oligonucleotide is digested by the inherent 5' nuclease activity of Taq polymerase concomitant to primer extension by the polymerase activity of Taq.

The application of electrochemistry to DNA detection offers potential advantages over other detection systems in terms of sensitivity and simplicity. Their portability, robustness, ease of miniaturization and potential for high volume manufacturing makes apparatus for electrochemical methods especially suitable for clinical, food and environmental diagnostics.

The major focus for electrochemically-based gene probes has been on electrode-linked hybridisation techniques. Typically a capture probe (oligonucleotide or peptide nucleic acid) is immobilized on an electrode surface and it extracts the complementary target nucleic acid from a complex mixture of nucleic acids. The hybridisation event is transduced into a measurable electronic signal using either a redox-active hybridisation indicator (e.g. a ruthenium or cobalt salt), a redox-active indicator brought into contact with the target using a secondary probe, or by the direct measurement of changes in electrode capacitance caused by changes in the physical characteristics of the interface between the electrode and solution as a result of hybridisation. Frequently, these systems require prior amplification, e.g. by PCR, of the target sequence in order to achieve sufficient sensitivity.

Methods for detecting nucleic acid binding proteins include nuclease protection assays. In such assays a nucleic acid probe is mixed in solution with a putative nucleic acid binding protein. Under appropriate conditions nucleic acid binding proteins can be made to bind to the nucleic acid sequence present in the probe. Following putative binding any unbound probe or region of probe can be digested by a suitable nuclease. Bound nucleic acid probe will be protected from nuclease digestion because the bound protein will sterically hinder the nuclease. Digested and undigested nucleic acid probe are then separated, for example by gel filtration, gel-electrophoresis or by encouraging undigested nucleic acid to bind to a membrane or other substrate, and quantified. Typically the probe is labelled with a radioactive isotope in order that it and its breakdown products can be quantified. There are drawbacks to using radioisotopes including problems with radioactive decay reducing the shelf life of reagents and occupational health and environmental concerns.

Nucleic acid probes suitable for detecting nucleic acid binding proteins include nucleic acids substantially of the sequence known to bind nucleic binding proteins in vivo.

Additionally suitable probes for detecting nucleic acid binding proteins include aptamers which are nucleic acids evolved in vitro to perform a specific function (see for example Brody and Gold, Reviews in Molecular Biology 9 (1999) 324-329, Jäschke et al, Synlett 6 (1999) 825-833 and Griffith & Tawfik, Current Opinion in Biotechnology 11 (2000) 338-353 for details). Aptamers may be produced to bind to potentially any specific protein not just proteins ordinarily considered to be nucleic acid binding protein.

The use of the term "hybridise" in the context of nucleic acids in this specification will be understood to mean specific binding of a first nucleic acid to a second nucleic acid of complementary sequence. It will also be understood that in order for hybridisation to occur the complementarity of nucleic acid sequences is not required to be total. Hybridisation includes complementary binding that includes base mis-match to the extent that such mis-match shall not materially reduce the efficiency of the methods described.

The invention provides a method of probing for a nucleic acid comprising contacting a nucleic acid solution with an oligonucleotide probe labelled with an electrochemically active marker, providing conditions at which the probe is able to hybridise with any complementary (target) sequence which may be present in the nucleic acid solution, selectively degrading either hybridised or unhybridised nucleic acid probe, and electrochemically determining information relating to the electrochemically active marker. The information relating to the marker is expediently used to derive information concerning the presence or absence of at least one nucleic acid species. Preferably the electrochemical techniques are used to quantify relative proportions of degraded and non-degraded probe. As used herein, the term degrade includes degradation as a result of enzyme activity, for example by digestion.

A number of methods of selectively degrading either hybridised or unhybridised nucleic acid probe are available. These include enzymatic methods or chemical treatments. Enzymes may be used to degrade a nucleic acid probe by digestion that results in cleavage of a phosphor-ester bond or cleavage of a saccharide or glycosidic bond.

S1 nuclease isolated from *Aspergillus orzae* or another suitable source, or an enzyme having a similar specificity may be used to selectively digest unhybridised nucleic acid. The 5' nuclease activity of Taq polymerase or a similar enzyme may be used to digest a nucleic acid probe which has hybridised at a position on the target between a pair of PCR primers. In that case the probe would be digested concomitant to primer extension.

The Invader (trade mark) system of Third Wave Technologies Inc. (see U.S. Pat. No. 5,846,717, U.S. Pat. No. 5,837,450, U.S. Pat. No. 5,795,763 and U.S. Pat. No. 5,614,402) provides a fluorogenic nucleic acid detection system that may be adapted for use with an alternative embodiment of the electrochemical detection system of the present invention as illustrated in FIG. 14A. Briefly, two short oligonucleotide probes are allowed to hybridise with the target nucleic acid. The probes are so designed that, whilst both are able to hybridise for at least part of their length to form a nucleic acid duplex, there is a region of sequence overlap between the two probes. This produces a specific structure which is recognized by an enzyme which cleaves one of the probes to release a "5' flap" from the overlap region. A suitable enzyme is the flap endonuclease (FEN1) from *Archaeoglobus fulgidus*, sold under the Trademark "Cleavase VIII". An electrochemically active marker may be linked to the primer which yields the 5' flap, preferably at or towards the 5' end of that primer. The presence of the 5' flap in the reaction mixture may be detected by electrochemical techniques. Particularly, the electrochemically labelled 5' flap may be discriminated from the electrochemically labelled primer by virtue of the different length oligonucleotide portion of each respective molecule.

Alternatively and as illustrated in FIG. 14B, the 5' flap is not required to be linked to an electrochemically active marker. The release of the 5' flap is detected by an oligonucleotide recognition cassette which forms a nucleic acid triplex region which is also recognised and cleaved by cleavase enzyme. An electrochemically active marker may be linked to the recognition cassette so that cleavage of the recognition cassette results in the electrochemically active marker being linked to a fragment of the recognition cassette as opposed to the full length recognition cassette. The electrochemically labelled recognition cassette fragment may be discriminated from the electrochemically labelled full length recognition cassette by virtue of the different length oligonucleotide portion of each respective molecule.

The present invention is based on the observation that an electrochemically active marker such as metallocene exhibits different electrochemical characteristics depending on whether or not it is attached to a nucleotide, whether or not that nucleotide is incorporated into oligonucleotide or not, and the length of any such oligonucleotide.

The size and characteristics of a molecule to which an electrochemically active marker is attached may influence the perceived characteristics of the electrochemical marker for example, by influencing its rate of migration by diffusion or in response to an electric field.

The electrochemical activity of a marker may also be influenced by steric effects resulting from the presence of the molecule to which it is linked. For example, steric hindrance may prevent the marker from approaching an electrode and accepting or donating electrons.

If the marker is attached to an oligonucleotide then the secondary structure of the oligonucleotide (as largely determined by primary sequence) may influence the physical properties of that marker. For example, if the marker is attached to an oligonucleotide that contains self-complementary primary sequence then the resultant stem and loop secondary structure may sterically hinder the electrochemically active marker and reduce the signal obtained by voltammetry. It will be understood that digestion of the oligonucleotide may destroy or release the stem and loop structure and reduce or abolish its influence on the marker.

It will also be apparent that because the secondary structure of oligonucleotides is dependent on temperature, the effects which an oligonucleotide has on an electrochemically active marker vary with temperature.

A person skilled in the art is able to select an appropriate temperature at which to carry out the electrochemical technique of the invention in order to achieve an optimum signal to background noise ratio for the technique. If the technique is incorporated into a PCR reaction or other technique for which a thermal cycling apparatus is used, measurement at a desired temperature may simply be made at an appropriate point in the PCR temperature regime.

In one form of the method according to the invention 5' nuclease digestion of the probe labelled with an electrochemically active marker takes place concomitant to PCR primer extension. It will be apparent that such method includes a real time PCR method in which the electrochemical activity of the solution is automatically measured during or following each PCR cycle. The more target that is present in the sample the more primer extension and probe digestion is likely to take place. The accumulated digested probe will be distinguished from undigested probe due to its different electrochemical activity. As discussed above, the temperature (PCR phase) at which measurements are made may influence the quality of signal obtained.

For simplicity, the present invention has largely been described in terms of detecting a single nucleic acid species. It will, however, be appreciated that the invention includes a "multiplex" system by which the methods and apparatus disclosed may be used to detect more than one nucleic acid species simultaneously. Multiplex systems have the general advantages that they enable control experiments to be carried out simultaneously and under the same conditions as a test experiment or that they enable several analyses to be carried out simultaneously and under the same conditions. The use of multiplex systems thus brings about savings of reagents and time. An example of such a multiplex system is the use of oligonucleotide probes which are complementary to two or more different targets. Those probes might be distinguished from each other by being labelled with electrochemically active markers having different redox characteristics and therefore being separately identifiable by any suitable electrochemical technique for example, differential pulse voltammetry In order to be suitable for use in a multiplex experiment, two (or more) markers should have redox characteristics that are sufficiently different from each other to enable the two (or more) markers to be analysed in a resolvable fashion. For example, if differential pulse voltammetry is to be used, the voltammogram traces for the two (or more) markers should have peaks at voltages that are resolvable from each other. Preferably two different markers are used. The invention provides novel electrochemical markers, which may be used in a multiplex system. The provision of novel markers increases the range of markers available and therefore makes the development of multiplex systems feasible.

The labelled oligonucleotides used in accordance with a first aspect of the invention are capable of producing a distinct or enhanced electrochemical signal due to the release of ferrocenylated mononucleotide, dinucleotide or oligonucleotide from a hybridisation oligonucleotide in a sequence-dependent nuclease assay. Those assays depend on a nuclease activity to cause a change to the probe such that a novel or enhanced signal is produced on recognition of a specific nucleic acid sequence.

If desired, the electrochemical detection step may be carried out using one or more electrodes covered by a membrane which is able selectively to exclude molecules based on one or more characteristics, for example, characteristics selected from size, charge and hydrophobicity. That may assist in eliminating background current arising from, for example, charged nucleic acid or undigested labelled oligonucleotide.

Suitable electrochemically active markers include those comprising metallo-carbocyclic pi complexes, that is organic complexes with partially or fully delocalised pi electrons. Suitable markers include those comprising sandwich compounds in which two carbocyclic rings are parallel, and also bent sandwiches (angular compounds) and mono-cyclopentadienyls. Preferably, the electrochemically active markers are metallocenyl labels. More preferably they are ferrocenyl labels.

Ferrocenyl and metallocenyl labels used in the probes according to the invention may advantageously be N-substituted ferrocene or metallocene carboxamides. The ferrocene or metallocene ring, which constitutes the labelling moiety, may be unsubstituted. If desired, the ferrocene or metallocene ring may be substituted by one or more substituents, the nature and location of which are selected so as to influence in a desired manner the redox characteristics of the ferrocene or metallocene moiety. The ferrocene or metallocene ring may additionally or instead be substituted by any ring substituents that do not materially reduce the electrochemical sensitivity of the label. The ferrocene or metallocene carboxamide moiety may be linked via the carboxamide nitrogen to the nucleotide or oligonucleotide. Linkage to the nucleotide or oligonucleotide is preferably via a phosphate group or via the base of the nucleotide. Both methods of linkage permit the label to be attached via any nucleotide along the length of the oligonucleotide. However if linkage is via a phosphate group it is advantageously via a 3' or 5' terminal phosphate group so as to minimise the likelihood that such linkage will sterically hinder Watson-Crick hybridisation of the oligonucleotide or affect nuclease activity. Linkage via a region of the base not involved in Watson-Crick base pairing is predicted to be less disruptive of such base pairing. Therefore linkage via the base may be more suitable for labelling at non-terminal oligonucleotide sites. The label oligonucleotide may have a linker moiety between the oligonucleotide and the labelling moiety. Preferably, the labelled oligonucleotides have a ferrocenyl labelling moiety which is linked to the oligonucleotide by a linker moiety.

There may be used any suitable linker moiety. Suitable linker moieties may comprise an aliphatic chain which may be linear or branched, and saturated or unsaturated. Advantageously, the linker moiety is a linear or branched aliphatic chain having from 4 to 20 carbon atoms, and preferably from 6 to 16, especially from 8 to 14 atoms, especially 12 carbon atoms. The alkylene chains may be substituted by any substituent or may be interrupted by any atom or moiety provided that any such substituent, atom or moiety does not materially reduce the electrochemical sensitivity of the label. Illustrative of the ferrocenyl labels which may be used in accordance with the invention are those in Formulae I to III. Molecules of formula Ia to IIIa are oligonucleotides labelled with the corresponding ferrocenyl labels. Formula IV is illustrative of a ferrocenyl label which may be attached via a nucleotide base, the amino-modified thymine base being included in Formula IV for the purposes of illustration.

I

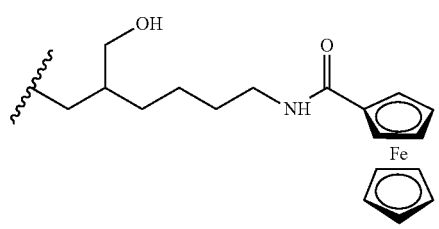

Ia
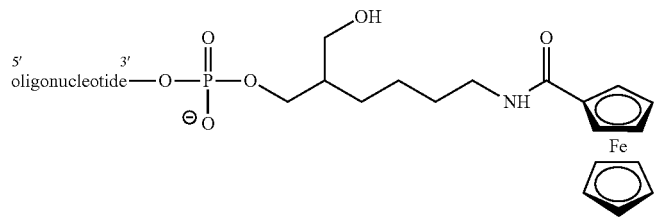
II
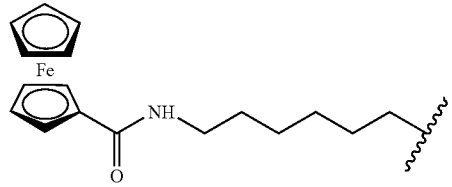
IIa
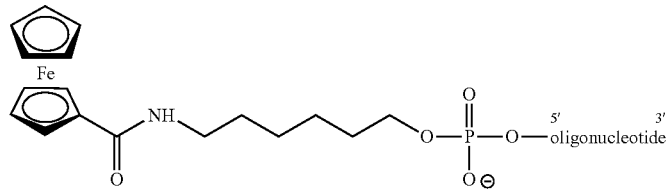
III
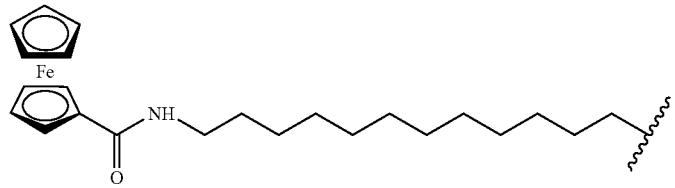
IIIa
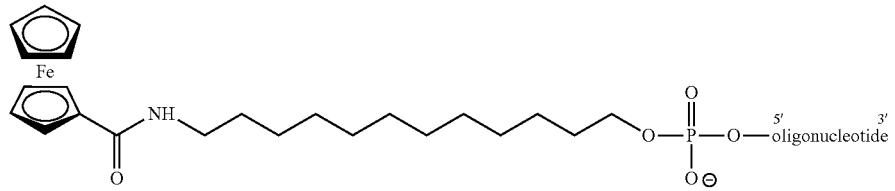
IV
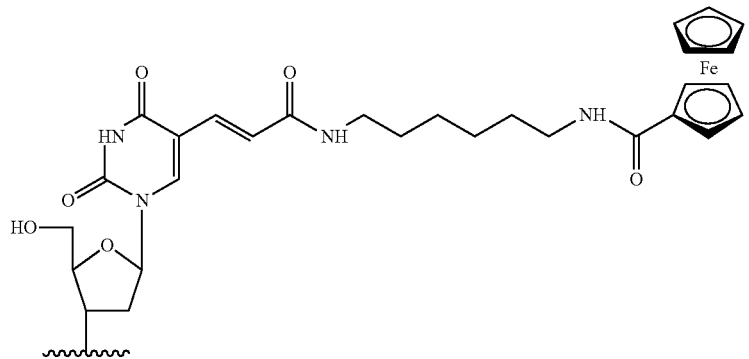

-continued

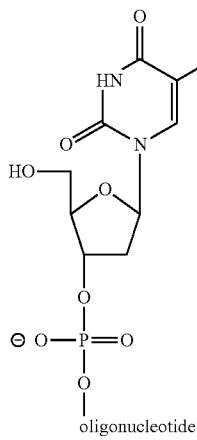

IVa

The ferrocene labelled probes may be made by any suitable method. By way of example, the oligonucleotide may be an oligonucleotide modified by introduction of a radical having a terminal amino group. Illustrative of such amino-modified nucleotides is the modified nucleotide of Formula V. The ferrocene may then be incorporated by reaction of the amino-modified nucleotide with the N-hydroxy-succinimide ester of ferrocene carboxylic acid (Formula VI) to obtain ferrocene labelled oligonucleotide.

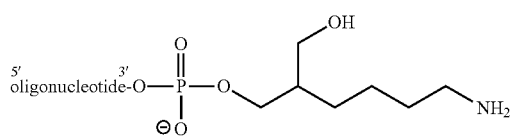

V

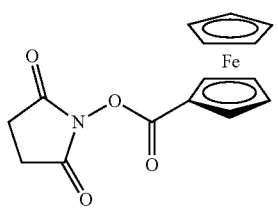

VI

In an alternative method, ferrocene labelled oligonucleotides may be prepared by addition of the ferrocene moiety during solid phase oligonucleotide synthesis. Ferrocene labels can be introduced into an oligonucleotide during solid phase synthesis by two general methods: Firstly, addition of the oligonucleotide at the 3' end of the oligonucleotide requires the use of a suitable resin. Such a resin is labelled with a ferrocene derivative. Addition of ferrocene at an internal site, or at the 5'end of an oligonucleotide requires the use of a coupling reagent suitable for coupling with a solid support bound oligonucleotide, for example a ferrocenyl derivative phosphoramidite, for example as shown as formula IX or X.

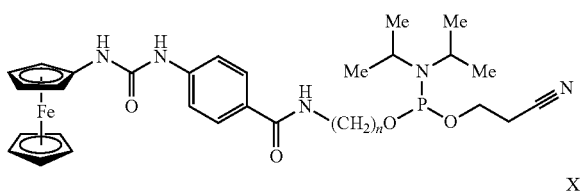

IX

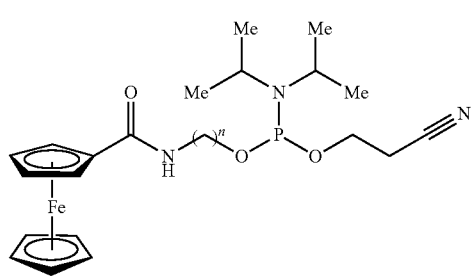

X

The invention also provides a novel alternative electrochemically active marker, label or labelled moiety. The invention provides a compound of formula XI, Mc-NR'—C(=O)—X—(Ar)$_n$-(L)$_m$-R     XI Wherein Mc is a metallocenyl group in which each ring may independently be substituted or unsubstituted, the metallocenyl group comprises a metal ion M selected from the group consisting of iron, chromium, cobalt, osmium, ruthenium, nickel or titanium, R' is H or lower alkyl, X is either NR' or O, Ar is a substituted or unsubstituted aryl group, n is 0 or 1, L is a linker group, m is 0 or 1, and R represents a moiety to be labelled or R is a moiety comprising a leaving group.

The Mc group may be substituted by one or more groups selected lower alkyl (for example $C_1$ to $C_4$ alkyl), lower alkyl substituted with a hydroxy, halo, cyano, oxo, amino, ester amido or a further metallocene group, lower alkenyl, lower alkenyl substituted with a hydroxy, halo, cyano, oxo, amino, ester, amido or a further metallocene group, aryl, aryl substituted with a hydroxy, halo, cyano, oxo, amino, ester, amido or a further metallocene group. The further metallocene group may be substituted in the same way as the Mc group with the exception that the total number Mc groups in the molecule of the invention preferably does not exceed four. Preferably, the Mc group is unsubstituted.

Preferably, M is an ion selected from iron, osmium or ruthenium. Most preferably, M is an iron ion. When M is an iron ion, Mc is a ferrocene.

Lower alkyl is preferably C1 to C4 alkyl. Preferably, R' is H. Each R' has an identity separate from the other R'.

Preferably X is NH.

The Ar group may be substituted by one or more groups selected lower alkyl (for example $C_1$ to $C_4$ alkyl), lower alkyl substituted with a hydroxy, halo, cyano, oxo, amino, ester or amido group, lower alkenyl, lower alkenyl substituted with a hydroxy, halo, cyano, oxo, amino, ester or amido group, aryl or aryl substituted with a hydroxy, halo, cyano, oxo, amino, ester or amido group, preferably, the Ar group is unsubstituted.

Preferably, n=1. Preferably, m=1.

Suitable linker groups L may comprise an aliphatic chain which may be linear or branched, and saturated or unsaturated. Advantageously, the linker moiety is a linear or branched aliphatic chain having from 4 to 20 carbon atoms, and preferably from 6 to 16, especially from 8 to 14 atoms, more especially 12 carbon atoms. The alkylene chains may be substituted by any substituent or may be interrupted by any atom or moiety provided that any such substituent, atom or moiety does not materially reduce the electrochemical sensitivity of the label.

The compound of the invention may comprise more than one metallocene groups. In the compound of the invention, the metallocene group may be substituted by any other electrochemically active marker group. The compound may be one which is electrochemically active or becomes electrochemically active following partial cleavage.

Preferably, the moiety to be labelled is an amino acid, a nucleotide, an oligonucleotide, a polynucleotide, a nucleoside, a sugar, a carbohydrate, a peptide, a protein or a derivative of any of those molecules. In a preferred embodiment, R is a nucleotide or an oligonucleotide. The nucleotide may be selected from adenosine, thymidine, guanosine, cytidine or uridine. Preferably the nucleotide is attached through a group attached to the ribose or deoxyribose group of the nucleotide, for example in the 2', 3' or 5' position. Most preferably, the nucleotide is attached at the 3' or 5' position, for example at the 5'position. Preferably, the attachment at the 2', 3' or 5' position is through an oxygen or a nitrogen atom.

In a further preferred embodiment, R is a group comprising a leaving group, preferably an alkyl or a carbonyl group comprising a leaving group. Amongst alkyl groups there are preferred lower alkyl groups (for example $C_1$ to $C_4$ alkyl groups) Amongst leaving groups, there may be mentioned hydroxyl, halides, organic acids and N-hydroxy diacylamines. The leaving group may, for example be chloride, bromide or iodide, acetic acid, a benzoic acid, 2,6 dichlorobenzoic acid, an N-hydroxysuccinamide, a maleimide, iodoacetamide or isothiocyanate. Preferably the leaving group is N-hydroxysuccinamide. The leaving group may be an activatable group suitable for use in a reaction for coupling to a solid-support bound moiety. For example, the leaving group may be a phosphoramidite group.

When R is a group comprising a leaving group the compound is a labeling reagent which may be used to electrochemically label another molecule. The labeling reagent is particularly useful for labeling biologically important molecules for use in either known methods or methods of the invention. Molecules of interest that may be labelled include, but are not limited to—amino acids, nucleotides, nucleosides, sugars, peptides, proteins, oligonucleotides, polynucleotides, carbohydrates and derivatives of any of those molecules.

The labeling reagent may be attached directly or via a linker. The linker may be attached first to the labeling reagent or to the molecule to be labelled. If the linker is first attached to the molecule to be labelled it may comprise a group, for example, an amino or a thiol group, that will assist in the labeling reaction. An amino group is preferred.

If the molecule to be labelled is a nucleotide or an oligonucleotide the labeling is preferably to the 3' or 5' end. The oligonucleotide may be amino-modified to assist with the labeling reaction. Amino-modified oligonucleotides may be synthesized by standard techniques and are available from a wide range of commercial sources for example from Oswel Scientific (Southampton, UK). The amino-modified oligonucleotide may also incorporate a linker motif, for example, the modification may be the addition of 5' aminohexyl or 3' aminohexyl or a 5'-C12 amino-group. A labelled molecule of interest preferably comprises a linker.

In the case of an oligonucleotide, the sequence of the oligonucleotide portion of the molecule is preferably such that the molecule is able to hybridize with a complementary target sequence and thus be used as a probe in a molecular biological technique, for example, one of the nucleic acid detection or qualification techniques disclosed in this specification.

Labelled biological molecules in accordance with the invention may be electrochemically active in either digested or non-digested states. Ideally the extent of electrochemical activity will vary in dependence on the extent of digestion.

Formula VIII illustrates a possible mode of attachment of the novel electrochemically active marker to an oligonucleotide. The molecule of formula VIII may be obtained by reacting a 5'-aminohexyl modified oligonucleotide with the molecule shown in formula VII.

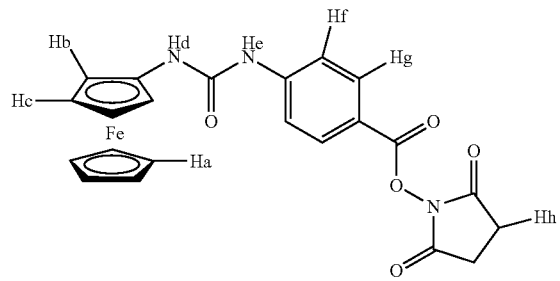

VII

-continued

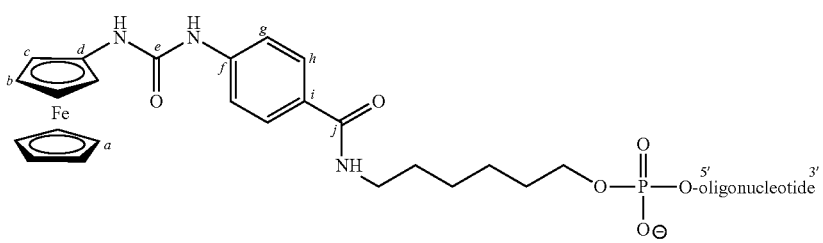

VIII

Details of N-hydroxysuccinimide ester of 4-(3'-ferrocenylureido)-1-benzoic acid and details of the use of said compound to label oligonucleotides are provided in Examples 7 and 8. It will however be apparent to the skilled person that such a label may be attached to an oligonucleotide at any suitable position and that attachment is not limited to the 5' end of said oligonucleotide. It will also be apparent that attachment of the novel marker need not be via an aminohexyl linker nor need the marker be attached necessarily to an oligonucleotide. There is potential for the novel marker to be used to label other molecules of interest, especially molecules of biological interest such as proteins, carbohydrates and antibodies.

Molecules in accordance with the invention have particular utility in methods according to the invention. Under the conditions set out in table 3, the electrode potential of substituted ferrocene carboxylic acids have an electrode potential in the region of 400 mV. On the other hand, substituted metallocene molecules in accordance with the invention have an electrode potential in the region of 150 mV. The lower potential is a potential at which the propensity for background impurities to interfere with data collection is much lower. Accordingly, the molecules of the invention enable more sensitive readings to be taken. Voltammograms illustrating the different electrode potentials of a conventional ferrocene derivative (ferrocene carboxylic acid XII) are shown in FIGS. 23A and 23B. 4-(3'-ferrocenylureido)-1-benzoic acid, a ferrocene derivative with a ferrocene moiety as found in molecules of the invention is shown in FIGS. 23C and 23D. As is seen from a comparison of FIGS. 23B and 23D the peak for the ferrocene derivative with a ferrocene moiety as found in molecules of the invention comes at a part of the scanning voltammogram at which the background signal is weak, thus enabling a more sensitive detection of that molecule.

The invention also provides apparatus arranged to carry out any one or more of the methods disclosed herein. Such apparatus may include suitable electrodes, electrochemical cells, disposable plastic ware and apparatus for detecting, recording, manipulating and displaying results, and in the case of PCR methods, appropriately programmed or programmable thermal cyclers. Such apparatus may also include apparatus for the optimal design of primers, probes and cycling conditions.

The invention provides apparatus comprising one or more sample receiving regions for receiving one or more samples, means for controlling the temperature of said sample receiving regions and means for measuring the electrochemical properties of said sample. According to one embodiment of the invention, there is provided a thermal cycler, which may use conventional means to control sample temperature but into which has been integrated a means for making electrochemical measurements of the samples. Such an apparatus may be manufactured so as to utilize conventional electrode cells (for example those used in examples herein).

The present invention further provides a container comprising one or more sample receiving regions for holding one or more samples. Such a container may be based on the design of polypropylene tubes or 96-well plates as presently used in PCR. Ideally such a container will be adapted to receive at least one electrode component. That electrode component might, for example, be located as part of a lid for the container so that when it is used to close the container, the electrode component(s) reach into the sample solution. Such a container will have advantages over conventional electrochemical cells which have not been designed to be used in thermal cyclers and so may not have the optimum thermal conductivity characteristics. Also conventional electrochemical cells are generally not regarded as disposable because of their relatively high cost. The use of disposable plastic ware has become standard practice in molecular biology because it mitigates the risks of sample contamination.

Alternatively, the invention provides a container, optionally based on known designs of polypropylene PCR tubes or 96-well plates, into which one or more electrode component for use in the methods of the invention have been integrated. Such a container is preferably producible in sufficiently high quantities to enable the cost of the component to be reduced to a point where it might be regarded as disposable.

Certain illustrative embodiments of the invention will now be described in detail with reference to the accompanying drawings in which.

Figure 24A:
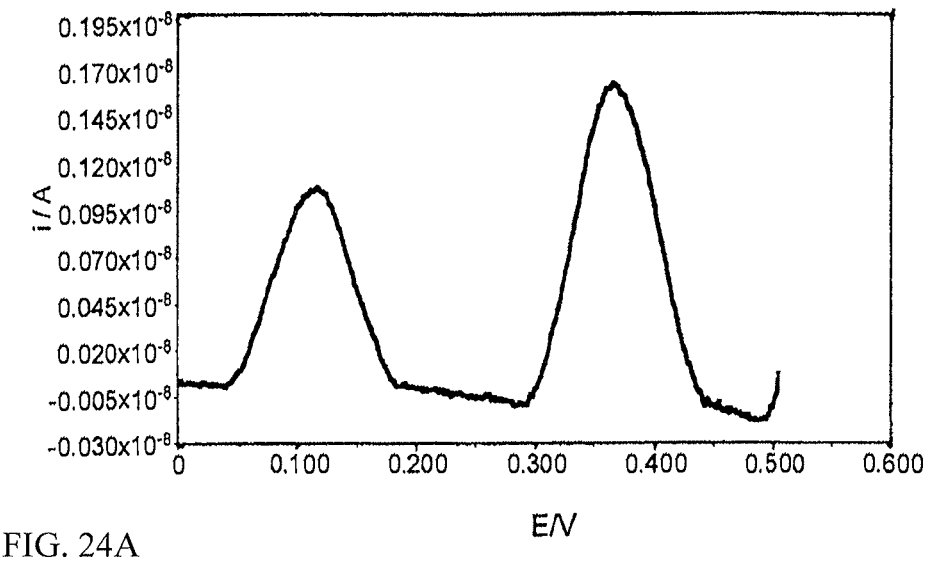
Figure 24B:
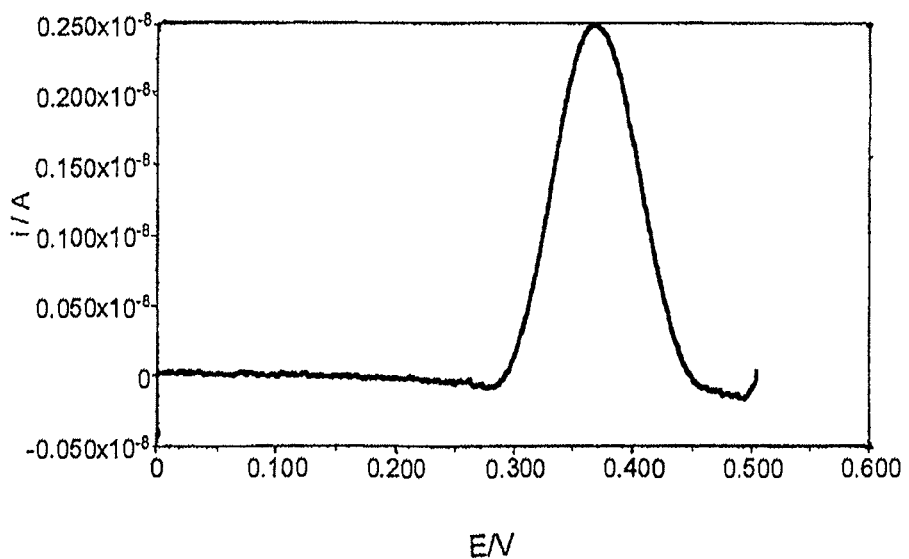
Figure 24C:
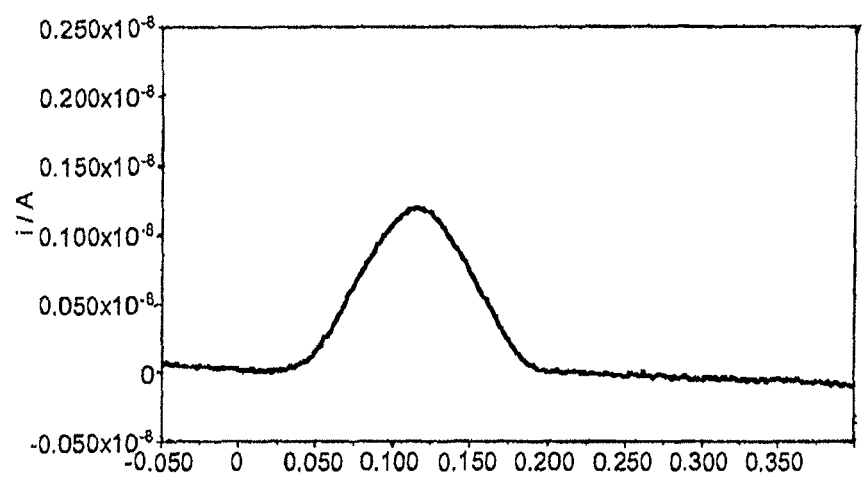

FIGS. 24A, 24B and 24C show differential pulse voltammograms of the products of nuclease digest reactions in which the BAPR oligonucleotide was labelled at the 5' end by ferrocene with a 12 carbon spacer moiety (2.5 µM) and MC11w oligonucleotide was labelled at the 5' end by 4-(3-ferrocenylureido)-1-benzoic acid with a 12 carbon spacer moiety (1.5 µM) (FIG. 24A), BAPR oligonucleotide was labelled at the 5' end by ferrocene with a 12 carbon spacer moiety only (2.5 µM) (FIG. 24B), and MC11w oligonucleotide was labelled at the 5' end by 4-(3-ferrocenylureido)-1-benzoic acid with a 12 carbon spacer moiety only (1.5 µM) (FIG. 24C).

Figure 1:
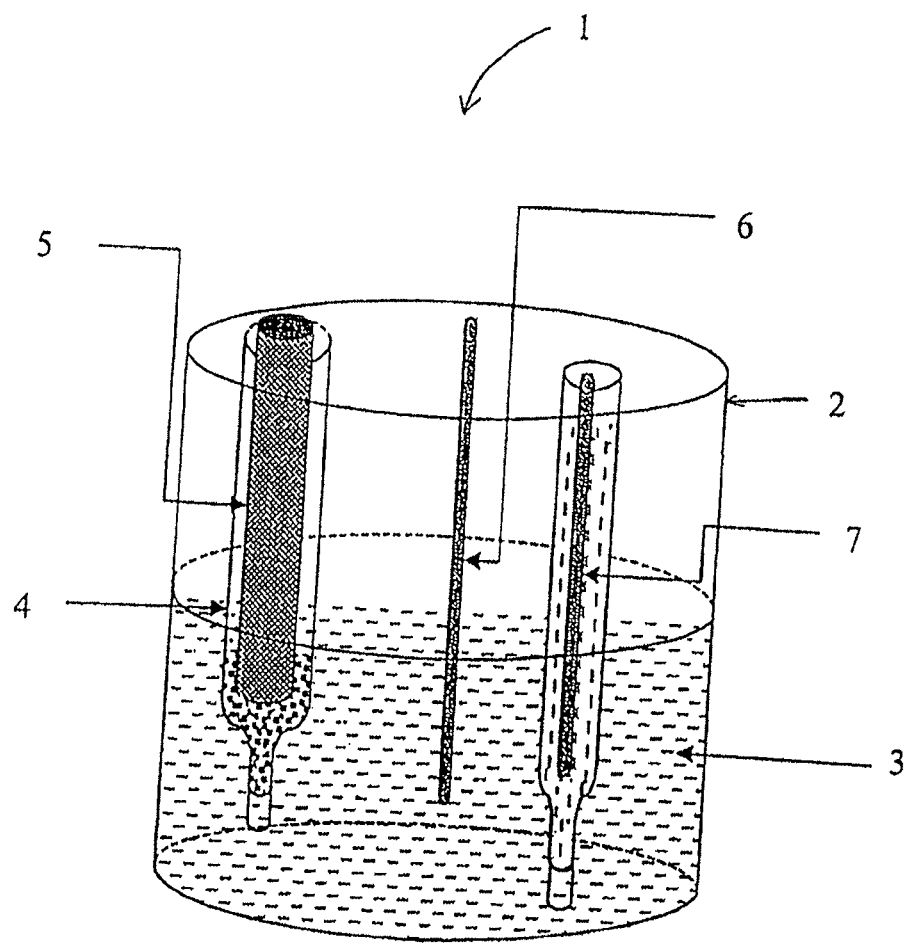
FIG. 1 is a schematic representation of an electrochemical cell used in differential pulse voltammetry measurements described herein.

With reference to FIG. 1, an electrochemical cell 1 suitable for use in the cyclic voltammetry experiments described herein comprises a vessel 2, containing a background electrolyte solution 3, which is an aqueous 100 mM solution of ammonium acetate. Immersed in the solution 3 is a chamber 4, which receives both the sample to be tested and, immersed therein, a glassy carbon working electrode 5. A gold electrode may alternatively be used. Also immersed in the solution 3 is a counter-electrode 6 of platinum wire and a silver/silver chloride reference electrode 7 immersed in 4M potassium chloride solution, which solutions are in communication with others via a sintered disc.

Figure 15A:
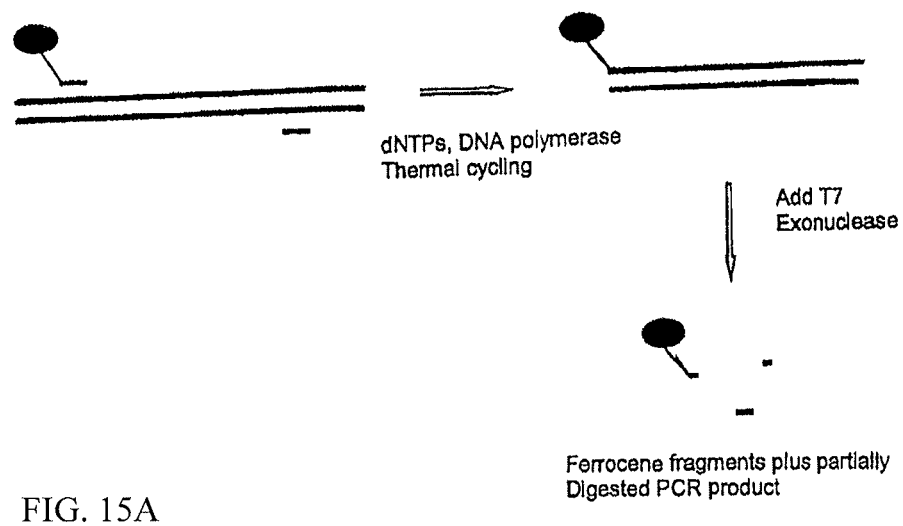
FIG. 15A illustrates the use of the methods of the invention in a T7 exonuclease assay.
Figure 15B:
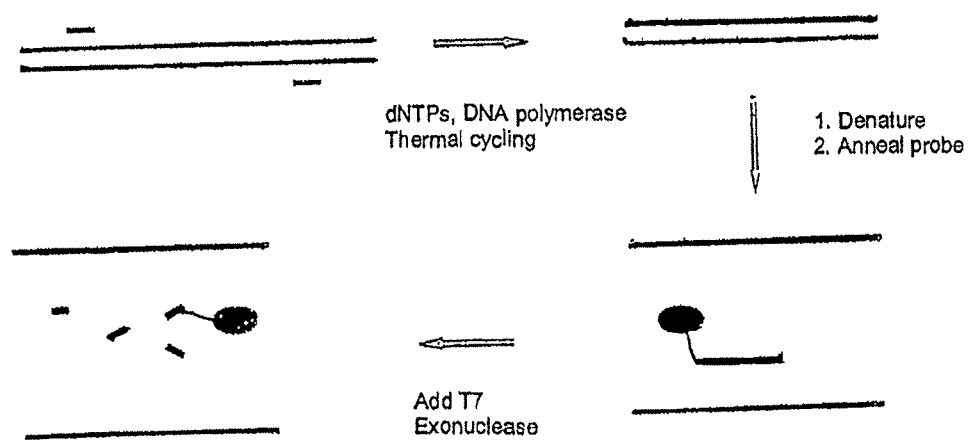
FIG. 15B illustrates the use of the methods of the invention in an assay incorporating a T7 exonuclease digestion of a labelled oligonucleotide probe annealed to PCR products.

With reference to FIG. 15A and FIG. 15B, T7 exonuclease (sometimes referred to as T7 gene 6 exonuclease) is a duplex specific 5' to 3' exonuclease. The enzyme digests oligonucleotides annealed to a target region of DNA in order to produce mononucleotide, dinucleotide and shorter oligonucleotide fragments. The substrate specificity of the enzyme is such that oligonucleotide probes labelled with an electrochemical marker such as ferrocene at the 5' end can be digested. Digested ferrocene labelled probes can be detected by electrochemical methods, for example by differential pulse voltammetry. T7 exonuclease is not thermostable, and therefore is not stable under the thermal cycling conditions normally used in PCR.

T7 exonuclease can be used in PCR based DNA detection in two ways. PCR products labelled at the 5' end with a marker such as ferrocene can be synthesized by using a 5' labelled primer. The T7 exonuclease subsequently added to the PCR mix digests the labelled PCR product. Non-amplified single strand primer will not be digested (FIG. 15A). In the second method, in order to provide sequence specific PCR product detection, an electrochemically labelled probe similar to a Taqman probe (Trade Mark—Applied Biosystems) in that it is designed to hybridized to the target nucleic acid between the primer sequences, is used instead of labelled primers. The probe is introduced into the PCR mix after thermal cycling and allowed to anneal to the target. T7 exonuclease is then added and the probe is digested only if it has formed a duplex by annealing with a complimentary PCR product.

The following Examples illustrate the invention:

Materials and Methods—Oligonucleotide Preparation and Assays

Oligonucleotides were obtained from Sigma Gensosys. All oligonucleotides were obtained desalted and were used without further purification. N,N'-Dimethylformamide (DMF) (99.8% A.C.S. reagent) and zinc acetate dihydrate (99.999%) were obtained from Aldrich.

Potassium bicarbonate (A.C.S. reagent), potassium carbonate (minimum 99%), ammonium acetate (approximately 98%), magnesium acetate (minimum 99%), ammonium persulfate (electrophoresis reagent), N,N,N',N'-tetramethylethylenediamine (TEMED) and molecular biology grade water were obtained from Sigma.

NAP10 columns (G25 DNA grade Sephadex trade mark) were obtained from Amersham Biosciences.

S1 Nuclease, dNTPs and human genomic DNA were obtained from Promega.

AmpliTaq Gold, with 25 mM magnesium chloride and GeneAmp (trade mark) 10×PCR Gold buffer supplied and Amplitaq DNA Polymerase, Stoffel Fragment, with 10× Stoffel buffer and 25 mM magnesium chloride supplied, was obtained from Applied Biosystems.

T7 exonuclease was obtained from New England Biolabs.

Incubations were performed using a PTC-100 Programmable Thermal Controller (MJ Research Inc.). Absorbance measurements at 260 nm were performed using a Cary 100 Bio spectrophotometer (Varian Ltd.).

Polyacrylamide gels were prepared with PratoGel (National Diagnostics) and stained with SYBR Gold (Molecular Probes Inc.).

Agarose gels were prepared with SeaKem LE agarose (BioWhittaker Molecular Applications) and stained with ethidium bromide (Aldrich). Gels were electrophoresed in 0.5× Tris/borate/EDTA (TBE) buffer (Sigma). All solutions were prepared with autoclaved deionised water (WaterPro system, Labconco).

Oligonucleotide Sequences

The oligonucleotide sequences of the glucose-6-phosphatase and medium chain acyl-CoA dehydrogenase primers and probes were as disclosed in Kunihior Fujii, Yoichi Matsubara, Jun Akanuma, Kazutoshi Takahashi, Shigeo Kure, Yoichi Suzuki, Masue Imiazurni, Kazuie Iinuma, Osamu Sakatsume, Piero Rinaldo, Kuniaki Narisawa; Human Mutation; 15; 189-196; (2000).

The oligonucleotide sequence of the beta actin primers and probe were as disclosed in Agnetha M Josefsson, Patrik K E Magnusson, Nathelie Ylitalo, Per Sorensn, Pernialla Qwarforth-Tubbin, PerKragh Andersen, Mads Melbye, Hans-Olov Adami, Ulf B Gyllensten; Lancet; 355; 2189-2193; (2000).

The oligonucleotide sequence of the HFE gene primers and probe were as disclosed in Luis A. Ugozzoli, David Chinn, Keith Hamby, Analytical Biochemistry; 307; 47-53 (2002).

```
ACTB (β actin)
Probe
                                              (SEQ ID NO: 1)
BAPR: ATG CCC TCC CCC ATG CCA TCC TGC GT (SEQ ID NO: 2)
C9-T1BAPR: T(C9)G CCC TCC CCC ATG CCA TCC TGC GT
(T(C9) = amino modified thymine with C9 linker,
Formula IV)

Primers
                                              (SEQ ID NO: 3)
BAF: CAG CGG AAC CGC TCA TTG CCA ATG G (SEQ ID NO: 4)
BAR: TCA CCC ACA CTG TGC CCA TCT ACG A (SEQ ID NO: 5)
BAFR: CAG GTC CCG GCC AGC CAG C282Y (HFE gene, C282Y mutation)
Probe
                                              (SEQ ID NO: 6)
C282YP: ATA TAC GTG CCA GGT GGA Primers
                                              (SEQ ID NO: 7)
C282YF: CTG GAT AAC TTG GCT GTA C (SEQ ID NO: 8)
C282YR: TCA GTC ACA TAC CCC AGA T H63D (HFE gene, H63F mutation)
Probe
                                              (SEQ ID NO: 9)
H63DP: ATA TAC GTG CCA GGT GGA Primers
                                              (SEQ ID NO: 10)
H63DF: CTT GGT CTT TCC TTG TTT GAA G (SEQ ID NO: 11)
H63DR: ACA TCT GGC TTG AAA TTC TAC T CFTR (cystic fibrosis transmembrane conductance
regulator)
Primers
                                              (SEQ ID NO: 12)
CFT01: AGG CCT AGT TGT CTT ACA GTC CT (SEQ ID NO: 13)
CFT03: TGC CCC CTA ATT TGT TAC TTC G6PC (glucose-6-phosphatase)
Probe
                                              (SEQ ID NO: 14)
GSDPR: TGT GGA TGT GGC TGA AAG TTT CTG AAC Primers
                                              (SEQ ID NO: 15)
GSDw: CCG ATG GCG AAG CTG AAC (SEQ ID NO: 16)
GSDcom: TGC TTT CTT CCA CTC AGG CA ACADM (medium chain acyl-CoA dehydrogenase)
Probe
                                              (SEQ ID NO: 17)
MC11PR: CTA GAA TGA GTT ACC AGA GAG CAG CTT GG Primers
                                              (SEQ ID NO: 18)
MC11w: GCT GGC TGA AAT GGC AAT GA (SEQ ID NO: 19)
MC11com: CTG CAC AGC ATC AGT AGC TAA CTG A Hairpin oligonucleotide
                                              (SEQ ID NO: 20)
reHP: CAG AAT ACA GCA GGT GCT CGC CCG GGC GAG CAC
CTG TAT TCT G Single strand oligonucleotide
                                              (SEQ ID NO: 21)
reBAF: CAG AAT ACA GCA GGT TCA CCC ACA CTG TGC CCA
TCT ACG A
```

The oligonucleotide for use in examples 7 and 8 were C12 amino modified at the 5' end. The olignucleotides for use in the other examples were unmodified.

Materials and Methods—Electrochemical Detection

The following electrodes and low volume cell were obtained from BAS, Congleton, Cheshire, UK:

Glassy carbon working electrode (catalogue number MF-2012) was used in examples 4 and 5. A Gold working electrode (catalogue number MF-2014) was used in examples 8 to 10.

Silver/silver chloride reference electrode (catalogue number MF-2079)

Platinum wire counter (auxiliary) electrode (catalogue number MW-4130).

Low volume cell (catalogue number MF-2040) comprising glass voltammetry vial and glass sample chamber, with replaceable vycor tip.

An AutoLab electrochemical workstation (either PGSTAT30 with frequency response analyzer or μAutoLab type II manufactured by Eco Chernie B.V) was obtained from Windsor scientific Limited.

EXAMPLE 1

This Example describes the cyclic voltammetry method used in Examples 3 to 5 and 8 to 10 below.

The low volume cell of FIG. 1 was filled with approximately 10 ml ammonium acetate solution (100 mM).

A 200 μl aliquot of the sample for analysis was placed in the glass sample chamber 4 which was then placed in the low volume cell along with the reference 7 and counter electrodes 6. The electrodes were connected to an Autolab electrochemical workstation and differential pulse voltammetry carried out using the parameters described below. Prior to analysis the working electrode was polished (using BAS polishing kit catalogue number MF-2060) followed by conditioning. Electrode conditioning consisted of cyclic voltammetry, sweeping between +/−1 volt in the appropriate background buffer.

Parameters for Differential Pulse Voltammetry

TABLE 1

Parameters used in Examples 4 and 5

| Parameter: | Cathodic | Anodic Sweep |
|---|---|---|
| Conditioning potential (V) | 0 | 0 |
| Conditioning duration (s) | 0 | 0 |
| Deposition potential (V) | 0.8 | −0.1 |
| Deposition duration (s) | 5 | 5 |
| Equilibration time (s) | 0 | 0 |
| Modulation time (s) | 0.02 | 0.02 |
| Interval time (s) | 0.1 | 0.1 |
| Initial potential (V) | 0.75 | −0.1 |
| End potential (V) | 0.1 | 0.7 |
| Step potential (V) | 0.005 | 0.005 |
| Modulation amplitude (V) | 0.1 | 0.1 |

TABLE 2

Parameters used in Example 8

| Parameter: | Cathodic | Anodic Sweep |
|---|---|---|
| Conditioning potential (V) | 0 | 0 |
| Conditioning duration (s) | 0 | 0 |
| Deposition potential (V) | 0 | 0 |
| Deposition duration (s) | 0 | 5 |
| Equilibration time (s) | 0 | 0 |
| Modulation time (s) | 0.04 | 0.04 |
| Interval time (s) | 0.1 | 0.1 |
| Initial potential (V) | −0.1 | .0.3 |
| End potential (V) | 0.3 | −0.1 |
| Step potential (V) | 0.0003 | 0.0003 |
| Modulation amplitude (V) | 0.05 | 0.05 |

TABLE 3

Parameters used in Examples 9 and 10

| Parameter: | Anodic sweep |
|---|---|
| Conditioning potential (V) | 0 |
| Conditioning duration (s) | 10 |
| Deposition potential (V) | 0 |
| Deposition duration (s) | 0 |
| Equilibration time (s) | 0 |
| Modulation time (s) | 0.04 |
| Interval time (s) | 0.1 |
| Initial potential (V) | −0.1 |
| End potential (V) | 0.7 |
| Step potential (V) | 0.003 |
| Modulation amplitude (V) | 0.05 |

EXAMPLE 2

Synthesis of N-Hydroxysuccinimide Ester of Ferrocenecarboxylic Acid

Ferrocenecarboxylic acid (303 mg, 1.32 mmol) and N-hydroxysuccinimide (170 mg, 1.47 mmol) were dissolved in dioxane (15 ml) and added with stirring to a solution of dicyclohexylcarbodiimide (305 mg, 1.48 mmol) in dioxane (3 ml). The mixture was stirred at room temperature for 24 hours during which time a precipitate was formed. The precipitate was removed by filtration, solvent was removed from the filtrate in vacuo and the resulting solid purified by silica gel column chromatography, eluting with 8:2 petrol: ethyl acetate. Yield 320 mg, 74%.

EXAMPLE 3

Synthesis of Ferrocenyl Oligonucleotides

Lyophilised amino-modified oligonucleotide was rehydrated in the correct volume of $K_2CO_3/KHCO_3$ buffer (500 mM, pH 9.0) to give an oligonucleotide concentration of 0.5 nmol$\mu l^{-1}$. Amino-modified oligonucleotide (40 µl, 0.5 nmol$\mu l^{-1}$) was added slowly with vortexing to a solution of the N-hydroxysuccinimide ester of ferrocenecarboxylic acid in DMF (40 µl, 375 mM). The solution was shaken at room temperature overnight. It was then diluted with ammonium acetate (920 µl, 100 mM, pH 7.0) and purified using two NAP 10 columns, eluting firstly with ammonium acetate (100 mM, pH 7.0), and then with autoclaved deionised water. Ferrocenylated oligonucleotides were partially purified by NAP 10 column to remove salt and low molecular weight ferrocene species to give a mixture of ferrocene labelled and unlabelled oligonucleotides. No further purification was carried out before use. Amino-modified oligonucleotides possessing four different linker structures: C7, C6, C12 and T(C9), varying in structure and point of attachment, were used in labeling reactions. C6, C12 and T(C9) linkers were attached at the 5' end of the oligonucleotide, via the terminal phosphate ester or the base. The C7 linker was attached via the terminal phosphate ester at the 3' end of the oligonucleotide. The label structures are given in Formulae I to IV. Oligonucleotide concentration of the eluent was determined by measuring its absorbance at 260 nm. Presence of the ferrocene label was confirmed by voltammetric analysis.

EXAMPLE 4

S1 Nuclease Digestion

Olignucleotide digestion reactions (100 µl) contained oligonucleotide (3.5-9 µM concentrations detailed below), ammonium acetate (250 mM, pH 6.5), zinc acetate (4.5 mM) and S1 Nuclease (0.4 U$\mu l^{-1}$). Reactions were incubated at 37° C. for 1 hour. Complete digestion of the oligonucleotide was confirmed by polyacrylamide gel analysis of a 10 µl aliquot of the crude reaction mix. Multiple reactions were pooled prior to voltammetric analysis, to give a final volume of 200 µl. By way of comparison, "no-enzyme" reactions were performed as described above, omitting S1 Nuclease from the reaction mixture. Heated enzyme controls were performed as described above, using S1 Nuclease that had previously been thermally denatured by heating at 95° C. for 15 minutes.

In the following, the reactants and conditions are as described above, and the voltammetry conditions are as given in Table 1 except where otherwise stated.

EXAMPLE 4(A)

Oligonucleotide: BAPR oligonucleotide labelled at 3' end by ferrocene with a 7-carbon spacer moiety (Formula I).

Concentration of oligonucleotide: 7.0 µM

Voltammetry conditions: As in Table 1 except that the interval time was 0.09 s and the modulation time 0.5 s.

Figure 2A:
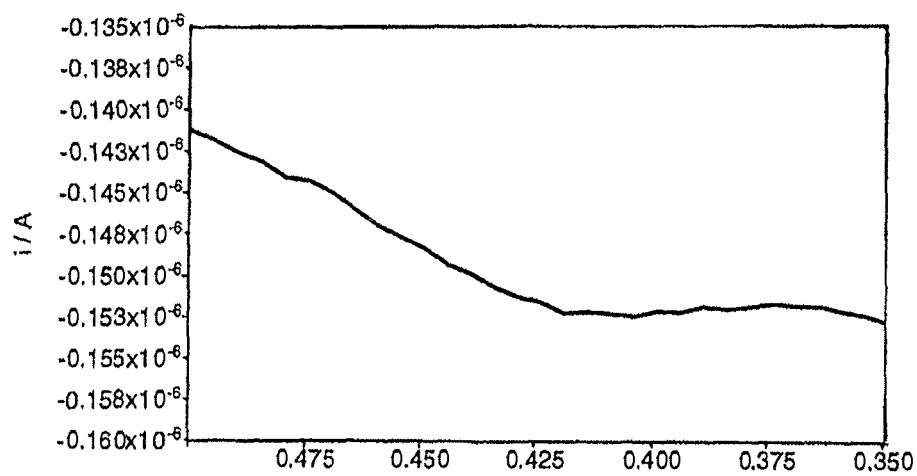
FIGS. 2A, 2B, 2C and 2D are differential pulse voltammograms of ferrocene labelled BAPR oligonucleotide as described in Example 4(a) below.
Figure 2B:
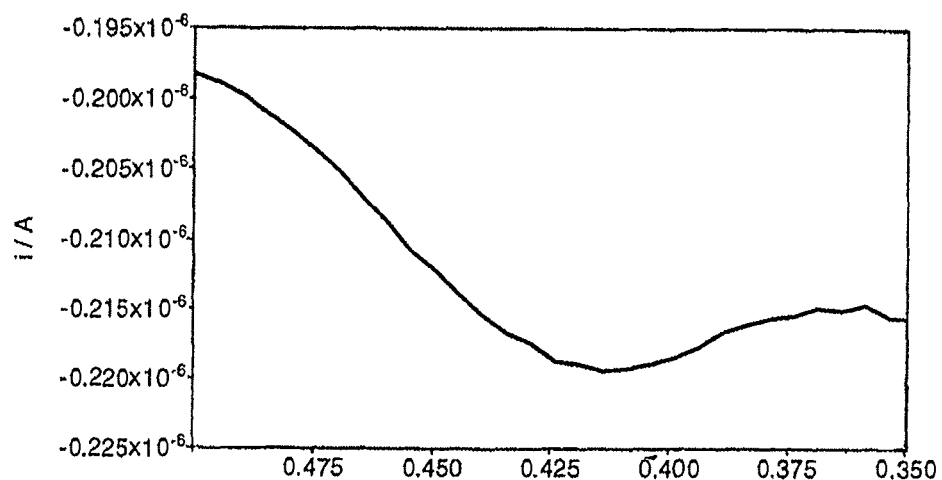
Figure 2C:
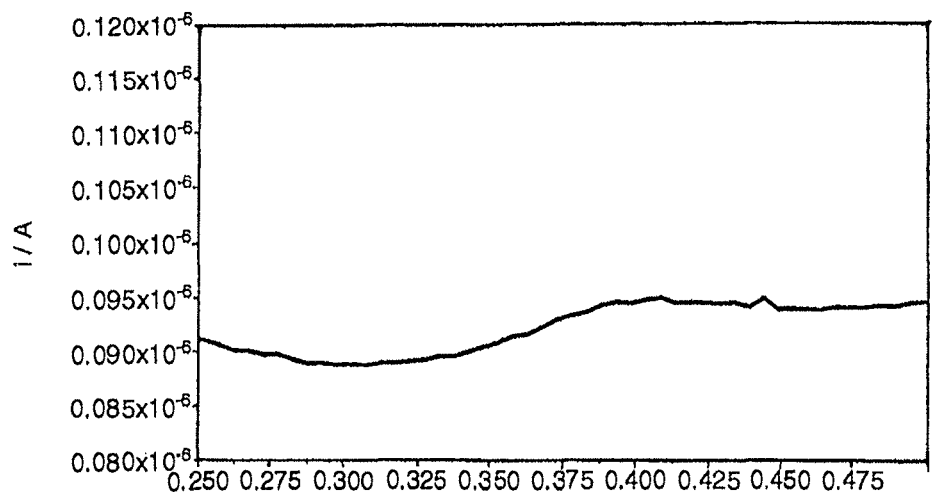
Figure 2D:
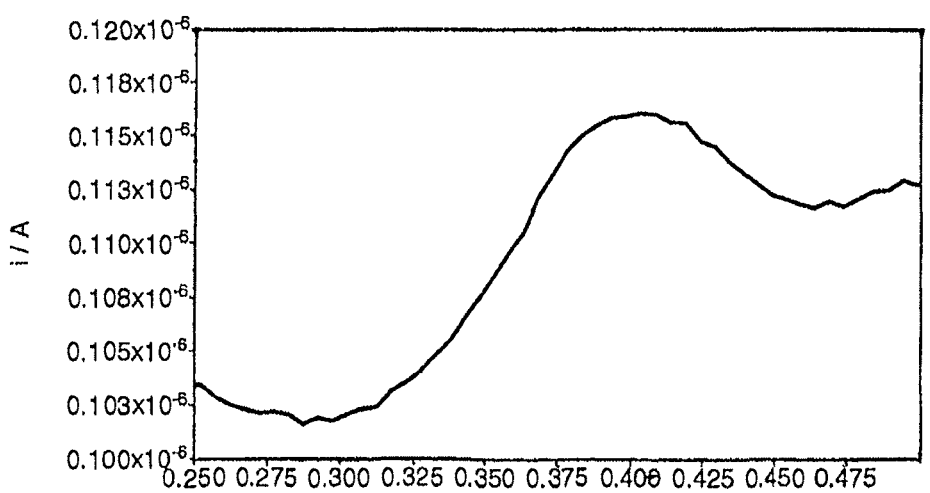

The results are shown in FIG. 2A (cathodic sweep of "no-enzyme" control), FIG. 2B (cathodic sweep of solution including S1 nuclease), FIG. 2C (anodic sweep of "no-enzyme" control) and FIG. 2D (anodic sweep of solution including S1 nuclease). The measured peak values, peak positions and % peak enhancement for the solution including S1 nuclease (that is, with digested oligonucleotide) as compared the "no-enzyme" control are given in Table 2.

EXAMPLE 4(B)

Oligonucleotide: BAPR oligonucleotide labelled at 5' end by ferrocene with a 6-carbon spacer moiety (Formula II).

Concentration of oligonucleotide: 7.0 µM

Voltammetry conditions: As in Table 1 except that the interval time was 0.09 s and the modulation time 0.5 s.

Figure 3A:
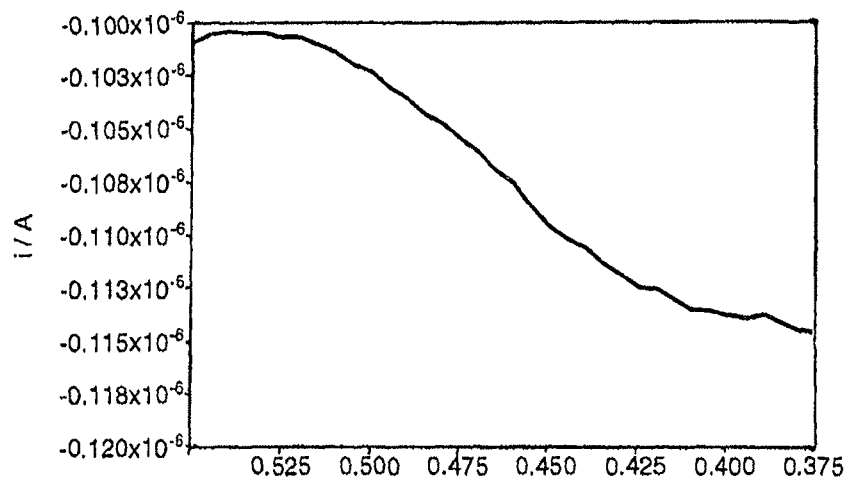
FIGS. 3A, 3B, 3C and 3D are differential pulse voltammograms of ferrocene labelled BAPR oligonucleotide as described in Example 4(b) below.
Figure 3B:
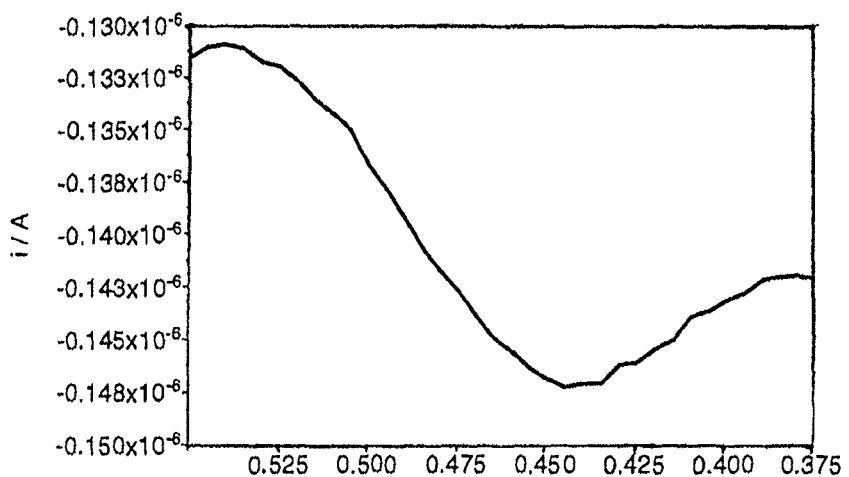
Figure 3C:
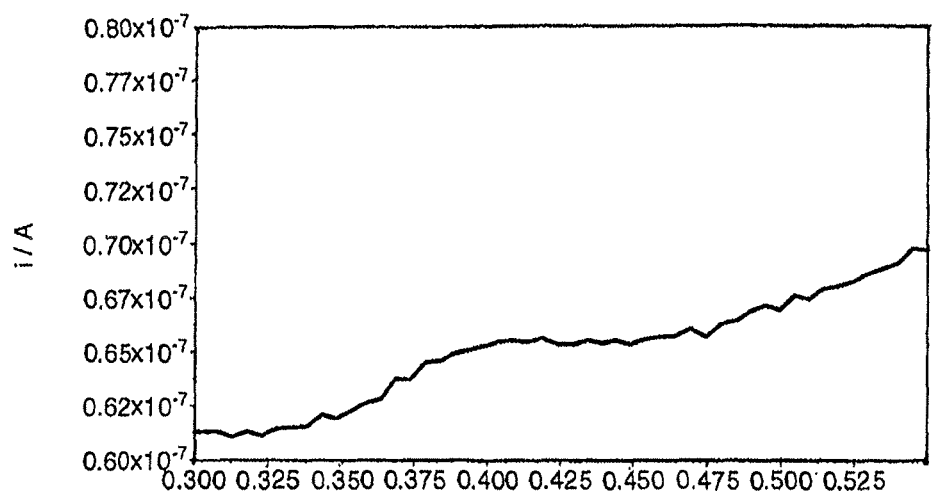
Figure 3D:
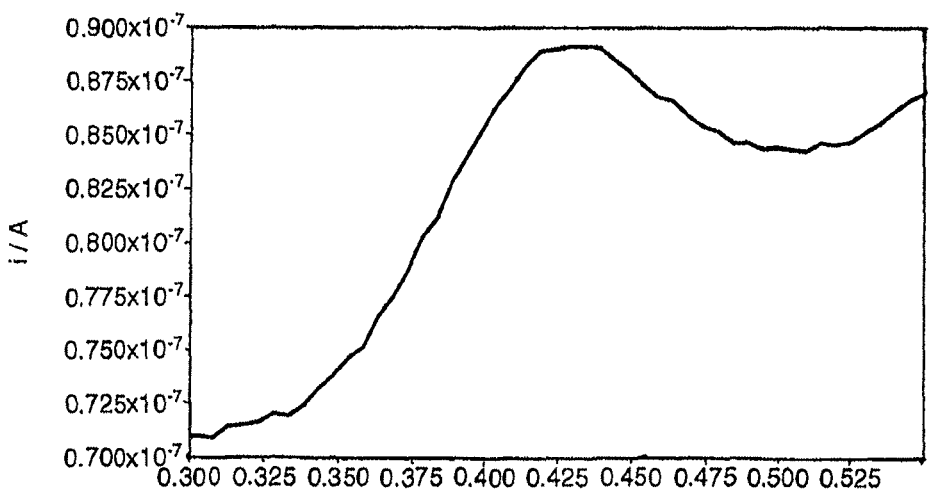

The results are shown in FIG. 3A (cathodic sweep of "no-enzyme" control), FIG. 3B (cathodic sweep of solution including S1 nuclease), FIG. 3C (anodic sweep of "no-enzyme" control) and FIG. 3D (anodic sweep of solution including S1 nuclease). The measured peak values, peak positions and % peak enhancement for the solution including S1 nuclease (that is, with digested oligonucleotide) as compared the "no-enzyme" control are given in Table 2.

EXAMPLE 4(C)

Oligonucleotide: T1BAPR oligonucleotide labelled at 3' end base by ferrocene with a 9-carbon spacer moiety (Formula IV).

Concentration of oligonucleotide: 8.8 µM

Voltammetry conditions: As in Table 1

Figure 4A:
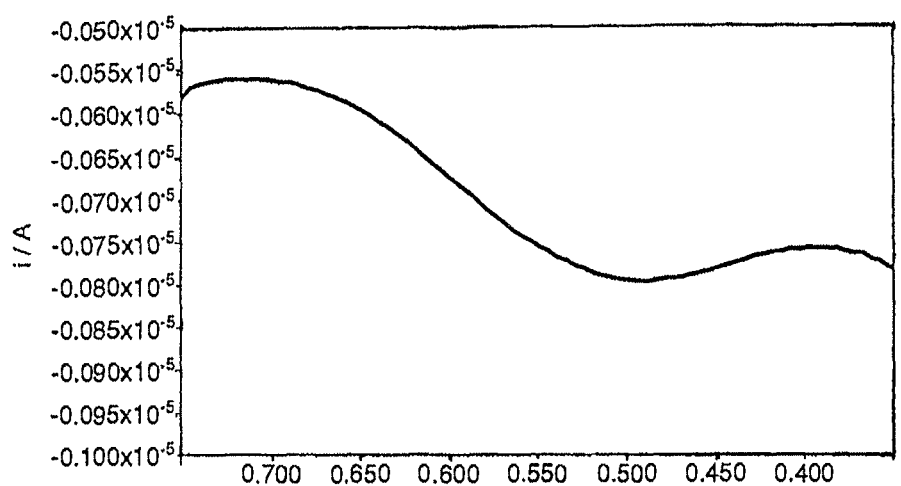
FIGS. 4A, 4B, 4C and 4D are differential pulse voltammograms of ferrocene labelled T1BAPR oligonucleotide as described in Example 4(c) below.
Figure 4B:
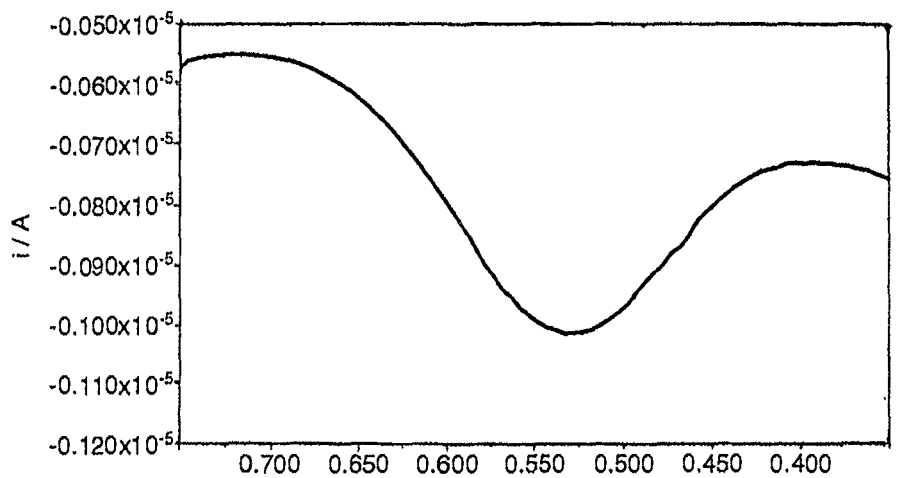
Figure 4C:
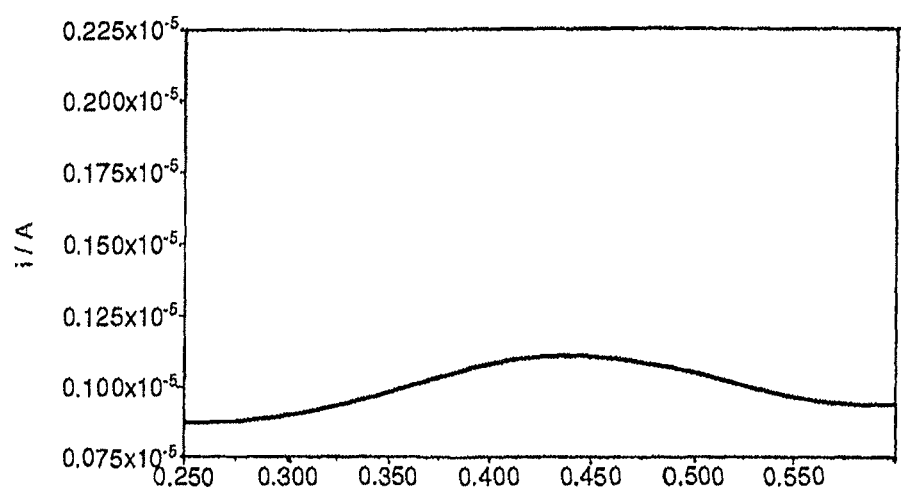
Figure 4D:
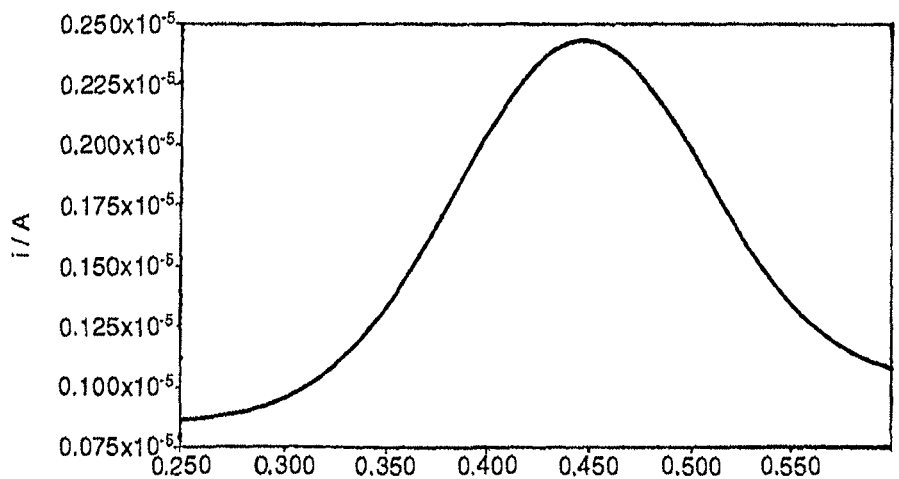

The results are shown in FIG. 4A (cathodic sweep of "no-enzyme" control), FIG. 4B (cathodic sweep of solution including S1 nuclease), FIG. 4C (anodic sweep of "no-enzyme" control) and FIG. 4D (anodic sweep of solution including S1 nuclease). The measured peak values, peak positions and % peak enhancement for the solution including S1 nuclease (that is, with digested oligonucleotide) as compared the "no-enzyme" control are given in Table 2.

EXAMPLE 4(D)

Oligonucleotide: BAPR oligonucleotide labelled at 5' end by ferrocene with a 12-carbon spacer moiety (Formula III).

Concentration of oligonucleotide: 7.0 µM.

Voltammetry conditions: As in Table 1 except that the interval time was 0.09 s and the modulation time 0.5 s.

Figure 5A:
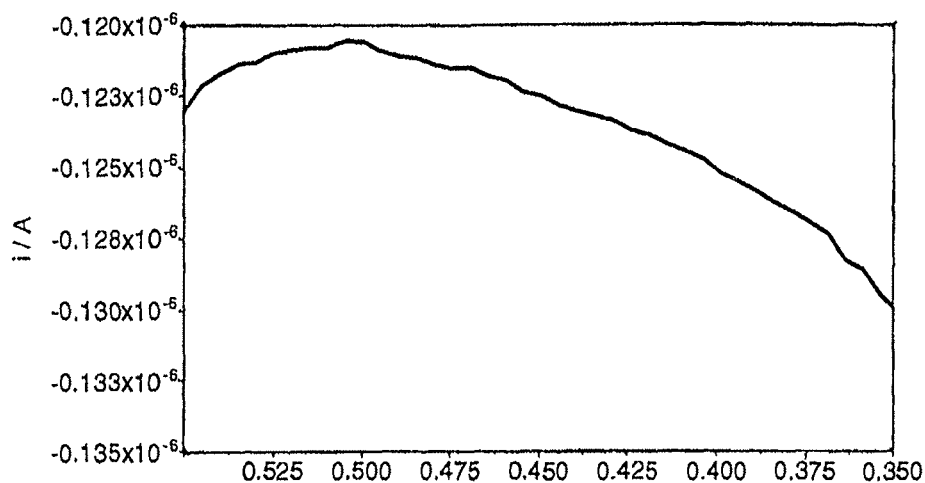
FIGS. 5A, 5B, 5C and 5D are differential pulse voltammograms of ferrocene labelled BAPR oligonucleotide as described in Example 4(d) below.
Figure 5B:
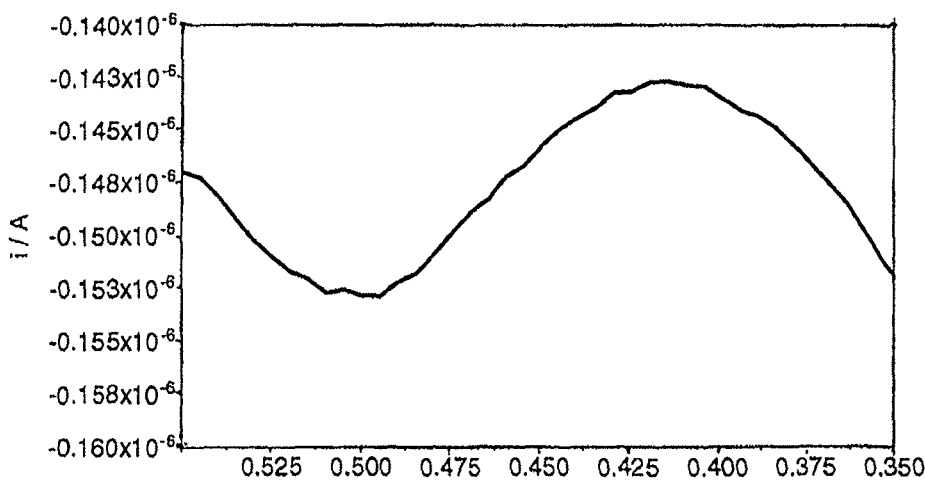
Figure 5C:
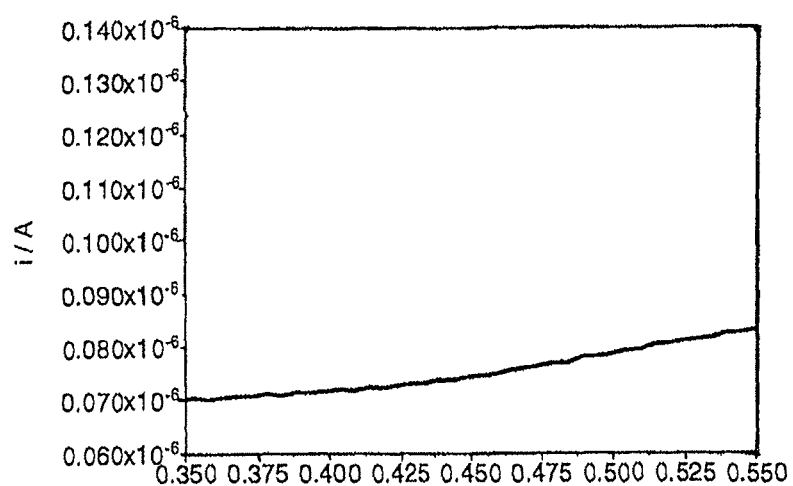
Figure 5D:
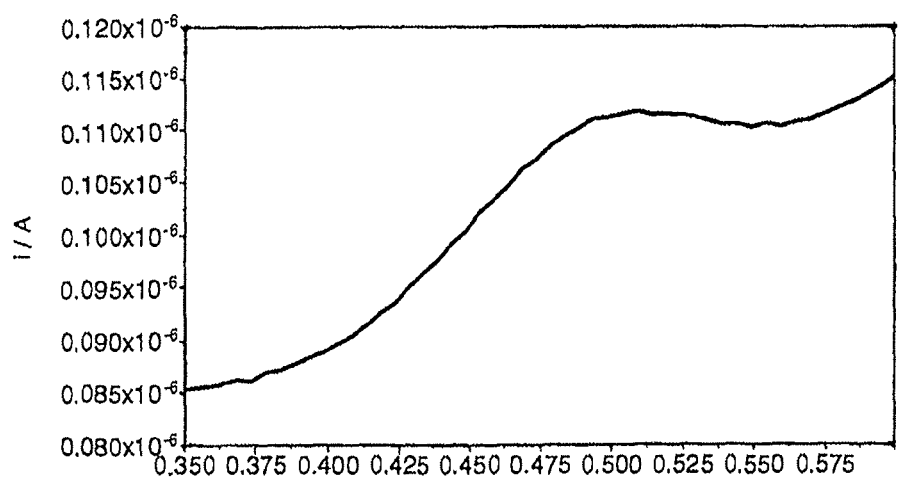

The results are shown in FIG. 5A (cathodic sweep of "no-enzyme" control), FIG. 5B (cathodic sweep of solution including S1 nuclease), FIG. 5C (anodic sweep of "no-enzyme" control) and FIG. 5D (anodic sweep of solution including S1 nuclease). The measured peak values, peak positions and % peak enhancement for the solution including S1 nuclease (that is, with digested oligonucleotide) as compared the "no-enzyme" control are given in Table 2.

EXAMPLE 4(E)

Oligonucleotide: GSDPR oligonucleotide labelled at 5' end by ferrocene with a 12-carbon spacer moiety (Formula III).

Concentration of oligonucleotide: 3.5 µM.

Voltammetry conditions: As in Table 1.

Figure 6A:
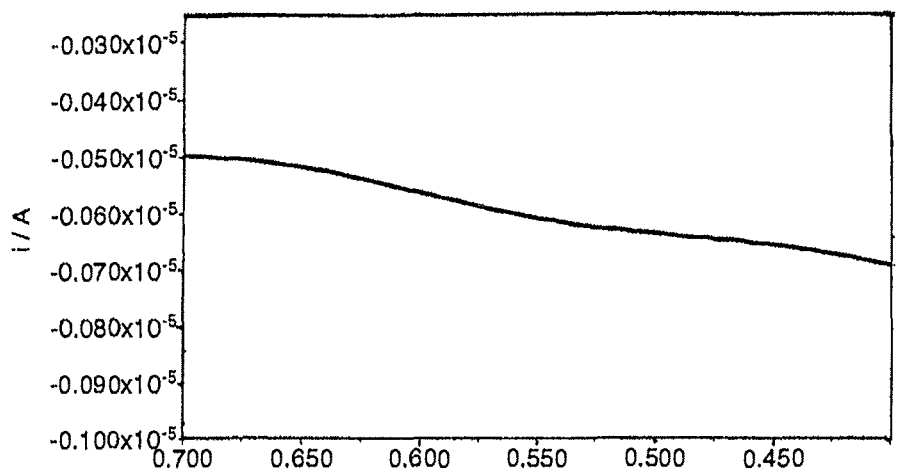
FIGS. 6A, 6B, 6C and 6D are differential pulse voltammograms of ferrocene labelled GSDPR oligonucleotide as described in Example 4(e) below.
Figure 6B:
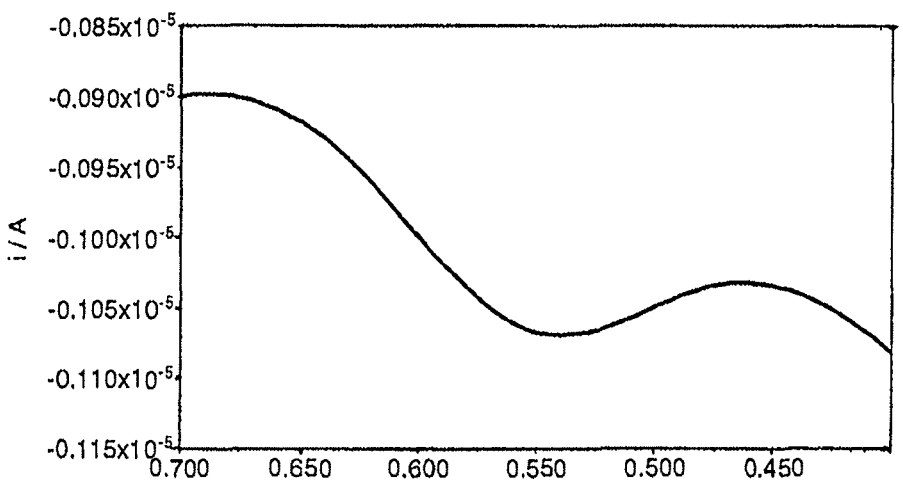
Figure 6C:
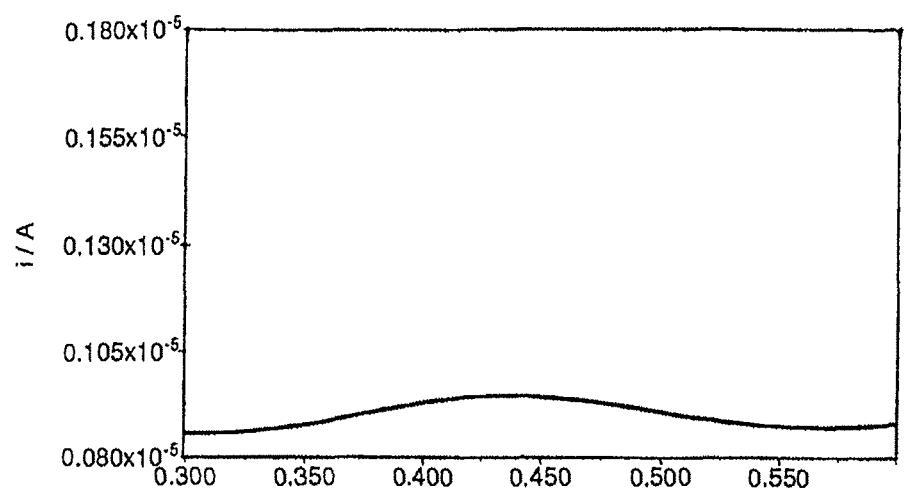
Figure 6D:
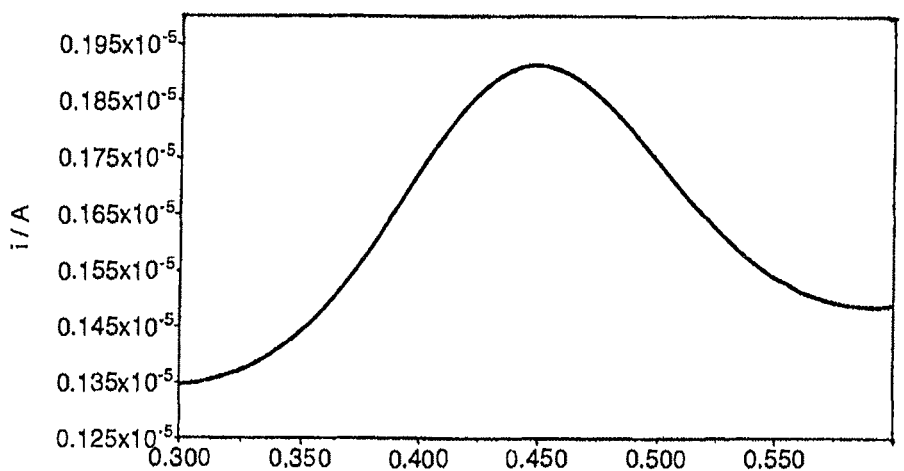

The results are shown in FIG. 6A (cathodic sweep of "no-enzyme" control), FIG. 6B (cathodic sweep of solution including S1 nuclease), FIG. 6C (anodic sweep of "no-enzyme" control) and FIG. 6D (anodic sweep of solution including S1 nuclease). The measured peak values, peak positions and % peak enhancement for the solution including S1 nuclease (that is, with digested oligonucleotide) as compared the "no-enzyme" control are given in Table 2.

EXAMPLE 4(F)

Oligonucleotide: MC11PR oligonucleotide labelled at 5' end by ferrocene with a 12-carbon spacer moiety (Formula III).

Concentration of oligonucleotide: 3.5 µM.

Voltammetry conditions: As in Table 1.

Figure 7A:
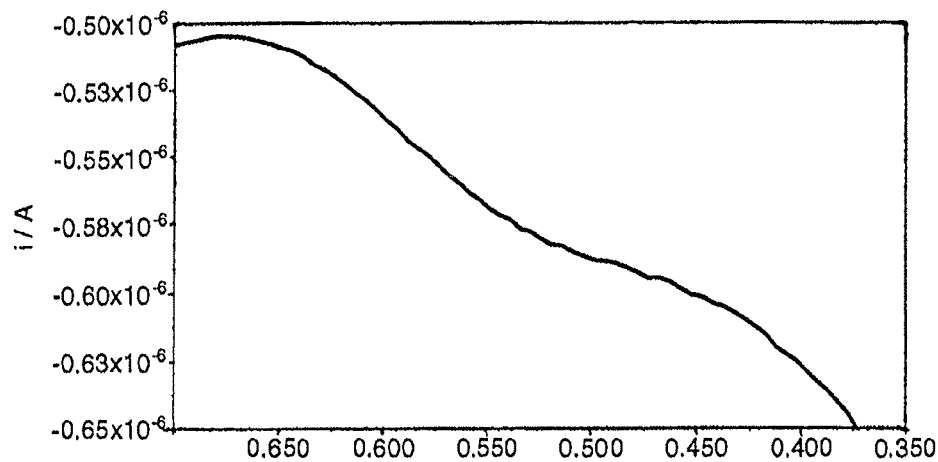
FIGS. 7A, 7B, 7C and 7D are differential pulse voltammograms of ferrocene labelled MC11PR oligonucleotide as described in Example 4(f) below.
Figure 7B:
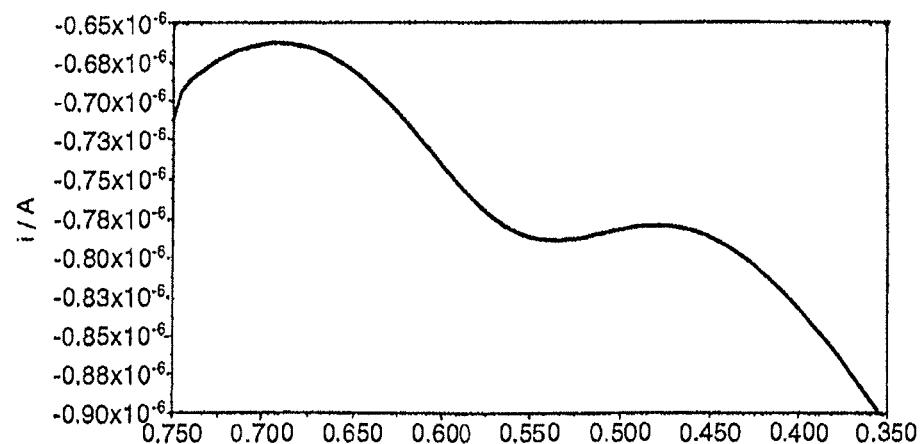
Figure 7C:
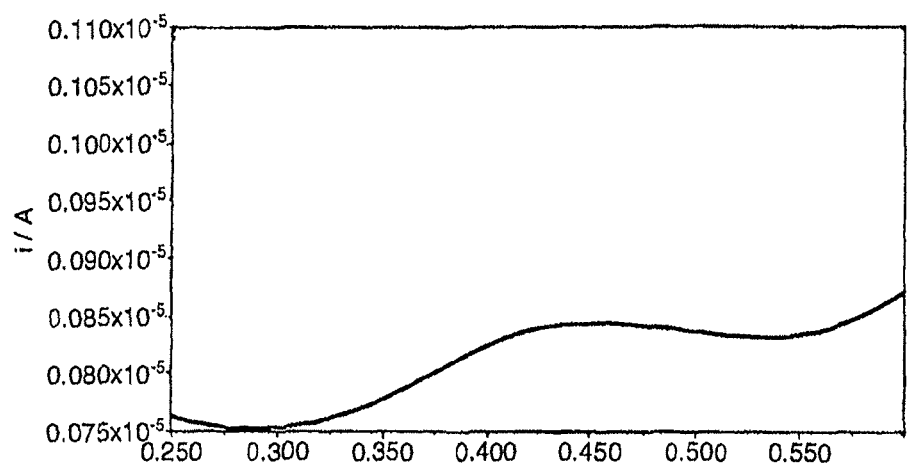
Figure 7D:
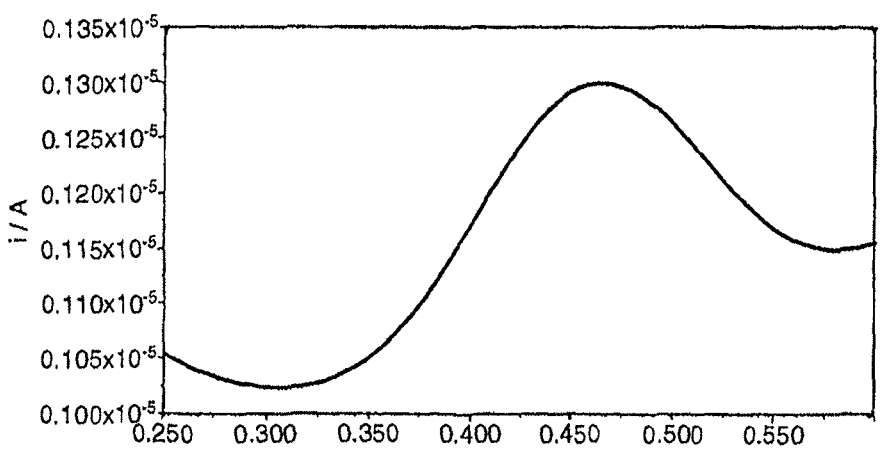

The results are shown in FIG. 7A (cathodic sweep of "no-enzyme" control), FIG. 7B (cathodic sweep of solution including S1 nuclease), FIG. 7C (anodic sweep of "no-enzyme" control) and FIG. 7D (anodic sweep of solution including S1 nuclease). The measured peak values, peak positions and % peak enhancement for the solution including S1 nuclease (that is, with digested oligonucleotide) as compared the "no-enzyme" control are given in Table 2.

EXAMPLE 4(G)

Comparison

Oligonucleotide: BAFR, unlabelled.
Concentration of oligonucleotide: 8.8 µM.
Voltammetry conditions: As in Table 1

Figure 8A:
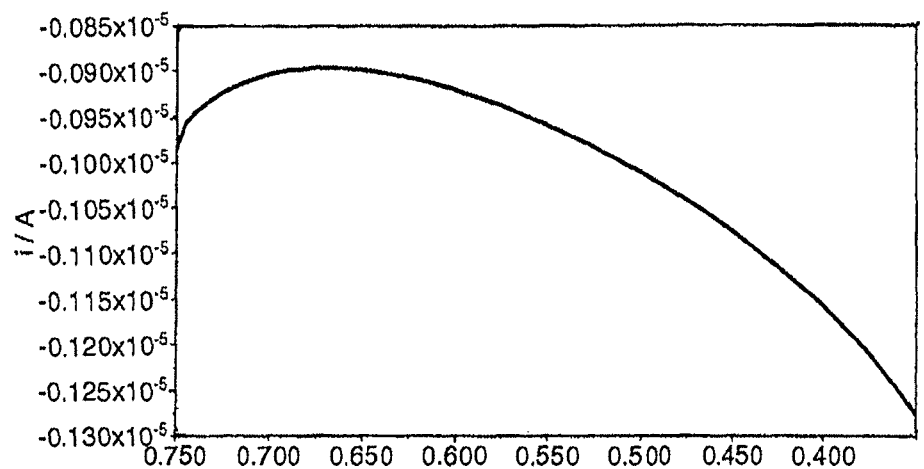
FIGS. 8A and 8B are differential pulse voltammograms of unlabelled BAFR oligonucleotide as described in Example 4(g) below.
Figure 8B:
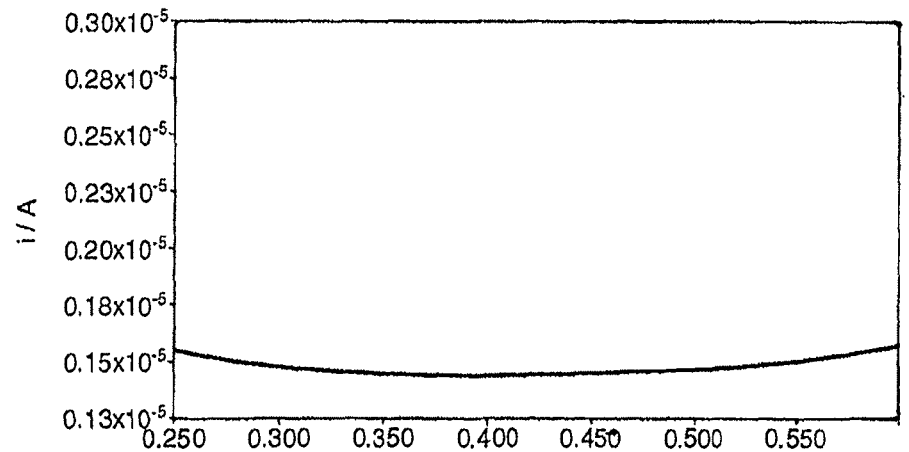

The results are shown in FIG. 8A (cathodic sweep) and FIG. 8B (anodic sweep). No peak was observed in either sweep. CL EXAMPLE 4(H)

Comparison

Oligonucleotide: T1BAPR oligonucleotide labelled at 5' end base by ferrocene with a 9-carbon spacer moiety (Formula IV).

Concentration of oligonucleotide: 8.8 µM.
Voltammetry conditions: As in Table 1.

Figure 9A:
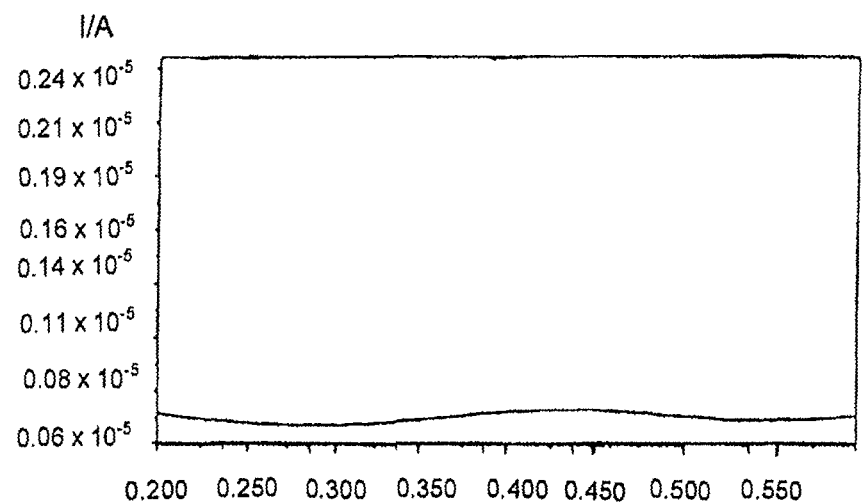
FIGS. 9A and 9B are differential pulse voltammograms of control reactions for ferrocene labelled T1BAPR oligonucleotide as described in Example 4(h) below.
Figure 9B:
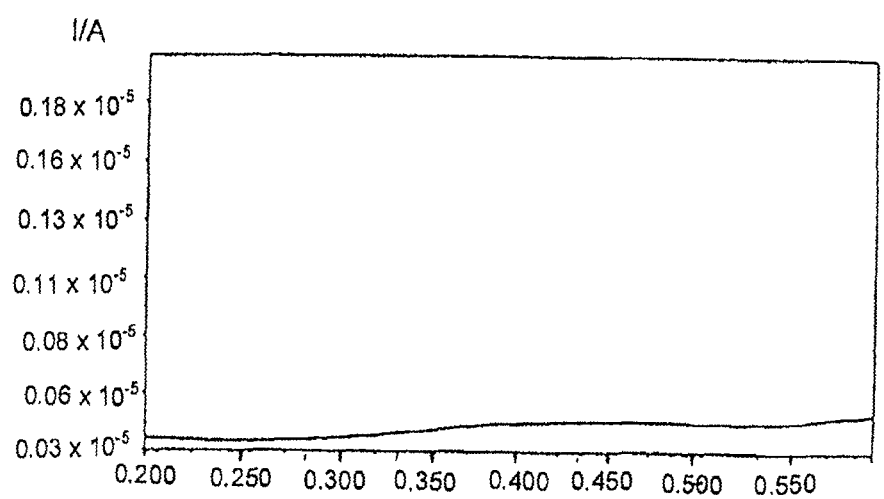

The results are shown in FIG. 9A (anodic sweep of "no-enzyme" control) and FIG. 9B (anodic sweep of heated enzyme control including S1 nuclease). In FIG. 9A, a peak height of 60.6 µA (peak position 424 mV) was recorded, whilst in FIG. 9B, a peak height of 39.9 µA (peak position 409 mV) was recorded.

Ferrocene related peaks were observed at 300-500 mV. No peaks were observed in this range when non-ferrocenylated oligonucleotides were analysed (FIGS. 8A and 8B). Comparison of digested ferrocene labelled oligonucleotides and no-enzyme controls showed that an increase in peak height was obtained on digestion of the oligonucleotide (Table 4).

In order to confirm that the observed changes were not due to the presence of enzyme, or components of the enzyme storage buffer, digestion experiments were also performed using heat-denatured enzyme (Example 4(h)). No significant changes to the ferrocene signal were observed when comparing heat denatured enzyme and no enzyme controls.

Digestion experiments of two additional oligonucleotide sequences with the C12 ferrocene-oligonucleotide linker were performed; Ferrocene-C12-MC11PR (FIG. 11B) and Ferrocene-C12-GSDPR (FIGS. 6B and 6D). An increase in peak height of the ferrocene related signal of digested oligonucleotide was observed for each sequence.

TABLE 4

Positions and heights for ferrocene related peaks on anodic and cathodic differential pulse voltammograms

|  | Undigested | | Digested | | % increase in peak height upon digestion |
|---|---|---|---|---|---|
| Oligo | Peak position | Peak Height | Peak Position | Peak Height | |
| Cathodic Sweeps | | | | | |
| BAPR C7 | 41 | — | 424 | −10.16 | 218 |
| BAPR C6 | 42 | — | 444 | −8.87 | 274 |
| T1BAPR | 51 | — | 533 | −456.5 | 485 |
| BAPR | — | — | 500 | −4.71 | |
| GSDPR | 53 | — | 554 | −65.43 | 215 |
| MC11PR | 55 | — | 564 | −49 | 224 |
| Anodic Sweeps | | | | | |
| BAPR C7 | 39 | 3.39 | 394 | 9.18 | 266 |
| BAPR C6 | 39 | 1.63 | 419 | 10.3 | 632 |
| T1BAPR | 43 | 82.8 | 444 | 818 | 988 |
| BAPR | — | — | 494 | 6.7 | |
| GSDPR | 43 | 62.9 | 394 | 359 | 571 |
| MC11PR | 42 | 60.1 | 394 | 196 | 326 |

EXAMPLE 5

PCR

PCR amplification was performed from human genomic DNA (40 ng per 100 µl reaction), or gel purified PCR amplicons. PCR amplicons used for subsequent amplifications were purified by agarose gel with Nucleospin Extract kits (Macherey-Nagel) following the protocol supplied. All ferrocenyl oligonucleotide probes were 3′ phosphorylated.

Primers, template and probe used for individual reactions are detailed above.

100 µl reactions contained Tris HCl (15 mM, pH 8.0), potassium chloride (50 mM), magnesium chloride (3.5 mM), dATP, TTP, dCTP, dGTP (200 µM each), forward primer (1.0 µM), reverse primer (1.0 µM), ferrocenyl oligonucleotide probe (0.9 µM), AmpliTaq Gold (0.04 U$\mu$l$^{-1}$). Samples were incubated at 95° C. for 10 minutes (initial denaturation and enzyme activation) followed by 40 cycles of denaturation at 95° C. for 15 s, and primer annealing and extension at 60° C. for 1 min.

Fifteen 100 µl reactions were prepared and pooled. The crude reaction mixture was then concentrated to 200 µl total volume prior to voltammetric analysis.

In the following, the reactants and conditions are as described above and the voltammetry conditions are as given in Table 1 unless otherwise stated.

EXAMPLE 5(A)

Oligonucleotide: BAPR oligonucleotide labelled at 5′ end with a 12-carbon spacer moiety (Formula III).

Positive reaction: (ß actin) template: ß actin PCR amplicon; primers: BAF, BAR.

Negative reaction: (cystic fibrosis transmembrane conductance regulator) template: cystic fibrosis PCR amplicon; primers: CFT 01, CFT 03.

Voltammetry conditions: As in Table 1.

Figure 10A:
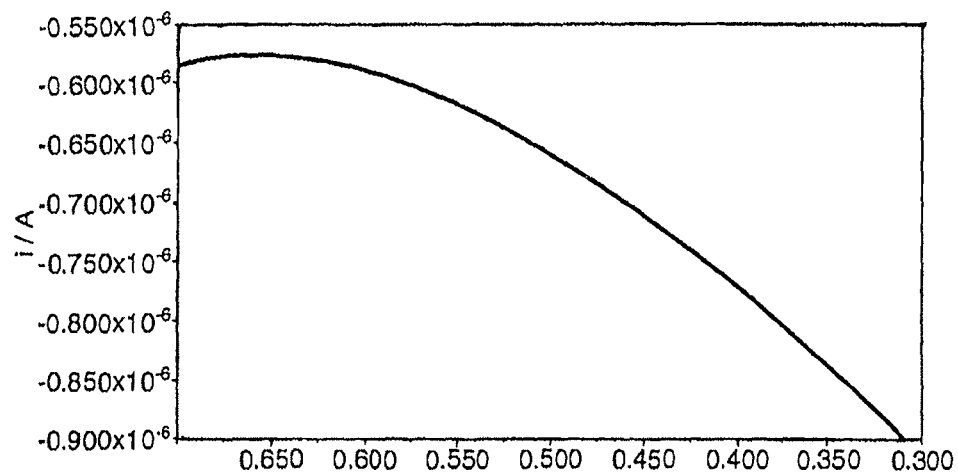
FIGS. 10A, 10B, 10C and 10D are differential pulse voltammograms of PCR mixture containing labelled BAPR oligonucleotide as described in Example 5(a) below.

The results were as follows:

FIG. 10A negative reaction, cathodic sweep, no peak observed

Figure 10B:
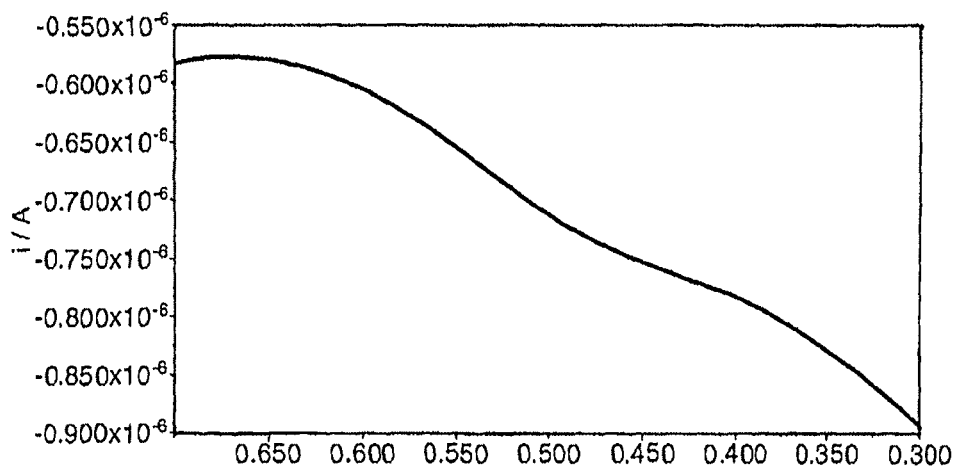

FIG. 10B positive reaction, cathodic sweep, peak position: 493 mV, peak height: −19.4 nA.

Figure 10C:
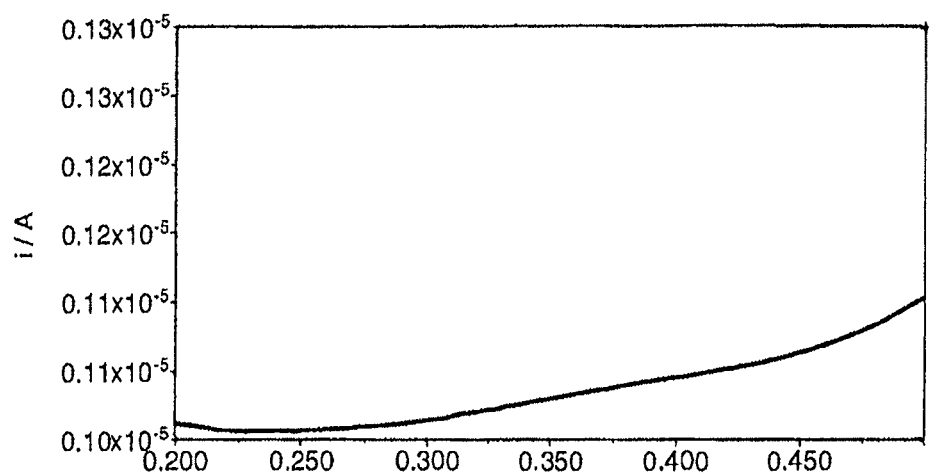

FIG. 10C negative reaction, anodic sweep, no peak observed.

Figure 10D:
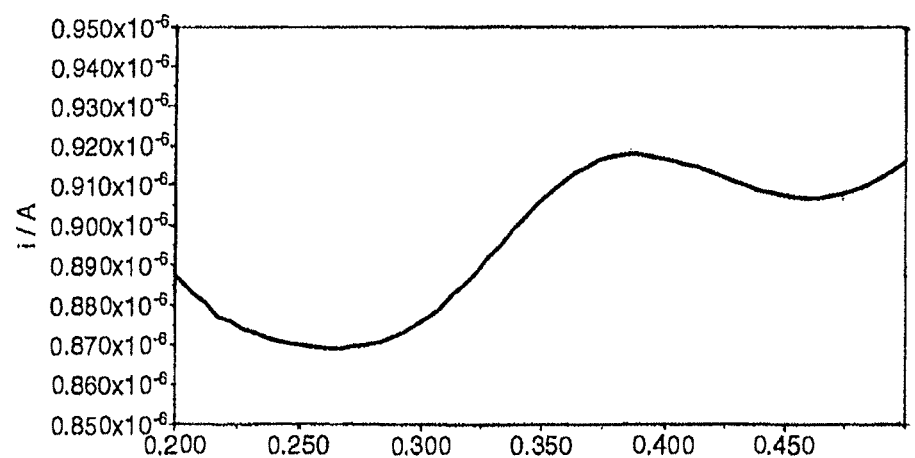

FIG. 10D positive reaction, anodic sweep, peak position: 373 mV, peak height: 27.3 nA. CL EXAMPLE 5(B)

Oligonucleotide: MC11PR oligonucleotide labelled at 5′ end with a 12-carbon spacer moiety (Formula III).

Figure 11A:
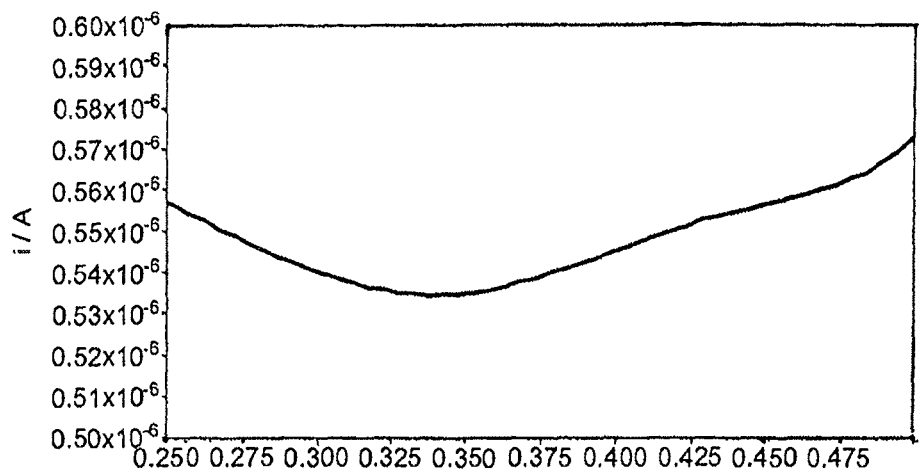
FIGS. 11A, 11B and 11C are differential pulse voltammograms of another PCR mixture containing ferrocene labelled MC11PR oligonucleotide as described in Example 5(b) below.

Positive reaction: (Medium chain acyl-CoA dehydrogenase) template: MCAD PCR amplicon or genomic template; primers: MC11w, MC11com;

Negative reaction: (glucose-6-phosphatase) template: Glucose-6-Phosphatase PCR amplicon; primers: GSDw, GSDcom;

FIG. 11A negative reaction, anodic sweep, peak position: 429 mV, peak height: 1.84 nA.

Figure 11B:
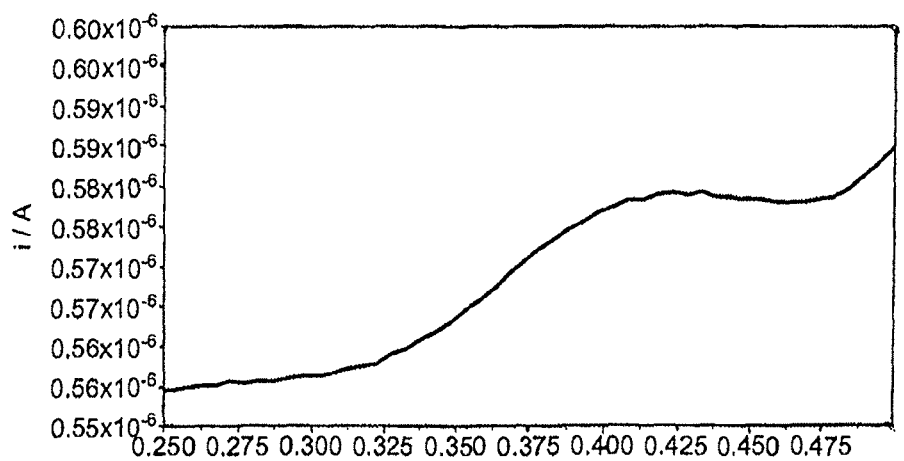

FIG. 11B positive reaction (PCR amplicon template), anodic sweep, peak position: 388 mV, peak height: 7.62 nA.

Figure 11C:
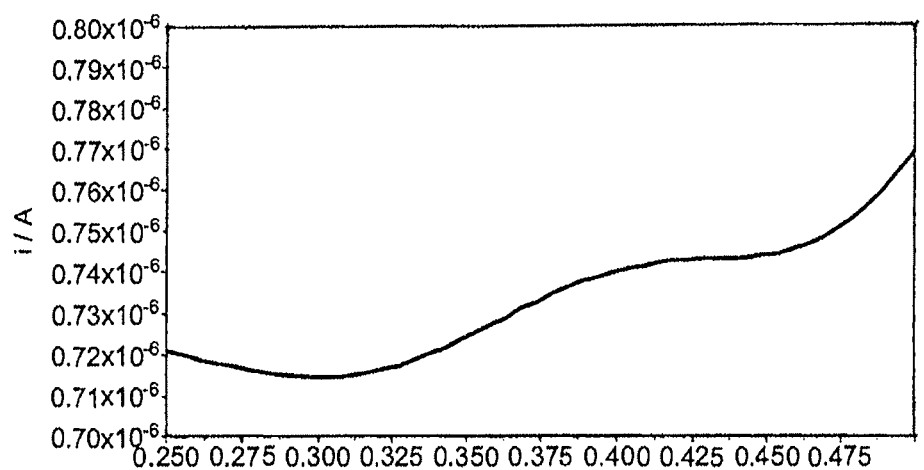

FIG. 11C positive reaction (genomic template), anodic sweep, peak position: 409 mV, peak height: 8.11 nA. CL EXAMPLE 5(C)

Oligonucleotide: T1BAPR oligonucleotide labelled at 5′ end with a 9-carbon spacer moiety.

Positive reaction: (ß actin) template: human genomic DNA; primers:
BAF, BAR

Negative reaction: (glucose-6-phosphatase) template: human genomic DNA; primers: GSDw, GSDcom.

Voltammetry conditions: as in Table 1.

Figure 12A:
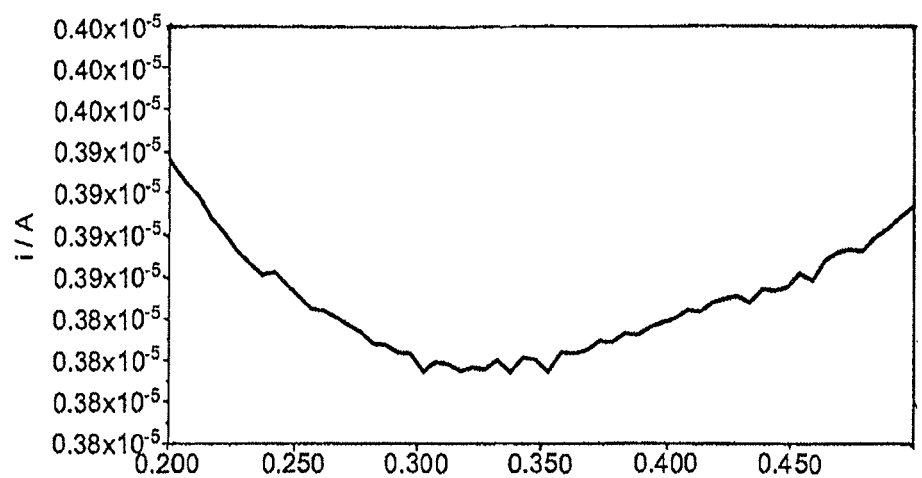
FIGS. 12A, 12B, 12C and 12D are differential pulse voltammograms of a PCR mixture containing ferrocene labelled T1BAPR oligonucleotide as described in Example 5(c)

The results were as follows:

FIG. 12A: negative reaction, anodic sweep.

Figure 12B:
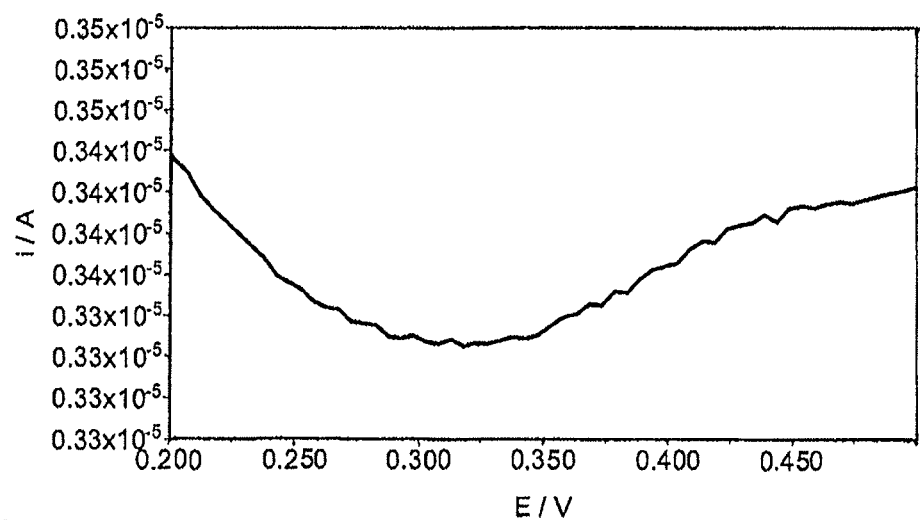

FIG. 12B: positive reaction, anodic sweep, peak position: 429 mV, peak height 36 nA.

Figure 12C:
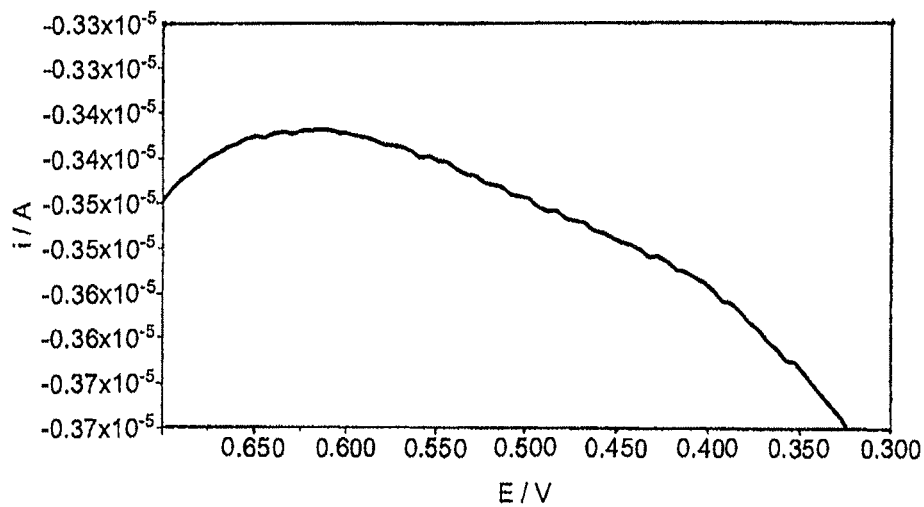

FIG. 12C: negative reaction cathodic sweep.

Figure 12D:
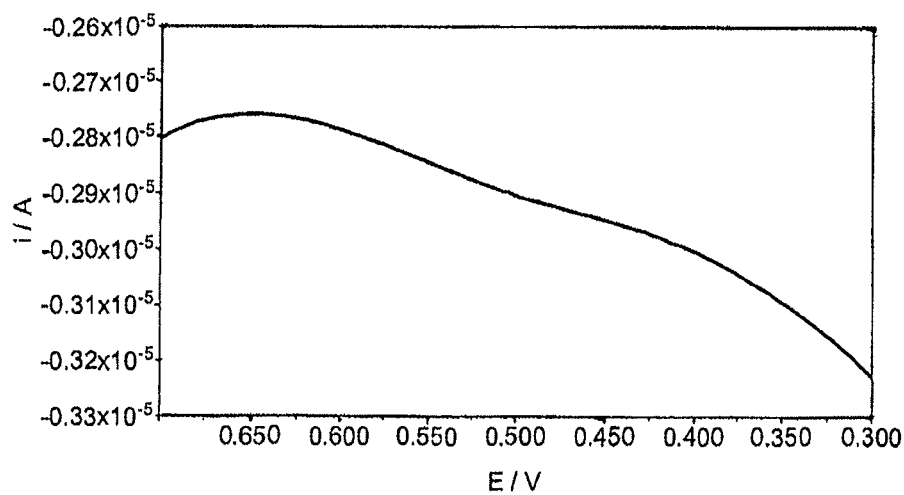

FIG. 12D: positive reaction cathodic sweep, peak position: 498 mV, peak height: 14 nA. CL EXAMPLE 5(D)

Oligonucleotide GSDPR labelled at 5′ end with a 12 carbon spacer moiety.

Positive reaction: (glucose-6-phosphatase) template: human genomic DNA; primers: GSDw, GSDcom.

Negative reaction: (ß actin) template: human genomic DNA; primers: BAF, BAR.

Figure 13A:
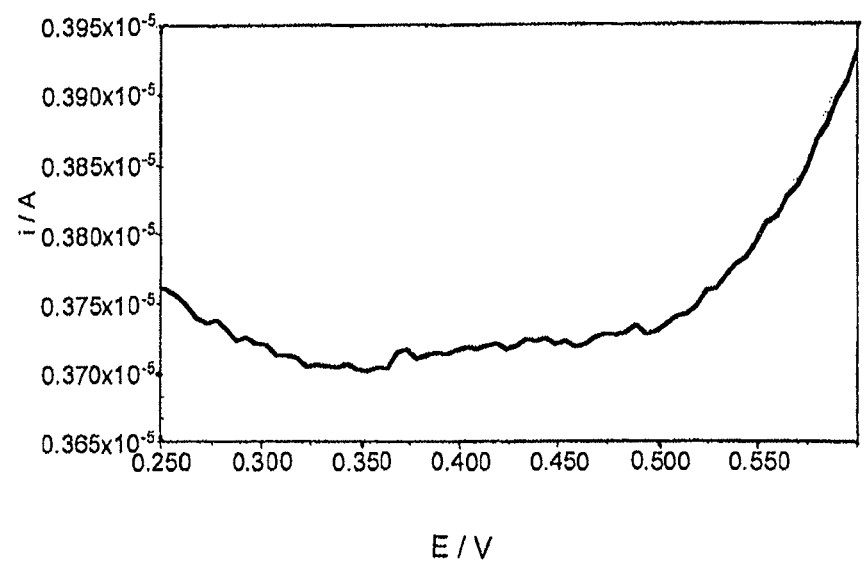
FIGS. 13A, 13B, 13C and 13D are differential pulse voltammograms of a PCR mixture containing ferrocene labelled GSDPR oligonucleotide as described in Example 5(d)

FIG. 13A: negative reaction, anodic sweep.

Figure 13B:
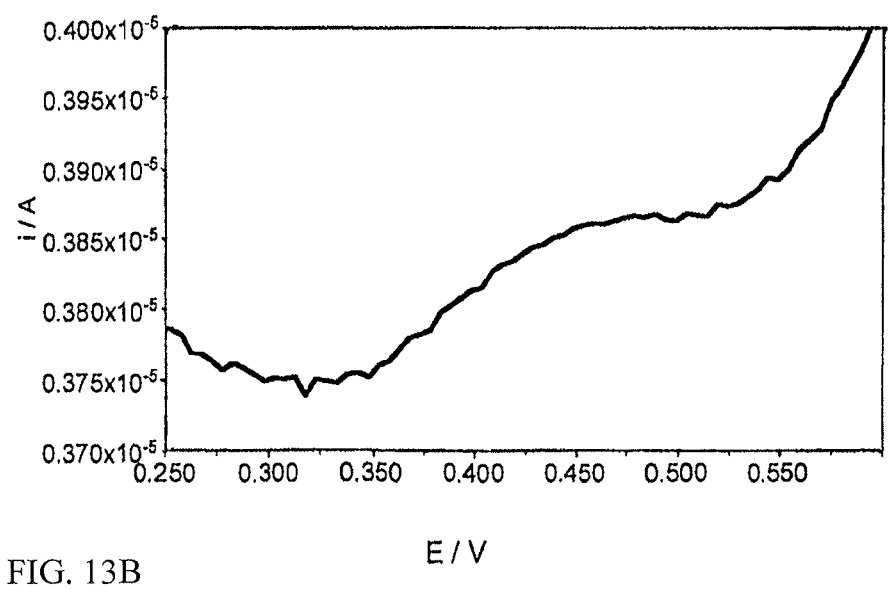

FIG. 13B: positive reaction, anodic sweep, peak, position: 439 mV, peak height: 23 nA.

Figure 13C:
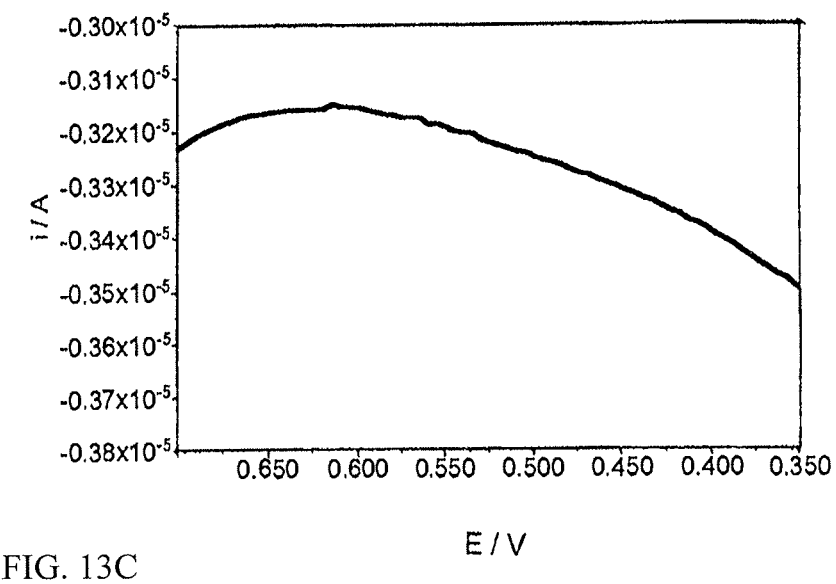

FIG. 13C: negative reaction cathodic sweep.

Figure 13D:
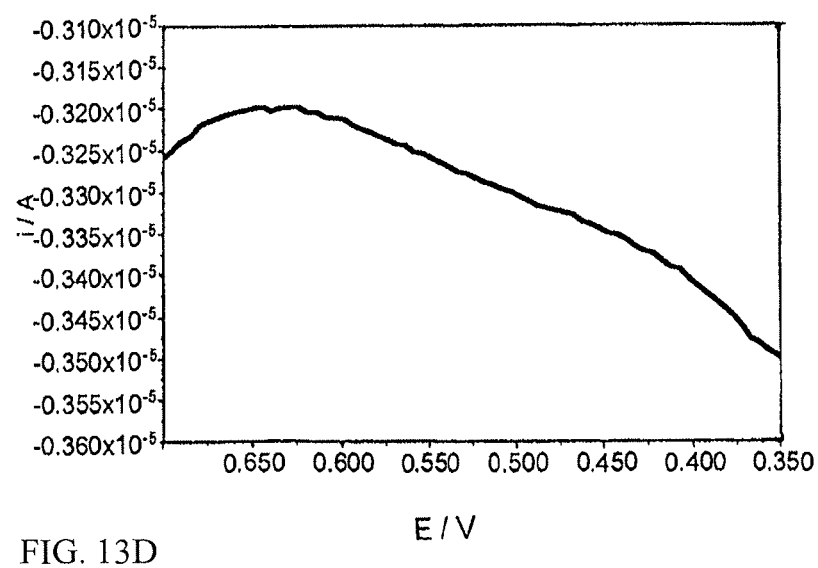
Figure 14A:
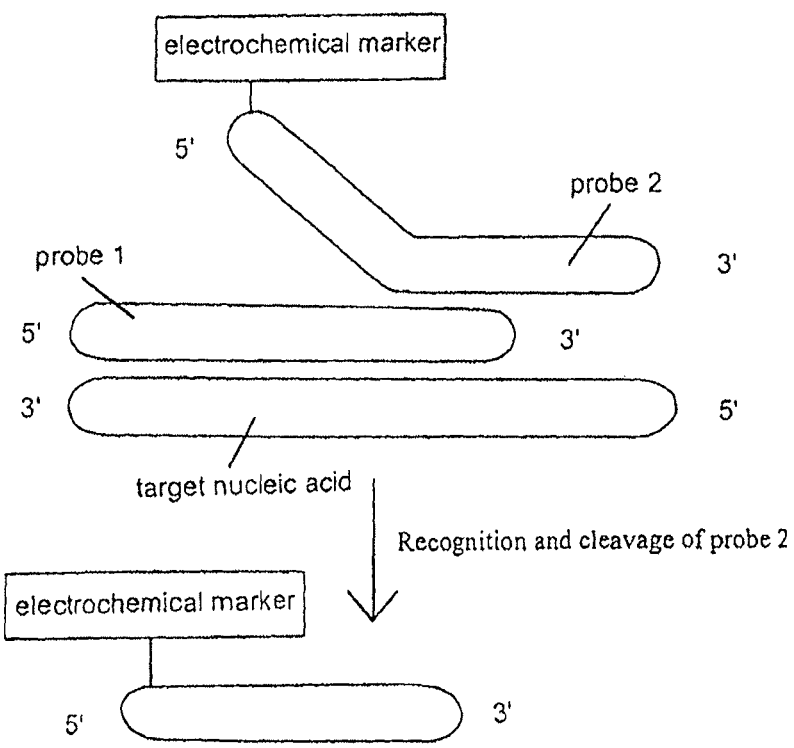
FIGS. 14A and 14B are schematic representations of the Invader fluorogenic nucleic acid detection system adapted for use in a method of the invention.
Figure 14B:
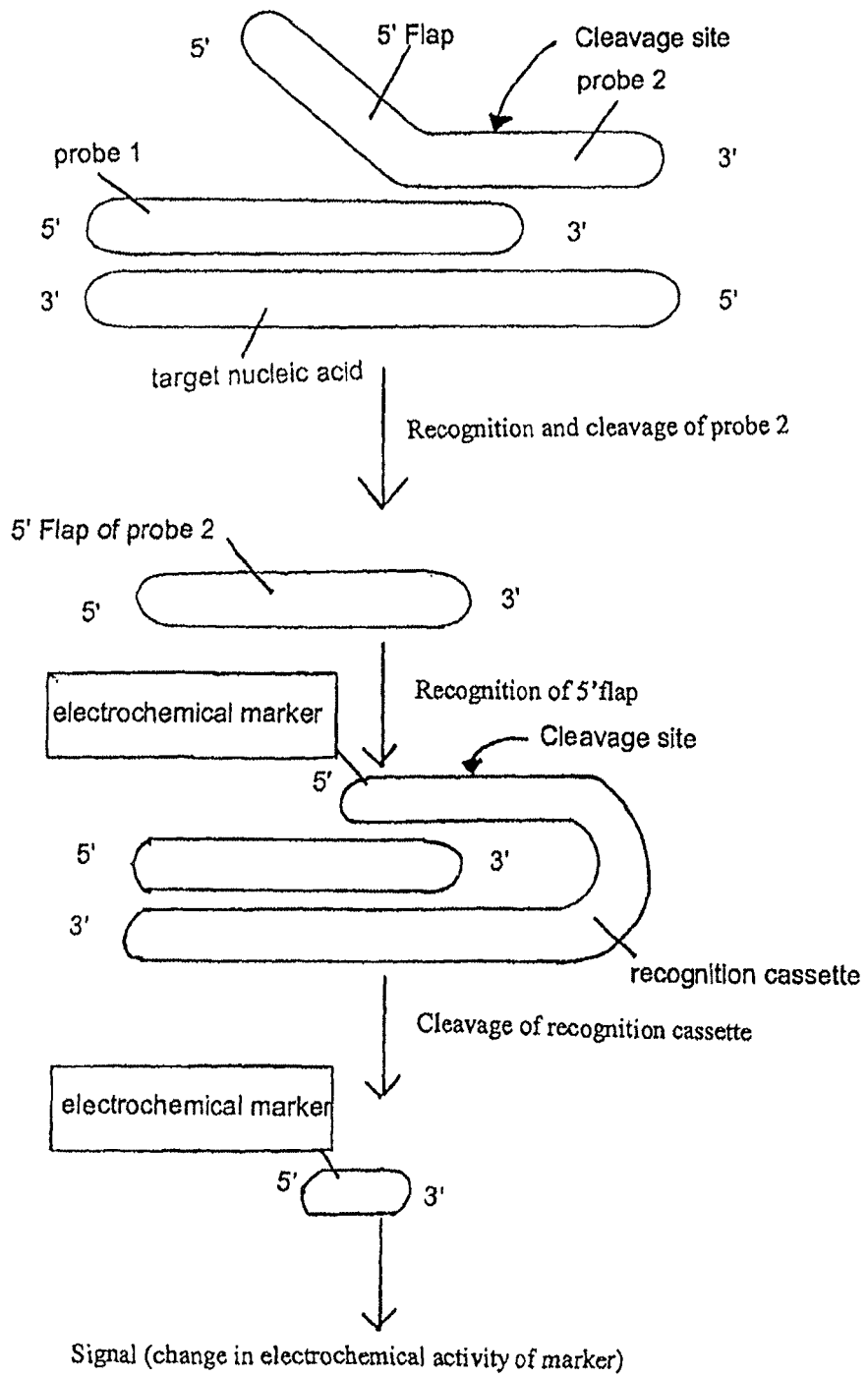

FIG. 13D: positive reaction cathodic sweep.

In this example, to demonstrate the sequence specific detection of PCR products with ferrocenylated oligonucleotide probes, probe and primer sequences from previously optimized fluorogenic 5′ nuclease assays were used. PCR amplification from beta actin glucose-6-phosphatase and medium chain acyl-CoA dehydrogenase genes was performed using either purified amplicon or human genomic DNA template. In all PCR experiments probes with C12 ferrocene linkers attached at the 5′ end were used. The 3′ end of all PCR experiments probes were extension blocked by phosphorylation.

Ferrocenyl oligonucleotide probes were added to PCR mixes which amplified complementary targets (positive reactions) and non-complementary targets (negative reactions). To improve detection of the ferrocene species, reactions were combined and concentrated before voltammetric analysis.

Voltammetric analysis was performed on the crude PCR mixes. In each case a ferrocene related signal is observed for positive reactions (containing digested probe). No signal is observed for negative reactions (containing undigested probe). CL EXAMPLE 6A Synthesis of Ferrocene Carbonyl Azide Ferrocene carbonyl azide was prepared from ferrocenecarboxylic acid by reaction with oxalyl chloride and sodium azide.

EXAMPLE 6B

Synthesis of N-Hydroxysuccinimide Ester of 4-(3'-Ferrocenylureido)-1-Benzoic Acid ml) and ethyl acetate (50 ml) were charged to the reaction mixture. The ethyl acetate phase was separated and the aqueous was extracted with ethyl acetate (100 ml). The ethyl acetate phases were combined, dried with sodium sulphate and concentrated in vacuo to afford the crude product as an orange oil, which was purified using silica flash chromatography with a gradient system from ethyl acetate 60/petroleum ether (bp 40-60° C.) 40 to ethyl acetate. Drying in a vacuum oven yielded N-hydroxysuccinimide ester of 4-(3'-ferrocenylureido)-1-benzoic acid as fine orange crystals (237 mg, 66%). $R_f$ (5:1 ethyl acetate/petroleum ether (bp 40-60° C.)=0.41 $^1$H-NMR δ (300 MHz, d6-DMSO) 2.88 (4H, s, Hh), 3.98 (2H, t, J=1.8 Hz, Hc), 4.16 (5H, s, Ha), 4.55 (2H, t, J=1.8 Hz, Hb), 7.68 (2H, m, Hf), 8.00 (2H, m, Hg), 8.11 (1H, s, Hd), 9.16 (1H, s, He). $^{13}$C-NMR δ (75.5 MHz, $d_6$-DMSO) 25.9 (Cl), 61.1 64.2 (Cb and Cc), 69.1 (Ca), 117.7 (Cg), 131.9 (Ch), 170.9 (Ck). MS (FAB+m/z) 462.07 [M+H].

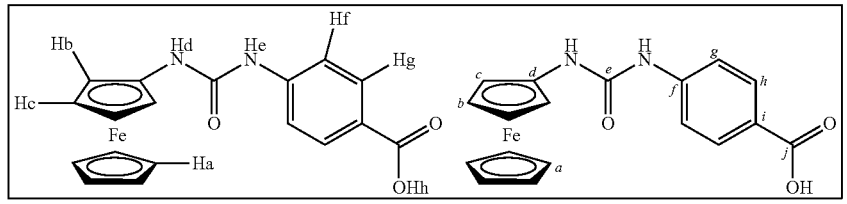

To a purged round-bottom flask was charged ferrocene carbonyl azide (300 mg, 1.18 mmol, 1.00 equiv.), 4-aminobenzoic acid (244 mg, 1.78 mmol, 1.50 equiv.) and 1,4-dioxane (40 ml) under nitrogen. The reaction mixture was stirred under nitrogen in a 100° C. bath for 2 hr 50 min and then allowed to cool to room temperature. 2M HCl (100 ml) was charged to the reaction mixture and the product was extracted into ethyl acetate (150 nil). This phase was washed with 2M HCl (100 ml), dried with sodium sulphate and concentrated in vacuo to afford the product. Further drying in a vacuum oven yielded as orange crystals (413 mg 96%). $^1$H-NMR δ (300 MHz, $d_6$-DMSO) 3.96 (2H, b, Hc), 4.14 (5H, s, Ha), 4.53 (2H, b, Hb), 7.54 (2H, m, Hf), 7.85 (2H, in, Hg), 7.98 (1H, s, Hd), 8.87 (1H, s, He) 12.57 (1H, s, Hh)$^{13}$C-NMR δ (75.5 MHz, $d_6$-DMSO) 61.0 64.1 66.7 68.1 (Ca, d), 117.2 (Cg), 123.5 (Cj), 130.9 (Ch), 144.6 (Cf), 152.8 (Ce). CL EXAMPLE 6C Synthesis of N-Hydroxysuccinimide Ester of 4-(3'-Ferrocenylureido)-1-Benzoic Acid Dicyclohexylcarbodiimide (DCC) (194 mg, 0.939 mmol, 1.14 equiv.) was dissolved in anhydrous 1,4-Dioxane (2 ml) and charged to a purged round-bottom flask, under nitrogen. N-hydroxysuccinimide (108 mg, 0.939 mmol, 1.14 equiv.) was charged. 4-(3'-Ferrocenylureido)-1-benzoic acid (300 mg, 0.823 mmol 1.0 equiv.) was dissolved in anhydrous 1,4-Dioxane (13 ml) and charged dropwise to the flask. The solution was stirred at room temperature for 23 hr. A small amount of light brown solid was removed from the red/orange reaction mixture by Buchner filtration. Water (100

EXAMPLE 6D

Synthesis of 3.5-di(3'-ferrocenylureido)-1-benzoic Acid

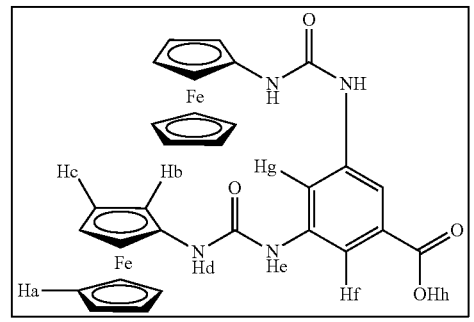

To a purged round-bottom flask was charged ferrocene carbonyl azide (800 mg, 3.14 mmol, 2.5 equiv.), 3,5-diaminobenzoic acid (194 mg, 1.25 mmol, 1.00 equiv.) and 1,4-dioxane (60 ml) under nitrogen. The reaction mixture was stirred under nitrogen in a 100° C. bath for 1 hr and then allowed to cool to room temperature. Water (300 ml) and ethyl acetate (150 ml) were charged to the reaction mixture. To improve separation the aqueous phase was acidified with HCl. The ethyl acetate phase was washed with water (100 ml) and on standing solid began to precipitate. The solution was concentrated in vacuo to afford the crude product as an orange oil, which was dried with a toluene azeotrope (100 ml), to yield a light orange solid. The product was purified using silica flash chromatography using gradient system from DCM 90/MeOH 10 to DCM 50/MeOH 50. Drying in a vacuum oven yielded (19) as orange crystals (205 mg, 27%). $^1$H-NMR δ (300 MHz, d6-DMSO) 3.95 (4H, b, Hc), 4.14 (10H, s, Ha), 4.54 (4H, b, Hb), 7.69 (2H, s, Hf), 7.81 (1H, s, Hg), 8.08 (2H, s, Hd), 8.94 (2H, s, He). MS (FAB+m/z) 607.07 [M+H]. CL EXAMPLE 7

Synthesis of 4-(3'-ferrocenylureido)-1-benzoic Acid Oligonucleotides

Lyophilised amino-modified oligonucleotide was rehydrated in the correct volume of $K_2CO_3/KHCO_3$ buffer (500 mM, pH 9.0) to give an oligonucleotide concentration of 0.5 nmolμl$^{-1}$. Amino-modified oligonucleotide (40 μl, 0.5 nmolμl$^{-1}$) was added slowly with vortexing to a solution of the ferrocene activated ester in DMSO (40 μl, 375 mM). The solution was shaken at room temperature overnight, it was then diluted with ammonium acetate (920 μl, 100 mM, pH 7.0) and purified using two NAP 10 columns (following the protocol supplied), eluting firstly with ammonium acetate (100 mM, pH 7.0), and then with autoclaved deionised water. Oligonucleotide concentration of the eluent was determined by measuring its absorbance at 260 nm. Presence of the ferrocene label was confirmed by voltammetric analysis.

EXAMPLE 8

S1 Nuclease and PCR with 4-(3'-ferrocenylureido)-1-benzoic Acid Labelled Substrates/Probes By use of 4-(3'-ferrocenylureido)-1-benzoic acid labelled substrates/probes and the voltammetry parameters as set out in table 2, Examples 4 and 5 were repeated with the concentrations of all reagents as described in those examples. The peak potential of the 4-(3'-ferrocmylureido)-1-benzoic acid nucleotides is lower than that of the ferrocene labelled nucleotides. That increases the sensitivity with which the electrochemical marker can be detected. In the Example 8 experiments it was, accordingly, not necessary to carry out the sample concentration step used in Example 4 and 5 and the method protocol was significantly simplified. The results for Example 8 (not shown) demonstrate that good sensitivity is observed without the sample concentration step.

EXAMPLE 9

T7 Exonuclease Substrate Specificity

200 μl of hairpin oligonucleotide and 200 μl of single stranded oligonucleotide were added to separate reaction tubes at a concentration of 7 μM in 1×T7 reaction buffer. T7 enzyme was added to each tube (5 μl, 2 Uμl$^{-1}$) and the mixtures were incubated for 1 hour at 25° C. Both oligos were previously labelled with Ferrocene via a C12 linker.

Figure 16A:
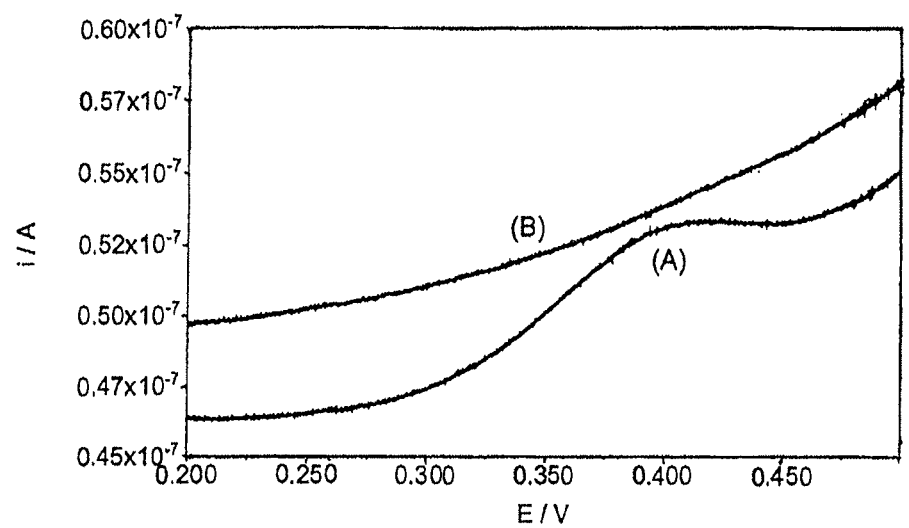
FIGS. 16A and 16B are differential pulse voltammograms illustrating T7 exonuclease substrate specificity (Example 9)
Figure 16B:
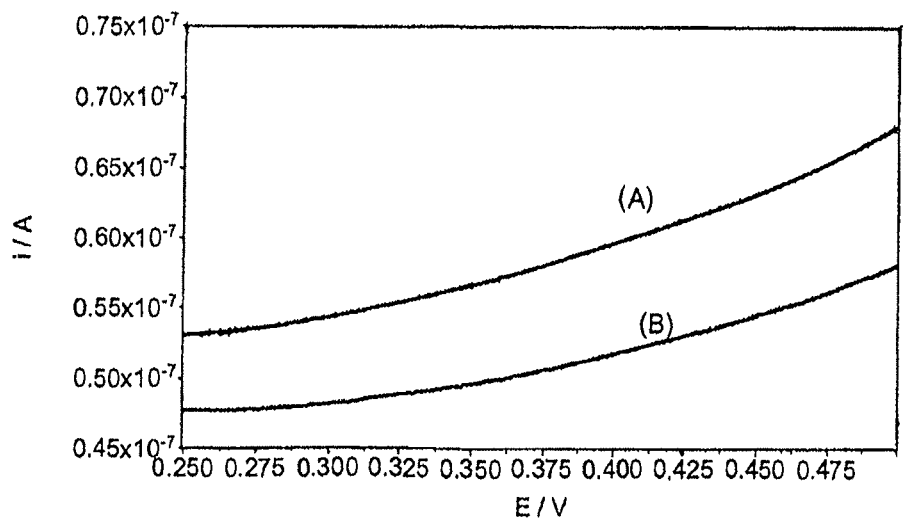

The results were as follows:
FIG. 16A: Line A—digestion of hairpin oligonucleotide duplex.
FIG. 16A: Line B—hairpin oligonucleotide duplex no enzyme control.
FIG. 16B: Line A—digestion of single stranded oligonucleotide.
FIG. 16B: Line B—single stranded oligonucleotide no enzyme control.

EXAMPLE 10

PCR Amplification with T7 Exonuclease Digestion

EXAMPLE 10(A)

Figure 17A:
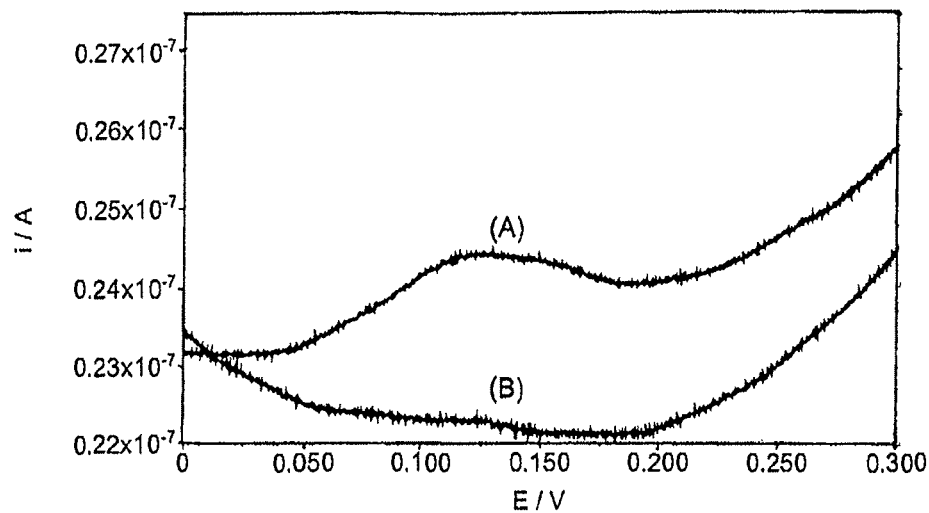
FIGS. 17A and 17B are differential pulse voltammograms illustrating T7 exonuclease digestion of PCR product labelled with 5' ferrocenylated primer (Example 10(a))
Figure 17B:
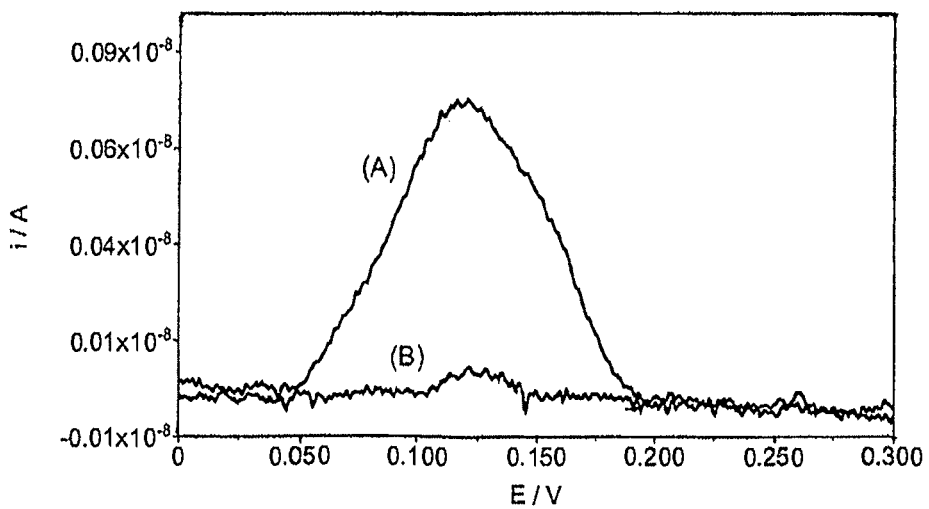

PCR Amplification with 5' Ferrocenylated Primer and T7 Exonuclease Digestion
PCR amplification was performed from human genomic DNA (40 ng per 100 μl reaction).
Primers, template and probe used for individual reactions are detailed in the results section. 100 μl reactions contained Tris Ha (15 mM, pH 8.0), potassium chloride (50 mM), magnesium chloride (3.5 mM), dATP, TTP, dCTP, dGTP (200 μM each), 5' ferrocenylated forward primer (0.5 μM), reverse primer (0.5 μM), Amplitaq Gold DNA Polymerase (0.1 Uμl$^{-1}$), BSA (0.1 mgμl$^{-1}$). Samples were incubated at 95° C. for 10 minutes (initial denaturation and enzyme activation) followed by 40 cycles of denaturation at 95° C. for 15 s, and primer annealing and extension at 60° C. for 1 min. Samples were immediately cooled to 25° C. and incubated at 25° C. for 5 minutes. T7 exonuclease (5 μl, 2 Uμl$^{-1}$) was added to the crude PCR mix and samples incubated for a further 20 minutes.
Two 100 μl reactions were prepared and pooled prior to voltammetric analysis.
The results were as follows:
Forward primer: MWllw ferrocenylated via a C12 linker
Reverse primer: MCllcom
FIG. 17A: Line A—MCAD PCR amplification positive PCR
FIG. 17A: Line B—MCAD PCR no Taq negative control
FIG. 17B: Lines A and B—as FIG. 17A but with baseline corrected data

EXAMPLE 10(B)

Figure 18A:
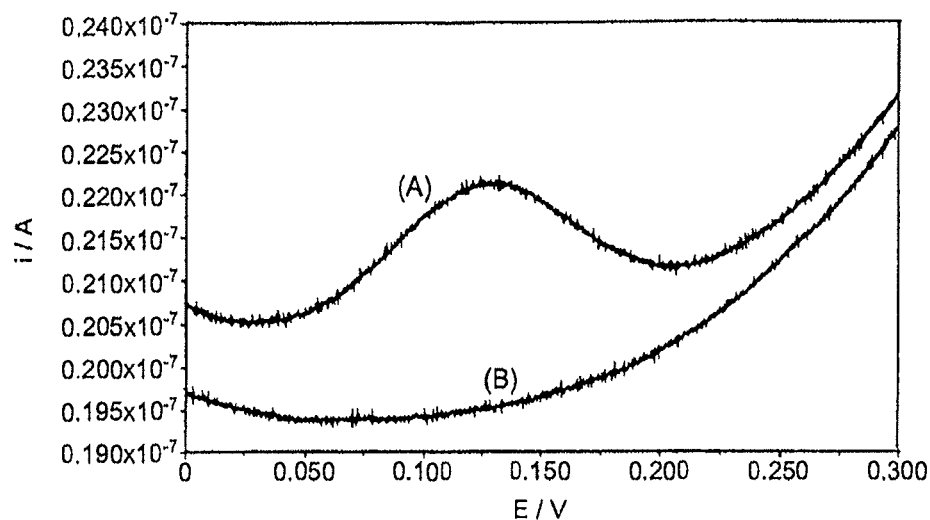
FIGS. 18A, 18B, 18C, 18D, 19A, 19B, 20A and 20B are differential pulse voltammograms illustrating T7 exonuclease digestion of Taqman (Trade Mark—Applied Biosystems) probe annealed to PCR product (Example 10(b))
Figure 18B:
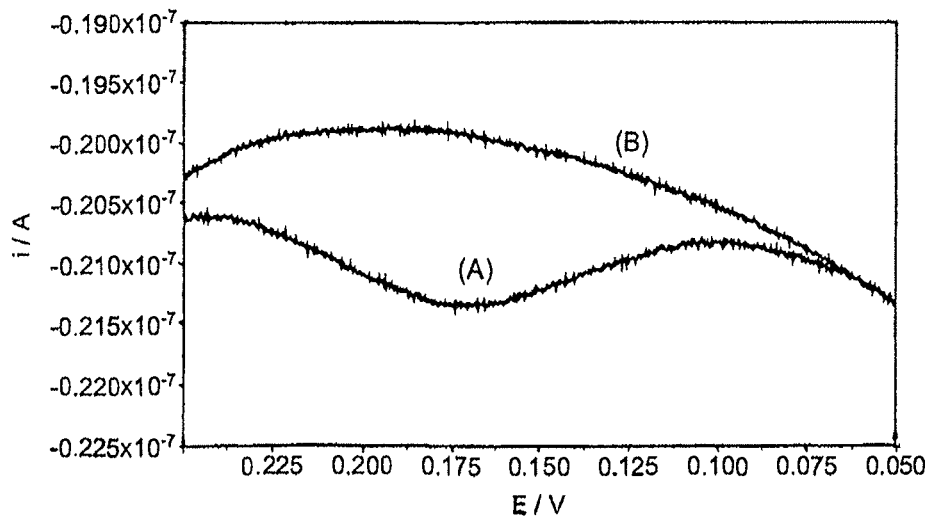
Figure 18C:
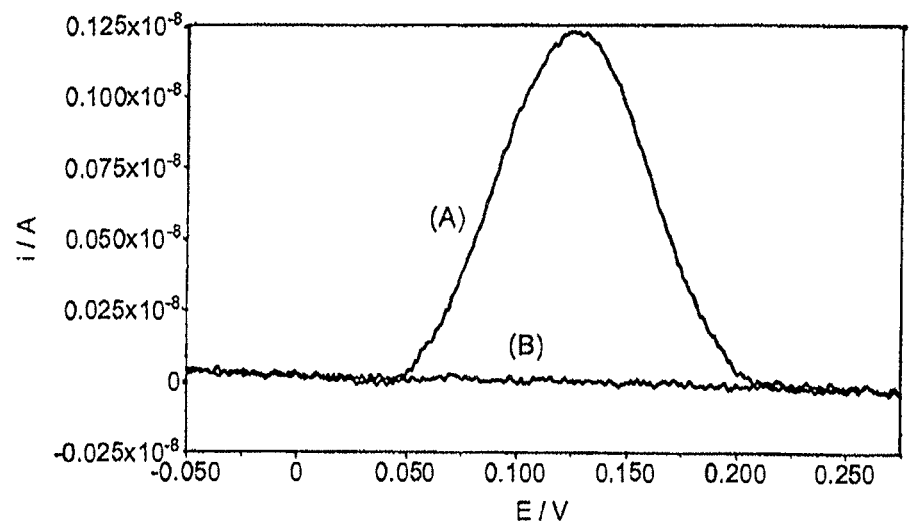
Figure 18D:
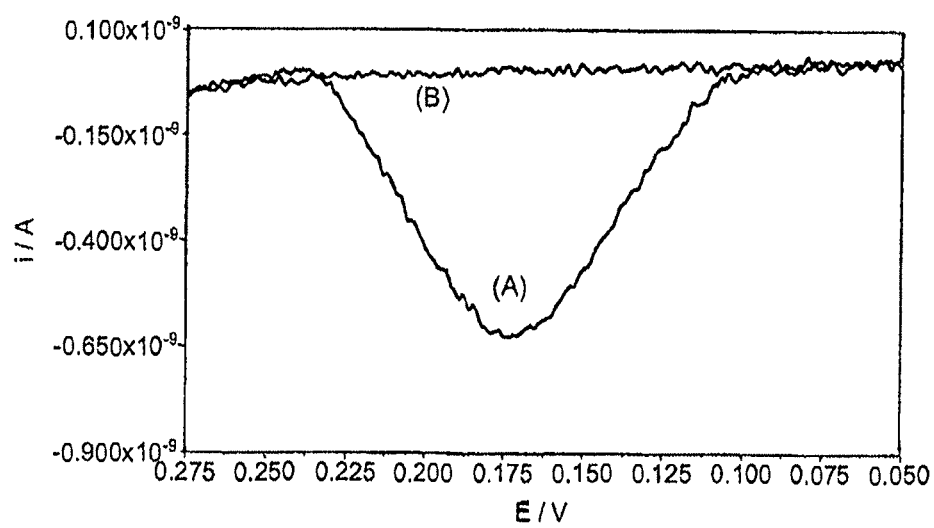
Figure 19A:
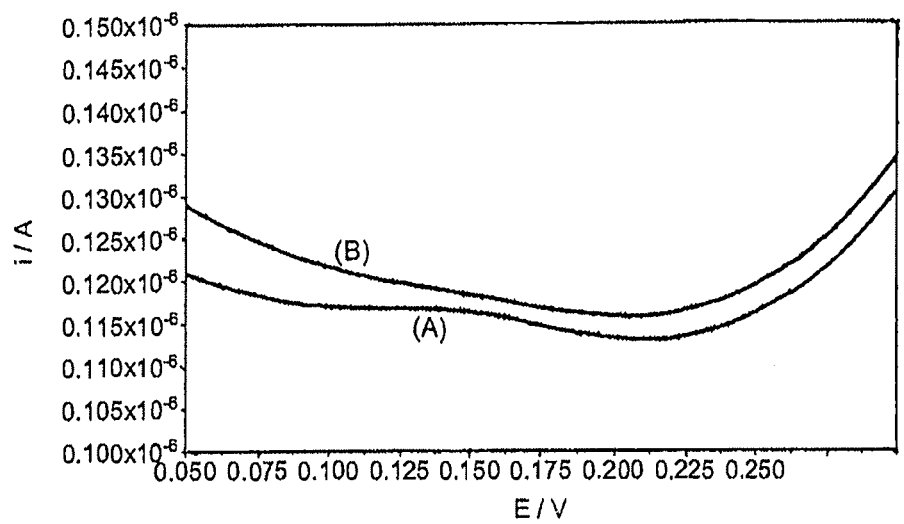
Figure 19B:
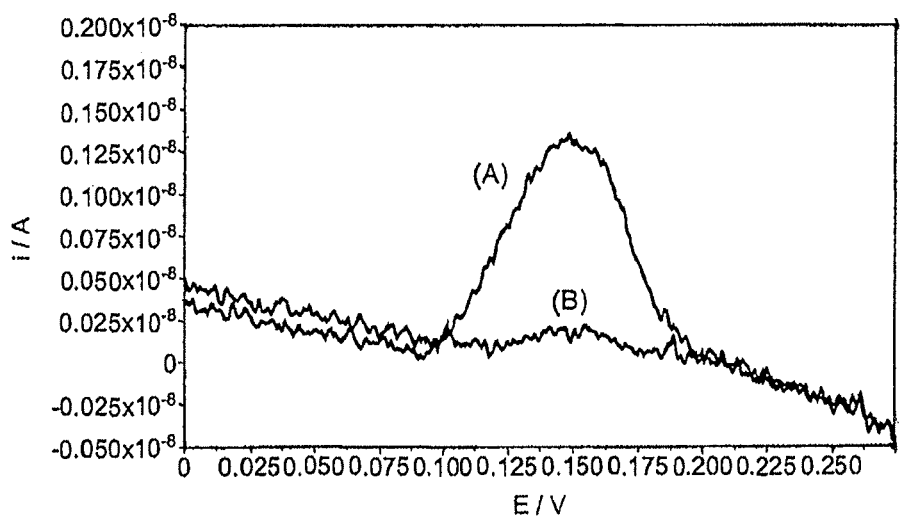
Figure 20A:
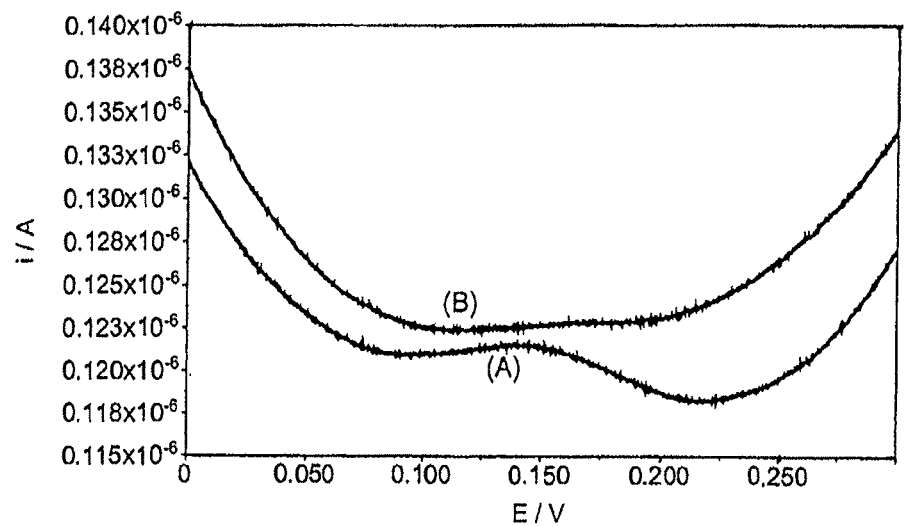
Figure 20B:
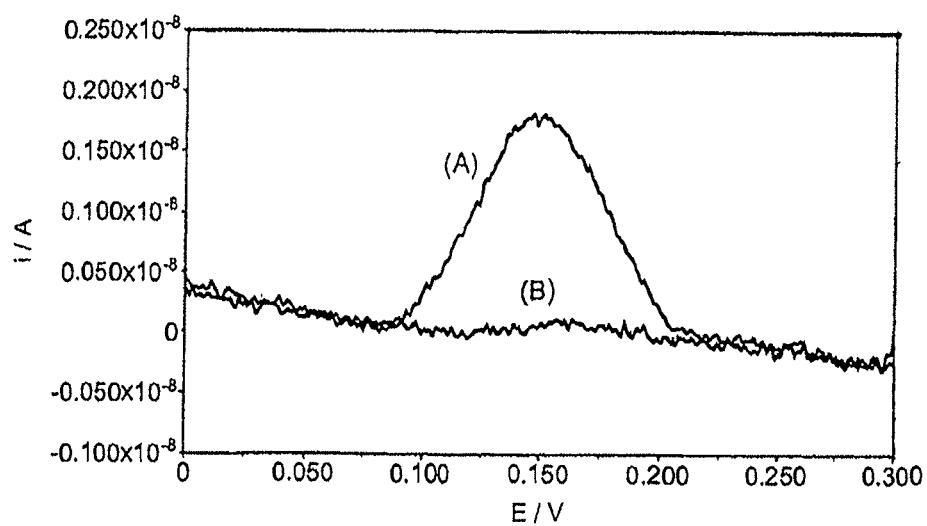

PCR Amplification with Unmodified Primers, End Point Probe Annealing and T7 Exonuclease Digestion
PCR amplifications were performed as described above. On completion of the PCR, samples were heated to 95° C. for 2 minutes, during this time ferrocenylated oligonucleotide probe was added (0.5 μM final concentration). Samples were cooled to 25° C. and incubated at 25° C. for 5 minutes. T7 exonuclease (5 μl, 2 Uμl$^{-1}$) was added to the crude PCR mix and samples incubated for a further 20 minutes.
Two 100 μl reactions were prepared and pooled prior to voltammetric analysis.
The results were as follows:
Beta Actin PCR Amplification
Line A shows positive PCR target amplification reaction and line B shows non-target amplification control throughout
Probe: BAPR ferrocenylated via a C12 linker
Forward target amplification primer: BAF
Reverse target amplification primer: BAR
Forward non-target amplification primer: GSDF
Reverse non-target amplification primer: GSDR
FIG. 18A: normal data, anodic sweep
FIG. 18B: baseline corrected data, anodic sweep
HFE Gene PCR Amplification
Line A shows positive PCR target amplification reaction and line B shows non-target amplification control throughout
Probe: H63DP ferrocenylated via a C12 linker
Forward target amplification primer: H63DF
Reverse target amplification primer: H63DR Forward non-target amplification primer: C282YF
Reverse non-target amplification primer: C282YR
FIG. 19A: normal data, anodic sweep
FIG. 19B: baseline corrected data, anodic sweep
HFE Gene PCR C282Y Mutation Amplification
Line A shows positive PCR target amplification reaction and line B shows non-target amplification control throughout
Probe: C282YP ferrocenylated via a C12 linker
Forward target amplification primer: C282YF
Reverse target amplification primer: C282YR
Forward non-target amplification primer: H63DF
Reverse non-target amplification primer: H63DR
FIG. 20A: normal data, anodic sweep
FIG. 20B: baseline corrected data, anodic sweep

EXAMPLE 10(C)

PCR amplification with unmodified primers, end point probe annealing and T7 exonuclease digestion: Stoffel Fragment.

PCR, probe annealing and T7 exonuclease digestion was performed as described in the above section, substituting Amplitaq Gold DNA Polymerase and supplied buffer with Amplitaq DNA Polymerase Stoffel Fragment and supplied buffer.

Figure 21A:
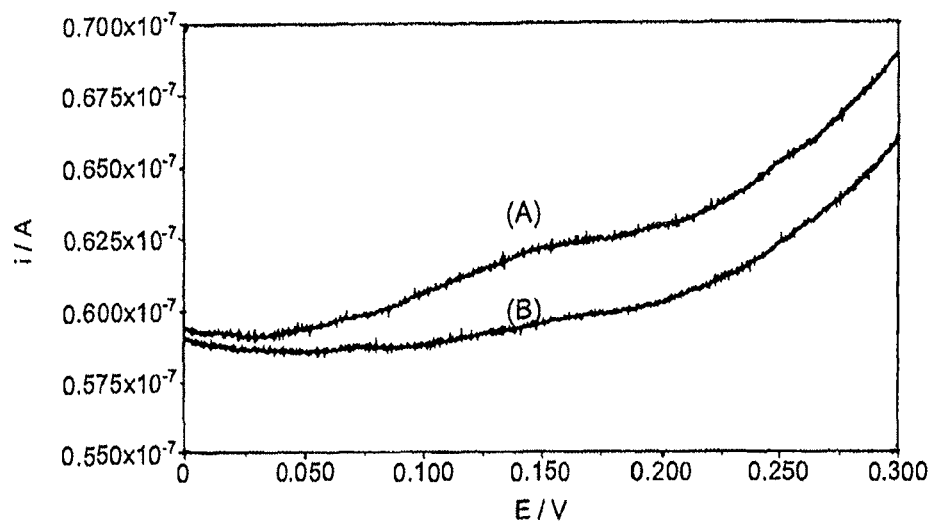
FIGS. 21A and 21B are differential pulse voltammograms illustrating PCR amplification with Stoffel fragment (Example 10(c))
Figure 21B:
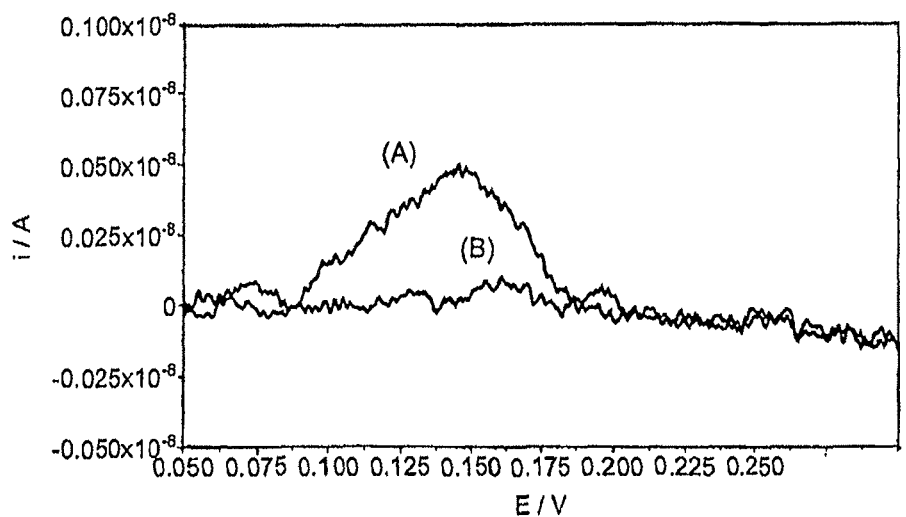

The results were as follows:
HFE Gene PCR Amplification
Line A shows positive PCR target amplification reaction and line B shows non-target amplification control throughout
Probe: C282YP ferrocenylated via a C12 linker
Forward target amplification primer: C282YF
Reverse target amplification primer: C282YR
Forward non-target amplification primer: H63DF
Reverse non-target amplification primer: H63DR
FIG. 21A: normal data, anodic sweep
FIG. 21B: baseline corrected data, anodic sweep

EXAMPLE 10(D)

PCR amplification with unmodified primers, end point probe annealing and T7 exonuclease digestion: No T7 exonuclease control.

PCR and probe annealing was performed as described in example 9c, using Amplitaq Gold DNA polymerase. No T7 exonuclease was added to the PCR mix.

Figure 22A:
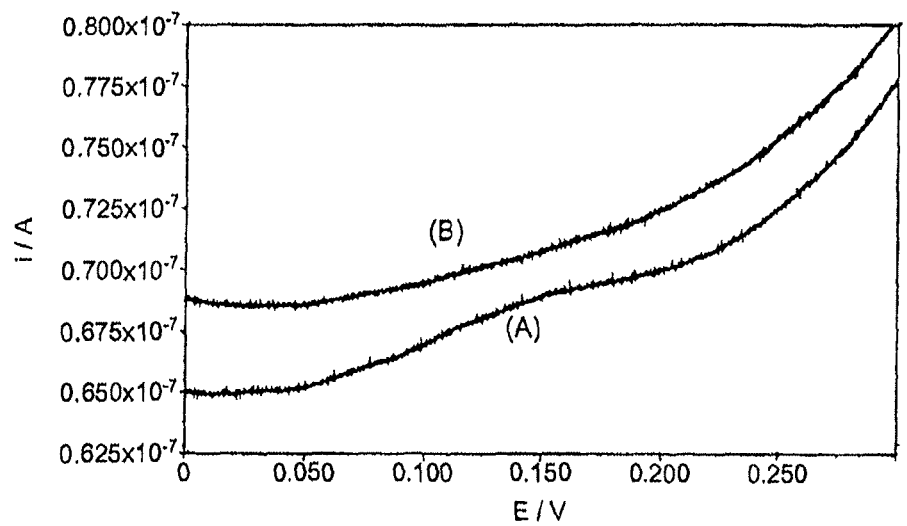
FIGS. 22A and 22B are differential pulse voltammograms illustrating experiments with no T7 exonuclease (Example 10(d)).
Figure 22B:
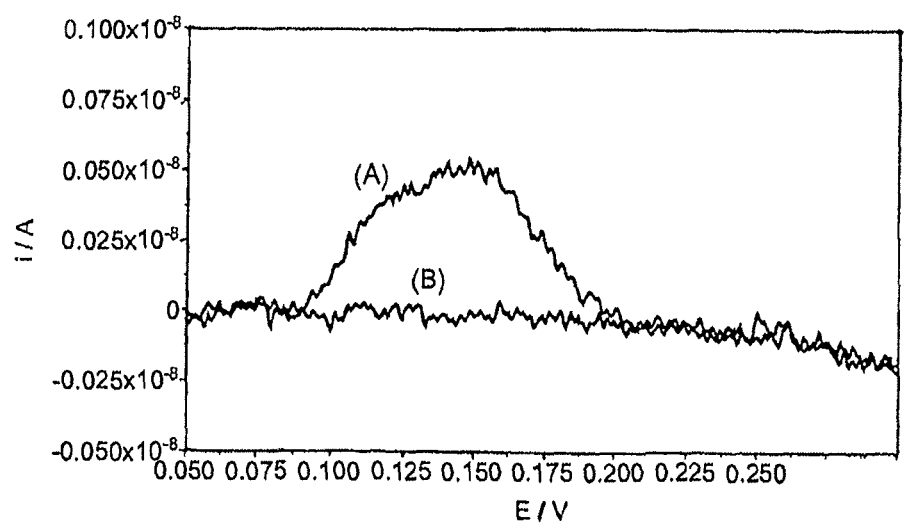

The results were as follows:
HFE Gene PCR Amplification
Line A shows positive PCR target amplification reaction and line B shows non-target amplification control throughout
Probe: C282YP ferrocenylated via a C12 linker
Forward target amplification primer: C282YF
Reverse target amplification primer: C282YR
Forward non-target amplification primer: H63DF
Reverse non-target amplification primer: H63DR
FIG. 22A: normal data, anodic sweep
FIG. 22B: baseline corrected data, anodic sweep

EXAMPLE 11

Figure 23A:
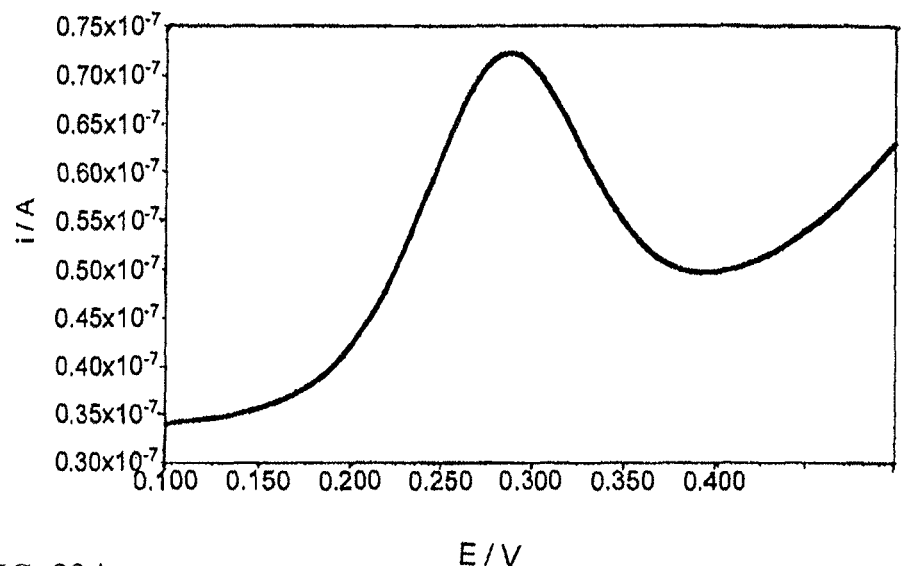
FIGS. 23A and 23B are differential pulse voltammograms illustrating the electrode potential of ferrocene carboxylic acid at 10 µM and 1 µM concentration respectively and FIG. 23C and FIG. 23D are differential pulse voltammograms illustrating the electrode potential of 4-(3'-ferrocenylureido)-1-benzoic acid at 10 µM and 1 µM concentration respectively.
Figure 23B:
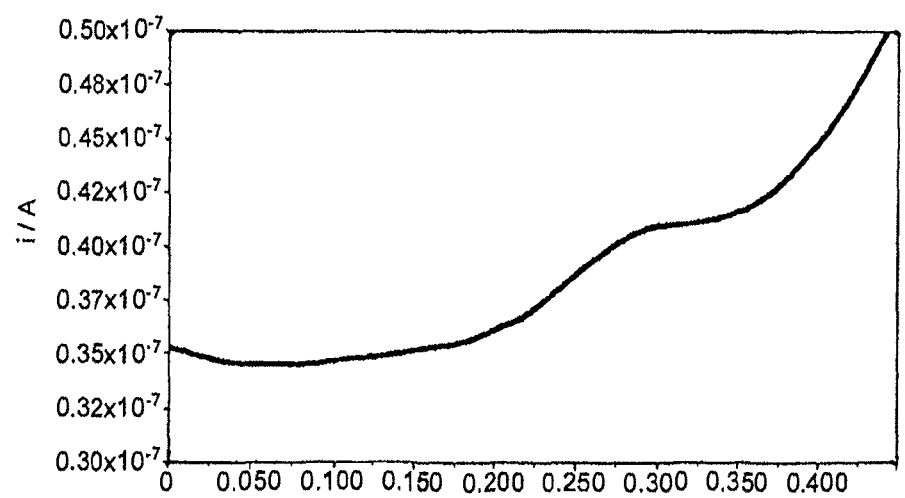
Figure 23C:
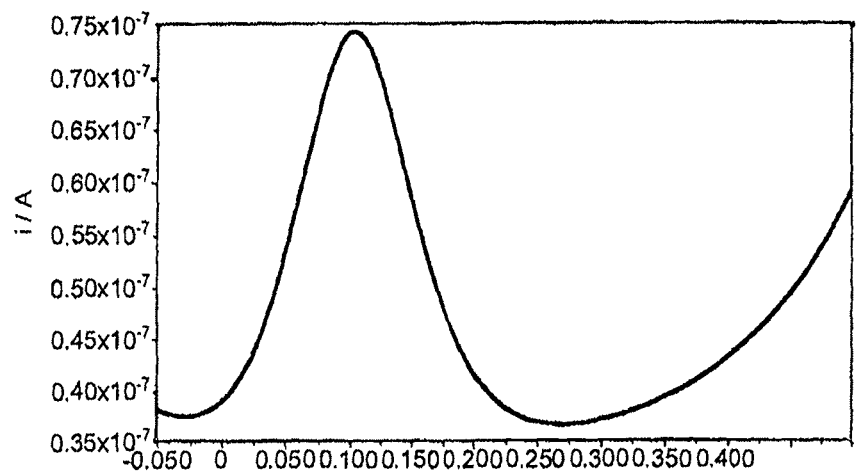
Figure 23D:
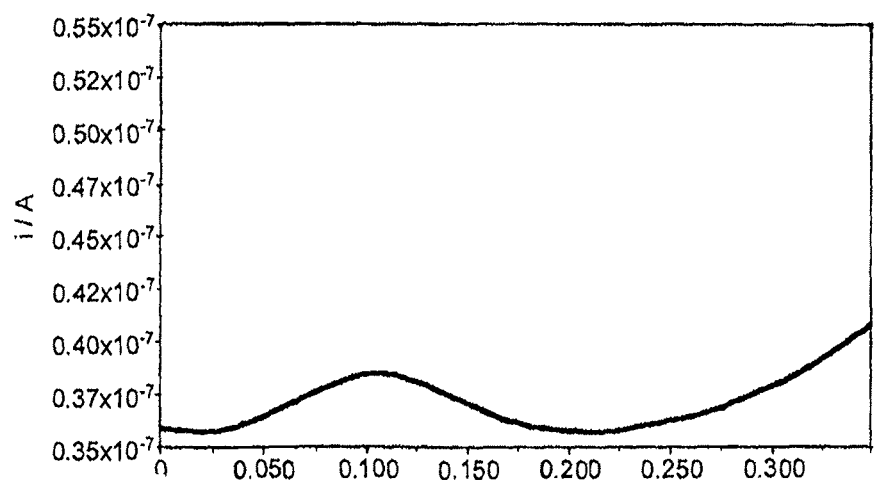

Differential Pulse Voltammogram Analysis of Ferrocene Carboxylic Acid and 4-(3'-ferrocenylureido)-1-benzoic Acid Solutions of ferrocene carboxylic acid and 4-(3'-ferrocenylureido)-1-benzoic acid were prepared at 10 µM and 1 µM concentration in 100 mM aqueous sodium chloride with 10% DMSO. 200 µl sample volumes were used for differential pulse analysis in an apparatus as described in Example 1 with a gold working electrode. The differential pulse conditions were as in Table 3. FIGS. 23A and 23B show the voltammograms for ferrocene carboxylic acid at 10 µM and 1 µM respectively, and FIGS. 23C and 23D show the voltammograms for 4-(3'-ferrocenylureido)-1-benzoic acid at 10 µM and 1 µM respectively.

EXAMPLE 12

Differential Pulse Voltammogram Analysis of S1 Nuclease Digestion of a Mixture of Ferrocenylated Oligonucleotides Three oligonucleotide digestion reactions were carried out as detailed above in Example 4.

In reaction (a) the substrates were BAPR oligonucleotide labelled at the 5' end by ferrocene with a 12 carbon spacer moiety (2.5 µM) and MC11w oligonucleotide labelled at the 5' end by 4-(3-ferrocenylureido)-1-benzoic acid with a 12 carbon spacer moiety (1.5 µM). In reaction (b), the substrate was BAPR oligonucleotide labelled at the 5' end by ferrocene with a 12 carbon spacer moiety only (2.5 µM). In reaction (c), the substrate was MC11w oligonucleotide labelled at the 5' end by 4-(3-ferrocenulureido)-1-benzoic acid with a 12 carbon spacer moiety only (1.5 µM).

After completion of each digestion reaction, the reaction mixtures were analysed by differential pulse voltammetry under the conditions detailed in table 3, except that the end potential was 0.5V. A gold working electrode was used. The voltammograms are presented in FIGS. 24A, 24B, and 24C, respectively. Data is presented with baseline correction. As is seen in the figures, the 4-(3-ferrocenylureido)-1-benzoic acid label has a peak in the differential pulse voltammogram at around 130 mV whilst the ferrocene label has a peak at around 370 mV. The peaks are sufficiently far apart to be resolvable in a mixture as seen in FIG. 24A. The resolvability of the two peaks makes the two labels suitable for use in a multiplex experiment in which two different target sequences are simultaneously probed in the same reaction mixture.

---

What is claimed is:

1. A method of detecting a target nucleic acid sequence in a nucleic acid solution, comprising:

contacting the nucleic acid solution with one or more oligonucleotide probes each labeled with a metallocene moiety, wherein each oligonucleotide probe is covalently linked to a metallocene moiety;

providing conditions at which one or more of the oligonucleotide probes hybridize with a complementary target sequence present in the nucleic acid solution and form a double stranded hybridized nucleic acid, wherein each of the one or more oligonucleotide probes is complementary along its length to the target sequence;

degrading the double stranded hybridized nucleic acid by digestion with a duplex specific nuclease to form at least one of a mononucleotide degraded probe labeled with the metallocene moiety and a dinucleotide degraded probe labeled with the metallocene moiety, wherein the duplex specific nuclease is capable of degrading the oligonucleotide probe only when the oligonucleotide probe is present in the double stranded hybridized nucleic acid and, in the presence of the double stranded hybridized nucleic acid, the duplex specific nuclease degrades the oligonucleotide probe to form at least one of a mononucleotide degraded probe labeled with the metallocene moiety and a dinucleotide degraded probe labeled with the metallocene moiety; and electrochemically detecting a signal based on redox characteristics of the mononucleotide probe labeled with the metallocene moiety, the dinucleotide degraded probe labeled with the metallocene moiety, and any unhybridized oligonucleotide probe in the solution, wherein the signal is influenced by at least the size of the probe to which the metallocene moiety is attached; and wherein the signal of the mononucleotide probe or the dinucleotide probe detects the target nucleic acid sequence in the nucleic acid solution.

2. The method of claim 1, wherein each of the one or more oligonucleotide probes is covalently linked to a metallocene moiety via a spacer comprising an aliphatic chain having 4 to 20 carbon atoms.

3. The method according to claim 1, wherein detecting the target sequence is used for the detection of nucleic acid polymorphisms.

4. The method according to claim 1, wherein the method detects an amplified target nucleic acid in the solution.

5. The method according to claim 1, wherein a single metallocene moiety is attached to the 5'-terminal nucleotide of each of the one or more oligonucleotide probes.

6. The method according to claim 1, wherein a single metallocene moiety is attached to the 3'-terminal nucleotide of each of the one or more oligonucleotide probes.

7. The method according to claim 1, wherein multiple metallocene moieties are attached along the length of each of the one or more oligonucleotide probes.

8. The method of claim 1, wherein the duplex specific nuclease is T7 exonuclease.

9. The method of claim 1, wherein the metallocene moiety is a ferrocene moiety.

10. The method according to claim 2, wherein the spacer is an aliphatic chain having 6 carbon atoms.

11. The method of claim 1, wherein detecting the target sequence is used for detection of allelic polymorphisms.

12. The method of claim 1, wherein detecting the target sequence is used for the detection of single nucleotide polymorphisms.

13. The method of claim 1, wherein detecting the target sequence is used for the quantification of nucleic acid species.

14. The method of claim 1, wherein detecting the target sequence is used for the quantification of gene expression.

15. The method of claim 1, wherein electrochemically detecting the signal of the mononucleotide probe, the dinucleotide probe, and any unhybridized oligonucleotide probe is by voltammetry.

16. The method of claim 1, wherein electrochemically detecting the signal of the mononucleotide probe, the dinucleotide probe, and any unhybridized oligonucleotide probe is by an amperometric technique.

17. The method of claim 1, wherein electrochemically detecting the signal of the mononucleotide probe, the dinucleotide probe, and any unhybridized oligonucleotide probe is by differential pulse voltammetry.

18. The method of claim 9, wherein the ferrocene moiety is a di-ferrocene moiety.

19. The method according to claim 9, wherein multiple oligonucleotide probes are each labeled with different derivatives of ferrocene.

20. The method according to claim 19, wherein the different derivatives of ferrocene have peaks at distinct voltages.

* * * * *